United States Patent
Falk et al.

(10) Patent No.: US 10,519,502 B2
(45) Date of Patent: Dec. 31, 2019

(54) MITOCHONDRIAL DISEASE GENETIC DIAGNOSTICS

(71) Applicant: The Children's Hospital of Philadelphia, Philadelphia, PA (US)

(72) Inventors: Marni J. Falk, Voorhees, NJ (US); Xiaowu Gai, La Canada Flintridge, CA (US); Douglas C. Wallace, Swarthmore, PA (US); Hongbo Xie, Dresher, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

(21) Appl. No.: 15/032,520

(22) PCT Filed: Oct. 31, 2014

(86) PCT No.: PCT/US2014/063449
§ 371 (c)(1),
(2) Date: Apr. 27, 2016

(87) PCT Pub. No.: WO2015/066485
PCT Pub. Date: May 7, 2015

(65) Prior Publication Data
US 2016/0258021 A1      Sep. 8, 2016

Related U.S. Application Data

(60) Provisional application No. 61/898,171, filed on Oct. 31, 2013.

(51) Int. Cl.
*C12Q 1/6883* (2018.01)

(52) U.S. Cl.
CPC ....... *C12Q 1/6883* (2013.01); *C12Q 2600/16* (2013.01)

(58) Field of Classification Search
CPC .................................................. C12Q 1/6883
USPC ........................................................ 506/16
See application file for complete search history.

(56) References Cited

U.S. PATENT DOCUMENTS

| | | | |
|---|---|---|---|
| 5,464,945 A | 11/1995 | Reynolds et al. | |
| 2007/0083334 A1* | 4/2007 | Mintz | G16B 40/00 702/19 |
| 2011/0045471 A1 | 2/2011 | Parr et al. | |
| 2013/0149371 A1 | 6/2013 | Burzio et al. | |
| 2014/0378350 A1* | 12/2014 | Hindson | C12Q 1/6806 506/26 |

FOREIGN PATENT DOCUMENTS

| | | |
|---|---|---|
| WO | 1995/001454 A1 | 1/1995 |
| WO | 2006/008045 A1 | 1/2006 |
| WO | 2012/075230 A1 | 6/2012 |

OTHER PUBLICATIONS

Tessa, A., et al., "Maternally inherited deafness associated with a T1095C mutation in the mDNA" Eur. J. Hum. Genet. (2001) 9(2):147-9.
Li, Z. et al., "Mutational analysis of the mitochondrial 12S rRNA gene in Chinese pediatric subjects with aminoglycoside-induced and non-syndromic hearing loss" Hum. Genet. (2005) 117(1):9-15.
Falk, M.J., et al., "Mitochondrial disease genetic diagnostics: optimized whole-exome analysis for all MitoCarta nuclear genes and the mitochondrial genome" Discov. Med. (2012) 14(79):389-99.
Gai, X., "Mitochondrial Disease Genetic Diagnostics: Optimized whole-exome analysis for all MitoCarta nuclear genes and the mitochondrial genome" Poster presentation at The American Society of Human Genetics 2012 Annual Meeting, Nov. 9, 2012, San Francisco, CA.
CHOP News, "One-step Gene Test for Mitochondrial Diseases", Jan. 29, 2013, available at http://www.chop.edu/news/one-step-gene-test-mitochondrial-diseases.
McCormick, E., et al., "Molecular genetic testing for mitochondrial disease: from one generation to the next" Neurotherapeutics (2013) 10(2):251-61.
Calvo, S.E., et al., "The mitochondrial proteome and human disease" Annu. Rev. Genomics Hum. Genet. (2010) 11:25-44.
Calvo, S.E., et al., "Molecular diagnosis of infantile mitochondrial disease with targeted next-generation sequencing" Sci. Transl. Med. (2012) 4(118):118ra10.
Zhou, et al., "Microarray Technology and Applications in Environmental Microbiology" Advances in Agronomy (2004) 82:183-270.
Xie, et al., "Mitochondrial genome sequence analysis: A custom bioinformatics pipeline substantially improves Affymetrix MitoChip v2.0 call rate and accuracy" BMC Bioinformatics (2011) 12:402.
Maitra, et al., "The Human MitoChip: A High-Throughput Sequencing Microarray for Mitochondrial Mutation Detection" Genome Res. (2004) 14: 812-819.

* cited by examiner

*Primary Examiner* — Karla A Dines
(74) *Attorney, Agent, or Firm* — Robert C. Netter, Jr.; Dann, Dorfman, Herrell & Skillman, P.C.

(57) ABSTRACT

Mitochondrial disease genetic diagnostics and methods of use thereof are provided.

19 Claims, 26 Drawing Sheets

Figure 1:
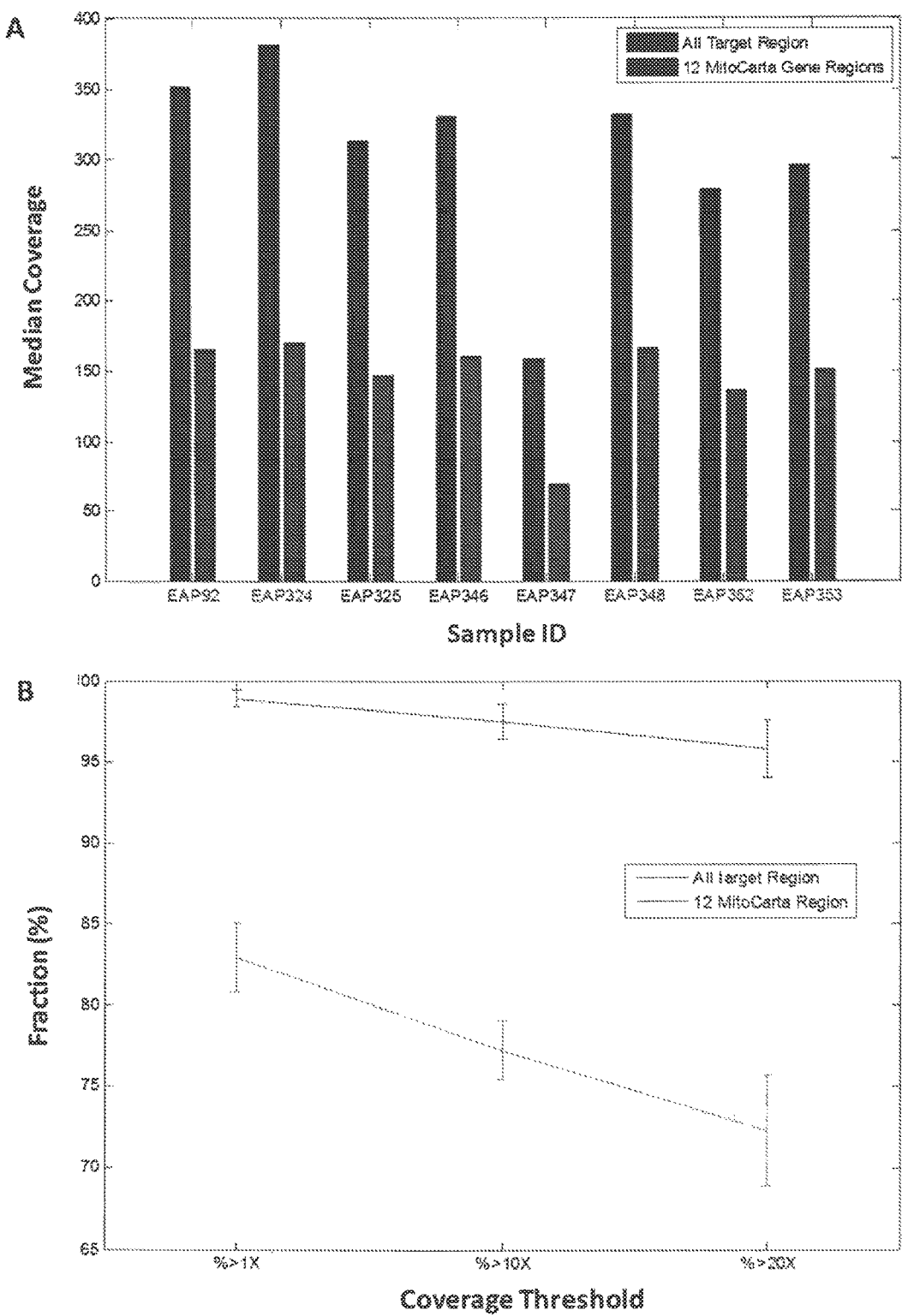

Specification includes a Sequence Listing.

Figure 6A

Figure 6B

| | | | | | | CCCCAGGGATAACAGGGCAATCCTATTCAAGAGTCAATATCAATCAACAATAGG |
|---|---|---|---|---|---|---|
| | | | | | | GTTTACGACCTCGATGTTGGATCAGGACATCCTGATGGTGCAGCCGCTA |
| chrM | 2928 | 3048 1_24 | 1000 | + | chrM:2929-3048 | TGAAAAGTTCGTTTGTTCAAC |
| | | | | | | GATTAAAGTCCTACGTGATCTGAGTTCAGACCGGAGTAATCCAGGTCGG |
| chrM | 3048 | 3168 1_25 | 1000 | + | chrM:3049-3168 | TTTCTATCTACTTCAAATTCCTCCCTGTACGAAAGGACAAGAGAAATAAG |
| | | | | | | GCCTACTTCACAAAGCGCCTT |
| chrM | 4118 | 4238 1_34 | 1000 | + | chrM:4119-4238 | TATGAATTGGARCAGGATACCCGATCCTGATACGGAATCCATACAC |
| | | | | | | CTCCTATGAAAAAACTTCCTACCACTCACCCTAGCATTACTTATATGATAT |
| | | | | | | GTCTCCATACCCATTACAA |
| chrM | 3758 | 3758 1_30 | 1000 | + | chrM:3639-3758 | TAGCCGTTTACTCAATCCTCTGATCAAGGGTGAGCATCAAAATCAAATTAC |
| | | | | | | GCCCTCATCCTGCCTCACTCGCAGAAGAGCCAAACCAATCCGAATGAAG |
| | | | | | | TCACCCTAGCCATCATTCTAC |
| chrM | 3758 | 3878 1_31 | 1000 | + | chrM:3759-3878 | TATCAACATTACTAATAAGTGGCTCCTTAACCTCTCCACCCTATCACAA |
| | | | | | | CACAAGAACAACCTCTGATTACTCCTGCCATCATGACCCTTGGCCATAAAT |
| | | | | | | GATTTATCTCCACACTAG |
| chrM | 3878 | 3998 1_32 | 1000 | + | chrM:3879-3998 | CAGAGACCAACCGAACCCCCTTCGACCTTGCCGAAGGGGAGTCGCAA |
| | | | | | | CTAGTCTCAGGCTTCAACATCGAATACGCCGCAGGCCCATTCGCCCTATT |
| | | | | | | CTTCATAGCCGAATACACAAACA |
| chrM | 3518 | 3638 1_29 | 1000 | + | chrM:3519-3638 | ACAATCACGCCCCGACCCCTAGCTCTACCCATGGCTCTTACTATGAAACC |
| | | | | | | CCCTCCCATACCCCATAACCCCAACCAATCTCCCTAAGCCGGCTACGACA |
| | | | | | | ATTCTAGGCCACCCTTAGGC |
| chrM | 3398 | 3518 1_28 | 1000 | + | chrM:3399-3518 | TACAACTAGGCAAAGGCCCGAACGTTGTAGGCCCTACGGCTACGACA |
| | | | | | | ACCCTTGGTGAGCCATAAAAATCTTCACCAAAGAGCCCTAAAAGCCC |
| | | | | | | GCCACTACTACCATACCCTCT |
| chrM | 3998 | 4118 1_33 | 1000 | + | chrM:3999-4118 | TTATTATAATAAACACCTCACCTATACAATCCCTCTTCAGGAAAACATATG |
| | | | | | | ACGCACTCTCCCCGAACTCCACACAACCATATTTTGTCACCAAGACCCTA |
| | | | | | | CTTTCTAACCTCCTCGTTCT |
| chrM | 4844 | 4964 1_40 | 1000 | + | chrM:4845-4964 | ATCCGGGCTGCCTTCCTCACTATGACAAAATAGCCCCCATCACATCAA |
| | | | | | | TATACCAAATCTCTCCCTACTAAGCCTAGAAGCCTTCTCCTCACTCTCAA |
| | | | | | | TCTTATCCATCATCAGACAAGG |
| chrM | 5564 | 5684 1_46 | 1000 | + | chrM:5565-5684 | CAATACTTAATTCTGAACAGCTAAGCACTCCAAAACCCATCTCGGCAT |
| | | | | | | CAACTCGAAGCAACGAATCAGGCCCATTTAATTAAGCCTTACTCTAGACC |
| | | | | | | AATGAGACTTAAACCACAA |

| Band | A 1X | B 1.5X | C 1.6X | D 1.1X | E 1.2X | F 900 | G 1100 | H 1.1X (natural) | 50 MA |
|---|---|---|---|---|---|---|---|---|---|
| Min. | 0 | 0 | 0 | 0 | 0 | 0 | 0 | 0 | 0 |
| 1st Qu. | 125 | 87 | 151 | 132 | 140 | 241 | 245 | 121 | 132 |
| Median | 242 | 170 | 306 | 255 | 269 | 469 | 474 | 260.1 | 245 |
| Mean | 322.4 (±310) | 226.7 | 413 | 339 | 361.3 | 621.8 | 634.5 | 319.9 | 329.5 |
| 3rd Qu. | 411 | 290 | 532 | 432 | 456 | 793 | 811 | 433 | 415 |
| Max. | 8017 | 8017 | 8000 | 7994 | 8014 | 8019 | 8032 | 7993 | 7993 |
| % >= 1X | 99.20% | 99.00% | 99.10% | 99.40% | 99.20% | 99.20% | 99.20% | 99.40% | 99.40% |
| % >= 10X | 97.10% | 96.00% | 97.20% | 97.50% | 97.30% | 98.10% | 98.10% | 97.10% | 97.30% |
| % >= 20X | 95.00% | 93.10% | 95.30% | 95.30% | 95.50% | 96.90% | 96.90% | 96.20% | 96.60% |

Figure 7

| GENOME | COVERAGE | mtDNA:nuclear baits ratio | | | | | | | | Nuclear baits only | |
|---|---|---|---|---|---|---|---|---|---|---|---|
| | | 1:1 | 1:10 | 1:50 | 1:100 | 1:200 | 1:500 | 1:1000 | | Mitocarta+50 Mb (Nuclear only) | 50 Mb Whole Exome |
| NUCLEAR | MEDIAN | 242 | 170 | 306 | 255 | 269 | 469 | 476 | | 240 | 246 |
| | % ≥ 2X | 99.2% | 99.0% | 98.3% | 98.4% | 98.2% | 98.2% | 99.0% | | 99.4% | 98.4% |
| | % ≥ 10X | 97.1% | 96.0% | 97.2% | 97.6% | 97.3% | 98.1% | 98.1% | | 97.1% | 97.3% |
| | % ≥ 20X | 95.5% | 93.1% | 95.2% | 95.5% | 95.0% | 95.3% | 95.0% | | 94.9% | 95.6% |
| mtDNA | MEDIAN | 7821 | 7821 | 7819 | 7919 | 4497 | 4013 | 2254 | | 118 | 103 |
| | % ≥ 10X | 100.0% | 100.0% | 100.0% | 100.0% | 100.0% | 100.0% | 100.0% | | 100.0% | 100.0% |
| | % ≥ 100X | 100.0% | 100.0% | 100.0% | 100.0% | 100.0% | 100.0% | 99.9% | | 99.8% | 100.0% |
| | % ≥ 500X | 100.0% | 100.0% | 100.0% | 100.0% | 99.9% | 100.0% | 99.9% | | 72.2% | 99.9% |
| | % ≥ 1000X | 100.0% | 99.9% | 99.9% | 99.8% | 99.1% | 99.1% | 95.0% | | 0.0% | 0.0% |

Figure 8

| Gene Name | OMIM # | Associated Disease(s) and Phenotype(s) | Inheritance Pattern |
|---|---|---|---|
| AARS2 | *612035 | Combined Oxidative Phosphorylation Deficiency 8; Infantile Mitochondrial Cardiomyopathy[159] | Autosomal recessive |
| ABCB7 | *300135 | Anemia, Sideroblastic and Spinocerebellar Ataxia[1,2] | X-linked |
| ACAD9 | *611103 | Acyl-CoA dehydrogenase 9 deficiency; ACAD9 Deficiency; Mitochondrial complex I deficiency due to ACAD9 Deficiency[3] | Autosomal recessive |
| ADCK3 (CABC1; COQ8) | *606980 | Coenzyme Q10 Deficiency; Spinocerebellar Ataxia, Autosomal Recessive 9[24,25] | Autosomal recessive |
| AIFM1 | *300169 | Combined oxidative phosphorylation deficiency 6; COXPD6; Encephalomyopathy, Mitochondrial, X-Linked[4] | X-linked |
| ALAS2 | *301300 | Anemia, Hereditary Sideroblastic, X-linked[1,2] Protoporphyria, erythropoietic, X-linked dominant. | X-linked |
| APTX | *606350 | Ataxia with Oculomotor Apraxia 1 (AOA1); Cerebellar ataxia with Muscle coenzyme Q10 deficiency[5,6] | Autosomal recessive |
| ATP5E | *606153 | Mitochondrial complex V (ATP Synthase) deficiency, Nuclear Type 3; MC5DN3[7] | Autosomal recessive |
| ATPAF2 (ATP12) | *608918 | Mitochondrial complex V (ATP Synthase) Deficiency, Nuclear Type 1; MC5DN1[8] | Autosomal recessive |
| AUH | *600529 | 3-Methylglutaconic Aciduria, Type 1; MGA, Type 1; 3-Methylglutaconyl-CoA Hydratase Deficiency[9] | Autosomal recessive |
| BCS1L | *603647 | Bjornstad syndrome; GRACILE syndrome; Mitochondrial Complex III Deficiency; Leigh Syndrome[10,11,12] | Autosomal recessive |
| C10ORF2 (Twinkle, PEO1) | *606075 | C10orf2-Related Ataxia Neuropathy Spectrum Disorders; Mitochondrial DNA Depletion Syndrome 7, Hepatocerebral Form; Progressive External Ophthalmoplegia with Mitochondrial DNA Deletions 3[14,15,16,17,18,19,20] | Autosomal dominant AND Autosomal recessive |
| C12ORF65 | *613541 | Combined Oxidative Phosphorylation Deficiency 7; COXPD7[21] | Autosomal recessive |
| C20ORF7 | *612360 | Mitochondrial Complex I Deficiency[22,23] | Autosomal recessive |
| C8ORF38 | *612392 | Leigh syndrome due to mitochondrial complex I deficiency[13] | Autosomal recessive |
| CISD2 (WFS2) | *611507 | Wolfram Syndrome 2 (DIDMOAD: diabetes insipidus, diabetes mellitus, optic atrophy, and deafness)[26,27] | Autosomal recessive |
| COQ2 | *609825 | Coenzyme Q10 Deficiency; CoQ10 deficiency, Primary[28] | Autosomal recessive |
| COQ9 | *612837 | Coenzyme Q10 Deficiency; CoQ10 Deficiency, Primary[29] | Autosomal recessive |
| COX10 | *602125 | Mitochondrial Complex IV Deficiency, Cytochrome c Oxidase Deficiency; Leigh Syndrome[30] | Autosomal recessive |
| COX15 | *603646 | Mitochondrial Complex IV Deficiency; Cytochrome c Oxidase Deficiency[31] | Autosomal recessive |
| COX6B1 | *124089 | Mitochondrial Complex IV Deficiency; Cytochrome c Oxidase Deficiency[32] | Autosomal recessive |
| DARS2 | *610956 | Leukoencephalopathy with Brain Stem and Spinal Cord Involvement and Lactate Elevation[33] | Autosomal recessive |
| DGUOK | *601465 | Mitochondrial DNA Depletion Syndrome 3 (hepatocerebral type)[34,35,36] | Autosomal recessive |

Figure 10A

| Gene Name | OMIM # | Associated Disorder(s) (Phenotype(s)) | Mode of Inheritance |
|---|---|---|---|
| DLAT | *608770 | Pyruvate dehydrogenase E2 Deficiency; Leigh syndrome; Lactic Acidemia due to defect of E2 lipoyl transacetylase of the pyruvate dehydrogenase complex[37] | Autosomal recessive |
| DLD | *238331 | E3 deficiency (Maple syrup urine disease, type III); Leigh syndrome[38] | Autosomal recessive |
| DNAJC19 | *608977 | 3-methylglutaconic aciduria, type V; dilated cardiomyopathy and ataxia[39] | Autosomal recessive |
| DNM1L | +603850 | Lethal Encephalopathy due to Defective Mitochondrial Fission[40] | Autosomal dominant |
| ETFA | *608053 | Multiple acyl-CoA dehydrogenase deficiency; Glutaricaciduria, type IIA[160,161,162] | Autosomal recessive |
| ETFB | *130410 | Multiple acyl-CoA dehydrogenase deficiency; Glutaricaciduria, type IIB[160,161,162] | Autosomal recessive |
| ETFDH | *231675 | Multiple acyl-CoA Dehydrogenation Deficiency; Glutaricaciduria, Type IIC[160,161,162] | Autosomal recessive |
| ETHE1 | *608451 | Ethylmalonic encephalopathy[163,164,165] | Autosomal recessive |
| FASTKD2 | *612322 | Mitochondrial Complex IV Deficiency[41] | Autosomal recessive |
| FBP1 | *611570 | Fructose-1,6-Bisphosphatase Deficiency; Lactic acidosis[166] | Autosomal recessive |
| FH | *136850 | Fumarate Hydratase Deficiency; Fumaric Aciduria; Fumarase Deficiency[42,43] Leiomyomatosis and renal cell cancer; Multiple cutaneous and uterine leiomyomata | Autosomal recessive; Autosomal dominant |
| FOXRED1 | *613622 | Leigh syndrome due to mitochondrial complex I deficiency[44] | Autosomal recessive |
| G6PC | *613742 | Glycogen Storage Disease Ia; Lactic acidosis[169] | Autosomal recessive |
| GFER | *600924 | Myopathy, Mitochondrial Progressive, with Congenital Cataract, Hearing Loss and Developmental Delay[45] | Autosomal recessive |
| GFM1 (EFG1) | *606639 | Combined Oxidative Phosphorylation Deficiency 1; COXPD1; Hepatoencephalopathy, Early Fatal Progressive[46,47,48] | Autosomal recessive |
| GYS2 | *138571 | Glycogen Storage Disease, Type 0, Liver; Lactic acidosis[166,167,168] | Autosomal recessive |
| ISCU | *611911 | Myopathy with Deficiency of ISCU; Iron-Sulfur Cluster Deficiency Myopathy; Myopathy with Deficiency of Succinate Dehydrogenase and Aconitase; Myopathy with Exercise Intolerance, Swedish Type[49,50] | Autosomal recessive |
| LRPPRC | *607544 | Complex IV deficiency; Leigh syndrome, French-Canadian Type[51] | Autosomal recessive |
| MPV17 | *137960 | Mitochondrial DNA Depletion Syndrome 6 (Hepatocerebral type)[54] | Autosomal recessive |
| MRPS16 | *609204 | Combined Oxidative Phosphorylation Deficiency 2; COXPD2; Agenesis of Corpus Callosum with Dysmorphism and Fatal Lactic Acidosis[55] | Autosomal recessive |
| MRPS22 | *605810 | Combined Oxidative Phosphorylation Deficiency 5; COXPD5[56] | Autosomal recessive |
| NDUFA1 | *300078 | Mitochondrial Complex I Deficiency; NADH-Coenzyme Q Reductase Deficiency[57,58,59] | X-linked |
| NDUFA10 | *603835 | Leigh Syndrome due to Mitochondrial Complex I Deficiency[61] | Autosomal recessive |

Figure 10B

| Gene Name | OMIM # | Associated disease(s) (references) | Inheritance Pattern |
|---|---|---|---|
| NDUFA11 | *612638 | Mitochondrial complex I deficiency presented with encephalocardiomyopathy or fatal infantile lactic acidemia[62] | Autosomal recessive |
| NDUFA2 | *602137 | Leigh syndrome due to mitochondrial complex I deficiency[60] | Autosomal recessive |
| NDUFAF1 | *606934 | Mitochondrial complex I deficiency and cardioencephalomyopathy[63,64] | Autosomal recessive |
| NDUFAF2 | *609653 | Mitochondrial Complex I Deficiency; Leigh Syndrome[65,66,67] | Autosomal recessive |
| NDUFAF3 (C3ORF60) | *613911 | Mitochondrial Complex I Deficiency[68] | Autosomal recessive |
| NDUFAF4 (C6ORF66) | *611776 | Mitochondrial Complex I Deficiency[68] | Autosomal recessive |
| NDUFS1 | *157655 | Mitochondrial Complex I Deficiency[69,70,21,72,73,74]; Leigh syndrome or Leigh-like syndrome | Autosomal recessive |
| NDUFS2 | *602985 | Mitochondrial Complex I Deficiency[70,75] | Autosomal recessive likely[a] |
| NDUFS3 | *603846 | Leigh Syndrome; Leigh Syndrome due to Mitochondrial Complex I Deficiency[73,74] | Autosomal recessive likely[a] |
| NDUFS4 | *602694 | Mitochondrial complex I deficiency; Leigh Syndrome[76,77,78,79,80] | Autosomal recessive |
| NDUFS6 | *603848 | Mitochondrial complex I deficiency and fatal neonatal lactic acidemia[81,82] | Autosomal recessive |
| NDUFS7 | *601825 | Leigh Syndrome due to Mitochondrial Complex I Deficiency[83,84,85] | Autosomal recessive likely[a] |
| NDUFS8 | *602141 | Leigh Syndrome due to Mitochondrial Complex I Deficiency[70,71,86,87] | Autosomal recessive likely[a] |
| NDUFV1 | *161015 | Alexander Disease; Leigh Syndrome; Mitochondrial Complex I Deficiency[70,71,72,73,74,88] | Autosomal recessive |
| NDUFV2 | *600532 | Mitochondrial Complex I Deficiency. Possible association with Parkinson Disease[72,73,89,90] | Autosomal recessive with exception[b] |
| NUBPL | *613621 | Mitochondrial complex I deficiency with mitochondrial encephalomyopathy[44] | Autosomal recessive |
| OPA1 | *605290 | Optic Atrophy I; Optic Atrophy with or without deafness, ophthalmoplegia, myopathy, ataxia and neuropathy[91,92] | Autosomal dominant; Semi-dominant |
| OPA3 | *606580 | 3-Methylglutaconic Aciduria, Type 3; Costeff Syndrome; Optic Atrophy Plus Syndrome[93,94] | Autosomal recessive; Optic Atrophy Autosomal dominant |
| PC | *608786 | Pyruvate carboxylase deficiency; Leigh syndrome[97,98] | Autosomal recessive |
| PDHA1 | *300502 | Pyruvate Dehydrogenase E1-alpha Deficiency; Leigh Syndrome, X-linked[99] | X-linked |
| PDHB | *179060 | Pyruvate dehydrogenase (E1-beta) deficiency; Lactic acidosis and neurologic dysfunction[100] | Autosomal recessive |
| PDHX | *608769 | Pyruvate Dehydrogenase E-3 Binding Protein (Component X) Deficiency; Lactic Acidemia due to Defect in Lipoyl-Containing Component X of the Pyruvate Dehydrogenase Complex[101] | Autosomal recessive |
| PDP1 | *605993 | Pyruvate dehydrogenase phosphatase deficiency; lactic acidosis resulting in acute respiratory distress and early death[102,103] | Autosomal recessive |
| PDSS1 | *607429 | Coenzyme Q10 Deficiency; CoQ10 deficiency, Primary[104] | Autosomal recessive |

Figure 10C

| Gene Name | OMIM # | Associated Disease(s) (OMIM reference) | Inheritance Pattern |
|---|---|---|---|
| PDSS2 | *610564 | Coenzyme Q10 Deficiency; CoQ10 Deficiency, Primary[105] | Autosomal recessive |
| POLG (POLG1) | *174763 | Mitochondrial DNA Depletion Syndrome (types 4A [Alpers type] and 4B [MNGIE type]); Mitochondrial Recessive Ataxia Syndrome (SANDO and SCAE); Progressive External Opthalmoplegia, Autosomal Recessive AND Autosomal Dominant[107,108,109] | Autosomal dominant AND Autosomal recessive |
| POLG2 | *604983 | Progressive External Ophthalmoplegia (PEO) with Mitochondrial DNA Deletions, Autosomal Dominant[110,111] | Autosomal dominant |
| PUS1 | *608109 | Myopathy, Lactic Acidosis and Sideroblastic Anemia 1[113,114] | Autosomal recessive |
| RARS2 | *611524 | Pontocerebellar Hypoplasia Type 6; PCH6[115] | Autosomal recessive |
| RRM2B | *604712 | Mitochondrial DNA Depletion Syndrome (types 8A and 8B); Progressive External Ophthalmoplegia (PEO) with Mitochondrial DNA Deletions, Autosomal Dominant, 5[116,117,118] | Autosomal dominant AND Autosomal recessive |
| SARS2 (FBXO17) | *612804 | Hyperuricemia, Pulmonary Hypertention, Renal Failure, and Alkalosis; HUPRA Syndrome[119] | Autosomal recessive |
| SCO1 | *603644 | Cytochrome Oxidase-Deficiency, Hepatic Failure and Encephalopathy[120] | Autosomal recessive |
| SCO2 | *604272 | Cytochrome Oxidase Deficiency and Early Onset, Fatal Hypertrophic Cardiomyopathy (HCM)[121,122] | Autosomal recessive |
| SDHAF1 | *612848 | Mitochondrial Complex II Deficiency; Succinate Dehydrogenase Complex Assembly Factor 1 Deficiency[124] | Autosomal recessive |
| SLC25A3 (PHC) | *600370 | Mitochondrial Phosphate Carrier Deficiency[125] | Autosomal recessive |
| SLC25A4 (ANT1) | *103220 | Progressive External Ophthalmoplegia (PEO) with Mitochondrial DNA Deletions 3; Cardiomyopathy, Familial Hypertrophic (CMH)[18,20] | Autosomal dominant (PEO); Autosomal recessive (CMH) |
| SPG7 | *602783 | Spastic Paraplegia 7; Hereditary Spastic Paraplegia, Paraplegin Type[128] | Autosomal recessive |
| SUCLA2 | *603921 | Mitochondrial DNA Depletion Syndrome 5 (encephalomyopathic type with methylmalonic aciduria)[129] | Autosomal recessive |
| SUCLG1 | *611224 | Mitochondrial DNA Depletion Syndrome 9 (encephalomyopathic type with methylmalonic aciduria)[130,131,132] | Autosomal recessive |
| SURF1 | *185620 | Leigh Syndrome due to Mitochondrial Complex IV Deficiency[133,134,135,136] | Autosomal recessive |
| TACO1 | *612958 | Leigh Syndrome due to Mitochondrial Complex IV Deficiency[137] | Autosomal recessive |
| TAZ | *300394 | Barth syndrome; 3-Methylglutaconic Aciduria Type II; TAZ-related dilated cardiomyopathy[138,139] | X-linked |
| TIMM8A (DDP1) | *300356 | Mohr-Tranebjaerg Syndrome (Deafness-Dystonia-Optic Atrophy Syndrome [DDON]); Jensen Syndrome (Opticoacoustic Nerve Atrophy with Dementia)[140] | X-linked |
| TK2 | *188250 | Mitochondrial DNA Depletion Syndrome 2 (myopathic type)[141,142,143,144] | Autosomal recessive |
| TMEM126A | *612988 | Optic Atrophy 7; Nonsyndromic autosomal recessive optic atrophy[146] | Autosomal recessive |
| TMEM70 | *612418 | Mitochondrial Complex V (ATP Synthase) Deficiency, Nuclear Type 2; Encephalocardiomyopathy, Mitochondrial, Neonatal, Due to ATP Synthase Deficiency[145] | Autosomal recessive |
| TRMU | *610230 | Liver Failure, Acute Infantile[147] | Autosomal recessive |

Figure 10D

| Gene | OMIM | Associated Disease/Phenotype | Inheritance Pattern |
|---|---|---|---|
| TSFM | *604723 | Combined Oxidative Phosphorylation Deficiency 3[148] | Autosomal recessive |
| TTC19 | *613814 | Mitochondrial Complex III Deficiency[149] | Autosomal recessive |
| TUFM | *602389 | Combined Oxidative Phosphorylation Deficiency 4[150] | Autosomal recessive |
| TYMP (ECGF1, TP) | *131222 | Mitochondrial DNA Depletion Syndrome 1 (MNGIE Type)[151,152,153] | Autosomal recessive |
| UQCRB | *191330 | Mitochondrial Complex III Deficiency, UQCRB-Related[154] | Autosomal recessive |
| UQCRQ | *612080 | Mitochondrial Complex III Deficiency, UQCRQ-Related[155] | Autosomal recessive |
| WFS1 | *606201 | WFS1-Related Disorders; Wolfram Syndrome (DIDMOAD: diabetes insipidus, diabetes mellitus, optic atrophy, and deafness); Wolfram Syndrome-Like Disease; DFNA6/14/38 Nonsyndromic Low-Frequency Sensorineural Hearing Loss[156,157] | Autosomal recessive AND Autosomal dominant |
| YARS2 | *610957 | Myopathy, Lactic Acidosis and Sideroblastic Anemia 2[158] | Autosomal recessive |

<sup>a</sup> While autosomal recessive inheritance is most likely, these case reports should be noted. See references as indicated for each gene for additional information:
NDUFS2: Single NDUFS2 mutation identified in affected individual who also harbored a single NDUFA8 mutation[70]
NDUFS3: Single NDUFS3 missense mutation identified in individual affected with Complex I Deficiency[71]
NDUFS7: Single heterozygous NDUFS7 mutation identified in individual affected with Complex I Deficiency[70]
NDUFS8: 2 affected individuals identified with single NDUFA8 mutation; one of these individuals also harbored single NDUFS2 mutation[70,72]
<sup>b</sup> Heterozygous missense change p.A29V in NDUFV2 has been associated with Parkinson Disease[68]

Figure 10E

References: 1. Camaschella (2008) Br J Haem 143:27-38. 2. Bergmann et al., (2010) Ped Blood Ca 54:273-278. 3. He et al., (2007) Am J Hum Genet 81:87-103. 4. Ghezzi et al., (2010) Am J Hum Genet 86:639-649. 5. Onodera (2006) Neuropath 26:361-367. 6. Castelloti et al., (2011, Apr 5) Neurogen [Epub ahead of print]. 7. Mayr et al., (2010) Hum Mol Genet 19:3430-3439. 8. De Meirleir et al., (2004) J Med Genet 41:120-124. 9. Wortmann et al., (2010) Neurology 75:1079-1083. 10. de Lonlay et al., (2001) Nat Genet 29:57-60. 11. Hinson et al., (2007) N Engl J Med 356:809-19. 12. Visapaa et al., (2002) Am J Hum Genet 71:863-876. 13. Pagliarini et al., (2008) Cell 134:112-123. 14. Hudson et al., (2005) Neurology 64:371-3. 15. Nikali et al., (2005) Hum Mol Genet 14:2981-2990. 16. Hakonen et al., (2007) Brain 130:3032-40. 17. Sarzi et al., (2007) Ann Neurol 62:579-87. 18. Agostino et al., (2003) Neurology 60:1354-1356. 19. Lewis, et al., (2002) J Neurol Sci 201:39-44. 20. Virgilio et al., (2008) J Neurol 255:1384-1391. 21. Antonicka et al., (2010) Am J Hum Genet 87:115-122. 22. Sugiana et al., (2008) Am J Hum Genet 83:468-478. 23. Gerards et al., (2009) J Med Genet [Epub ahead of print]. 24. Mollet et al., (2008) Am J Hum Genet 82:623-630. 25. Lagier-Tourenne et al., (2008) Am J Hum Genet 82:661-672. 26. Chaussenot et al., (2011) Ann Neurol 69:501-508. 27. Anss et al., (2007) Am J Hum Genet 81:673-683. 28. Quinzii et al., (2008) Biofactors 32(1-4):113-118. 29. Duncan et al., (2009) Am J Hum Genet 84:558-566. 30. Coenen et al., (2004) Ann Neurol 56:560-564. 31. Antonicka et al., (2003) Am J Hum Genet 72:101-114. 32. Massa et al., (2008) Am J Hum Genet 82:1281-1289. 33. Isohanni et al., (2010) J Med Genet 47:66-70. 34. Sarzi et al., (2007) J Pediatrics 105:531-4. 35. Slama et al., (2005) Mol Genet Metab 86:462-465. 36. Freisinger et al., (2006) Arch Neurol 63:1129-1134. 37. Head et al., (2005) Ann Neurol 58:234-241. 38. Shaag et al., (1999) Am J Med Genet 82:177-182. 39. Davey et al., (2006) J Med Genet 43:385-393. 40. Wartenham, (2007) N Eng J Med 356:1736-1741. 41. Ghezzi et al., (2008) Am J Hum Genet 83:415-423. 42. Ottolenghi et al., (2011) Hum Mut 32(0):1-7. 43. Bayley et al., (2008) BMC Med Genet 9:20. 44. Calvo et al., (2010) Nat Genet 42:851-858. 45. Di Fonzo et al., (2009) Am J Hum Genet 84:594-604. 46. Valente et al., (2007) Am J Hum Genet 80:44-58. 47. Coenen et al., (2004) N Engl J Med 351:2080-6. 48. Antonicka et al., (2006) Hum Mol Genet 15:1835-1846. 49. Kollberg et al., (2009) Brain 132:2170-2179. 50. Olsson et al., (2008) Hum Genet 17(11):1666-1672. 51. Debray et al., (2011) J Med Genet 48:183-189. 55. Miller et al., (2004) Ann Neurol 56:734-738. 56. Saada et al., (2007) J Med Genet 44:784-786. 57. Potluri et al., (2009) Mol Genet Metab 96:189-195. 58. Fernandez-Moreira et al., (2007) Ann Neurol 61:73-83. 59. Loeffen et al., (1998) J Inher Metab Dis 21:210-215. 60. Saskia et al., (2008) Am J Hum Genet 82:1306-1315. 61. Hoefs et al., (2011) Eur J Hum Genet 19(3):270-274. 62. Berger et al., (2008) Ann Neurol 63:405-408. 63. Dunning et al., (2007) The EMBO Journal 26:3227-3237. 64. Jonssen et al., (2003) J Clin Invest 110:264-270. 65. Ogilvie et al., (2005) J Clin Invest 115:2784-2792. 66. Hoefs et al., (2009) Hum Mutat 30:E728-E736. 67. Barghuti et al., (2008) Mol Genet Metab 94:78-82. 68. Saada et al., (2009) Am J Hum Genet 84:718-727. 69. Hoefs et al., (2010) Mol Genet Metab 100:251-6. 70. Bugiani et al., (2004) Biochimica et Biophysica Acta 1659:136-147. 71. Benit et al., (2001) Am J Hum Genet 68:1344-1352. 72. Hinttala et al., (2005) J Med Genet 83:786-794. 73. Pagnies-Mammeri et al., (2009) Mol Genet Metab 96:196-200. 74. Benit et al., (2004) J Med Genet 41:14-17. 75. Loeffen et al., (2001) Ann Neurol 49:195-201. 76. Petruzzella et al., (2001) Hum Mol Genet 10:529-535. 77. Budde et al., (2000) Biochem Biophys Res Commun 275:63-68. 78. Leshinsky-Silver et al., (2009) Mol Genet Metab 97:185-189. 79. Benit et al., (2003) Hum Genet 112:563-566. 80. van den Heuvel et al., (1998) Am J Hum Genet 62:262-268. 81. Spiegel et al., (2009) Eur J Hum Genet 17:1200-1203. 82. Kirby et al., (2004) J Clin Invest 114:837-845. 83. Lebon et al., (2007) Mol Genet Metab 92:104-108. 84. Lebon et al., (2007) Mol Genet Metab 90:379-382. 85. Triepels et al., (1999) Ann Neurol 45:787-790. 86. Procaccio, V. and Wallace, D. (2004) Neurology 62:1899. 87. Loeffen et al., (1998) Am J Hum Genet 63:1598-1608. 88. Schuelke et al., (1999) Nat Genet 21:260-261. 89. Benit et al., (2003) Hum Mutat 21:582-586. 90. Hattori et al., (1998) Genomics 49:52-58. 91. Ferre et al., (2009) Hum Mutat 30:E692-705. 92. Stewart et al., (2008) Neurology 71:1829-1531. 93. Yu-Wai-Man et al., (2011) Ophthal 118(3):558-563. 94. Wortmann et al., (2010) J Inherit Metab Dis [Pub online Sept 30 2010]. 97. Marin-Valencia et al., (2010) Mol Genet Metab 101(1):9-17. 98. Monnot et al., (2009) Hum Mut 30(5):734-740. 99. Brown et al., (2006) Dev Med Child Neurol 48:756-60. 100. Okajima et al., (2008) Mol Genet Metab 93(4):371-380. 101. Barnerias et al., (2010) Dev Med & Child Neurol 52:e1-e9. 102. Cameron et al., (2009) Hum Genet 125(3):319-326. 103. Maj et al., (2005) J Clin Endocrinol Metab 90(7):4101-4107. 104. Mollet et al., (2007) J Clin Invest 117:765-772. 105. Lopez et al., (2006) Am J Hum Genet 79:1125-1129. 107. Horvath et al., (2006) Brain 129:1674-1684. 108. Wong et al., (2008) Hum Mutat 29:E150-E172. 109. Blok et al., (2009, Jul 2) J Med Genet [Epub ahead of print]. 110. Longley et al., (2006) Am J Hum Genet 78:1026-1034. 111. Czermin et al., (2010) J Neurol [Epub ahead of print]. 113. Bergmann et al., (2010) Pediatr Blood Cancer 54:273-278. 114. Fernandez-Vizarra et al., (2007) J Med Genet 44:173-180. 115. Namavar et al., (2011) Brain 134:143-156. 116. Tyynismaa et al., (2009) Am J Hum Genet 85(2):290-295. 117. Kollberg et al., (2009) Neuromuscul Disord 19:147-150. 118. Bornstein et al., (2008) Neuromuscul Disord 18:453-459. 119. Belostotsky et al., (2011) Am J Hum Genet 88(2):193-200. 120. Valnot et al., (2000) Am J Hum Genet 67:1104-1109. 121. Sacconi et al., (2003) Pediatr Res 53:224-230. 122. Jaksch et al., (2000) Hum Mol Genet 9:795-801. 124. Ghezzi et al., (2009) Nat Genet 41:654-656. 125. Mayr et al., (2007) Am J Hum Genet 80:478-484. 128. Antoidi et al., (2008) Hum Mutat 29(4):522-531. 129. Ostergaard et al., (2007) Brain 130:853-861. 130. Valayannopoulos et al., (2010) Mitochondrion 10:335-341. 131. Rivera et al., (2010) Mitochondrion 10:362-368. 132. Ostergaard et al., (2007) Am J Hum Genet 81:383-387. 133. Shoubridge, E. (2001) Hum Mol Genet 10.2277-2284. 134. von Kleist-Retrow et al., (1999) Biochim Biophys Acta 1455:35-44. 135. Pequignot et al., (2001) J Biol Chem 276.15326-15329. 136. Ogawa et al., (2002) Pediatr Neurol 26:196-200. 137. Wesarpachai et al., (2009) Nat Genet 41:833-837. 138. Johnston et al., (1997) Am J Hum Genet 61:1053-1058. 139. Wortmann et al., (2010) J Inherit Metab Dis [Pub online Sept 30 2010]. 140. Tranebjaerg, L. Gene Reviews (2009) Deafness-Dystonia-Optic Neuronopathy Syndrome. 141. Oskoui et al., (2006) Arch Neurol 63:1122-1126. 142. Blakely et al., (2008) Neuromuscul Disord 18:557-560. 143. Mancuso et al., (2002) Neurology 59:1197-1202. 144. Carrozzo et al., (2003) Hum Mutat 21:453-4. 145. Cizkova et al., (2008) Nat Genet 40:1288-1290. 146. Hanein et al., (2009) Am J Hum Genet 84:493-498. 147. Schara et al., (2011) J Inherit Metab Dis 34:197-201. 148. Smeitink et al., (2006) Am J Hum Genet 79:869-877. 149. Ghezzi et al., (2011) Nat Genet 83(3):259-263. 150. Valente et al., (2007) Am J Hum Genet 80:44-58. 151. Hirano et al., (1999) Neurologist 10:8-17. 152. Nishino et al., (1999) Science 283:689-92. 153. Slama et al., (2005) Molec Genet Metab 84:326-331. 155. Barel et al., (2008) Am J Hum Genet 82:1211-1216. 156. Rigoli et al., (2011) Clin Genet 79(2):103-117. 157. Cryns et al., (2003) Hum Mutat 22:275-287. 158. Riley et al., (2010) Am J Hum Genet 87:52-59. 159. Tyynismaa et al., (2011) Am J Hum Genet 88(5):635-642. 160. Schiff, M. et al., (2006) Mol Genet Metab 88(2):153-158. 161. Gordon, N. (2006) Brain Dev 28(3):136-140. 162. Olsen, RKJ, et al., (2003) Hum Mutat 22:12-23. 163. Tiranti et al., (2009) Nature Med 15:200-205. 164. Tiranti et al., (2006) J Med Genet 43:340-346. 165. Minen et al., (2008) J Med Genet 45:473-478. 166. Hjalmarson et al., (2010) J Inherit Metab Dis [Epub ahead of print]. 167. Spiegel et al., (2007) J Pediatr Endocrinol Metab 20(12):1339-1342. 168. Soggia et al., (2010) BMC Med Genet 11(3):1-5. 169. Chou and Mansfield (2008) Hum Mutat 29(7):921-930.

Figure 10F

MITOCHONDRIAL DISEASE GENETIC DIAGNOSTICS

This application is a § 371 application of PCT/US2014/063449, filed Oct. 31, 2014, which claims priority under 35 U.S.C. § 119(e) to U.S. Provisional Patent Application No. 61/898,171, filed on Oct. 31, 2013. The foregoing applications are is incorporated by reference herein.

This invention was made with government support under Grant No. R03-DK082446 awarded by the National Institutes of Health. The government has certain rights in the invention.

FIELD OF THE INVENTION

The present invention relates to the field of mitochondrial diseases. Specifically, the instant invention provides compositions and methods for the diagnosis of mitochondrial diseases.

BACKGROUND OF THE INVENTION

Several publications and patent documents are cited throughout the specification in order to describe the state of the art to which this invention pertains. Each of these citations is incorporated herein by reference as though set forth in full.

Whole-exome sequencing (WES) has emerged as the preferred method to identify disease genes for Mendelian disorders. Indeed, WES is proving particularly valuable for the diagnostic evaluation of individuals with phenotypically and genetically heterogeneous conditions such as suspected mitochondrial disease (McCormick et al. (2013) Neurotherapeutics 10:251-61). Mitochondrial diseases have a wide range of presenting disease manifestations, typically poor genotype-phenotype correlation of any one gene, and a wide range of phenotypically similar non-mitochondrial diseases that must be considered in the differential diagnosis for any given patient (Haas et al. (2007) Pediatrics 120:1326-1333). Known pathogenic mutations causing mitochondrial disease have already been identified in more than 150 nuclear genes and all 37 mtDNA genes (Calvo et al. (2010) Annu. Rev. Genomics Hum. Genet., 11:25-44), although most genes have been linked to only a small number of disease cases and mutations in these known genes collectively account for less than half of cases with suspected mitochondrial disease (Calvo et al. (2012) Sci. Transl. Med., 4:118ra110). Additional pathogenic candidates abound as there are up to 1,500 mitochondrial proteins that are largely nuclear-encoded, of which the MitoCarta set of 1,034 proteins has undergone robust experimental validation and accounts for approximately 85% of all mitochondrial proteins (Pagliarini et al. (2008) Cell 134:112-123). The MitoCarta set includes many known disease genes, including all but 4 nuclear genes (TAZ, PUS1, RRM2B, TYMP) of 77 (Calvo et al. (2012) Sci. Transl. Med., 4:118ra110) previously linked to mitochondrial respiratory chain disease (Tucker et al. (2010) Curr. Neurol. Neurosci. Rep., 10:277-285) and 80 of the nuclear genes on the 101 gene sequencing panel for mitochondrial disease and related disorders that is currently available in the clinical diagnostic setting at GeneDx (Gaithersburg, Md.). Targeted sequence analysis of the MitoCarta gene set together with the mtDNA genome has been estimated to be likely to identify pathogenic causes in at least 47% of all individuals with suspected primary mitochondrial disease (Calvo et al. (2012) Sci. Transl. Med., 4:118ra110). Therefore, sequence analysis of the MitoCarta nuclear gene set, the mtDNA genome, and the entire nuclear exome can reasonably be expected to facilitate genetic diagnosis in more than half of all patients with suspected mitochondrial disease, while also presenting the simultaneous opportunity for novel disease gene discovery. Such analysis is now technically feasible by application of massively parallel sequencing methodologies that have emerged in both the research and clinical settings.

A single unified platform has not been available to reliably permit simultaneous interrogation of all known and potential causes of suspected mitochondrial disease and phenotypically overlapping disorders. Exome capture kits are not all equally designed, do not capture the same target regions, and do not all perform with the same efficiency. Indeed, the early versions of commercially available whole-exome capture kits were found to target significantly different genomic regions and to vary greatly in their overall performance (Asan et al. (2011) Genome Biol., 12:R95; Kiialainen et al. (2011) PLoS One 6:e16486). In addition, no whole-exome capture kit has been optimized to provide highly reliable capture of the MitoCarta nuclear gene set and to provide targeted capture of the mtDNA genome. While off-target capture of the mtDNA genome is inevitable in any whole-exome capture kit, this is typically highly non-reproducible with insufficient coverage to either provide reliable interrogation of the complete mtDNA genome sequence or sensitively detect heteroplasmic mtDNA mutations.

SUMMARY OF THE INVENTION

In accordance with the present invention, compositions comprising oligonucleotides that specifically hybridize (e.g., are complementary) with mitochondrial DNA are provided. In a particular embodiment, the composition comprises at least one oligonucleotide comprising a nucleic acid molecule set forth in FIG. 6. The composition may comprise at least 10, 20, 30, 40, 50, 60, 70, 80, 90, 100, 110, 120, 130, or all of the nucleic acid molecules provided in FIG. 6. The compositions of the instant invention may further comprise oligonucleotides that specifically hybridize with the nuclear genome. In a particular embodiment, the composition further comprises a genome library, exome library, and/or oligonucleotides that specifically hybridize with MitoCarta gene sequences (e.g., those that are not included in the whole exome library, when present). For example, the composition may further comprise oligonucleotides that specifically hybridize with at least 1, 2, 3, 4, 5, 6, 7, 8, 9, 10, 11, 12, 13, 14, 15, or all 16 of the following genes: BCL2, GPX1, LYRM4, MSRB2, NDUFA11, NUDT8, PIGY, PRDX2, PRDX5, SLC25A26, TIMMI17B, ZBED5, C6orf136, HSD17B8, MRPS18B, and TAP1. In a particular embodiment, the ratio of mitochondrial oligonucleotides to nuclear oligonucleotides is about 1:100. Kits comprising one or more compositions of the instant invention are also provided.

In accordance with another aspect of the instant invention, methods of diagnosing a mitochondrial disease in a subject are provided. The instant invention also encompasses methods for identifying mutations associated with a mitochondrial disease or disorder.

BRIEF DESCRIPTIONS OF THE DRAWING

FIGS. 1A and 1B show that standard 50 Mb whole-exome capture kit has inadequate coverage of 12 nuclear genes in the 1,034 MitoCarta gene set. FIG. 1A shows the median fold-coverage in 8 unrelated human blood DNA samples for all standard 50 Mb target regions and the 12 MitoCarta gene regions that were identified to have suboptimal coverage on the standard 50 Mb whole-exome design. Each sample was sequenced in a single flow-cell lane on the Illumina HiSeq 2000. FIG. 1B provides a graph of the fraction (percent) coverage for all 50 Mb target regions and 12 MitoCarta gene regions at varying depths of coverage from 1× to 20×.

Figure 2:
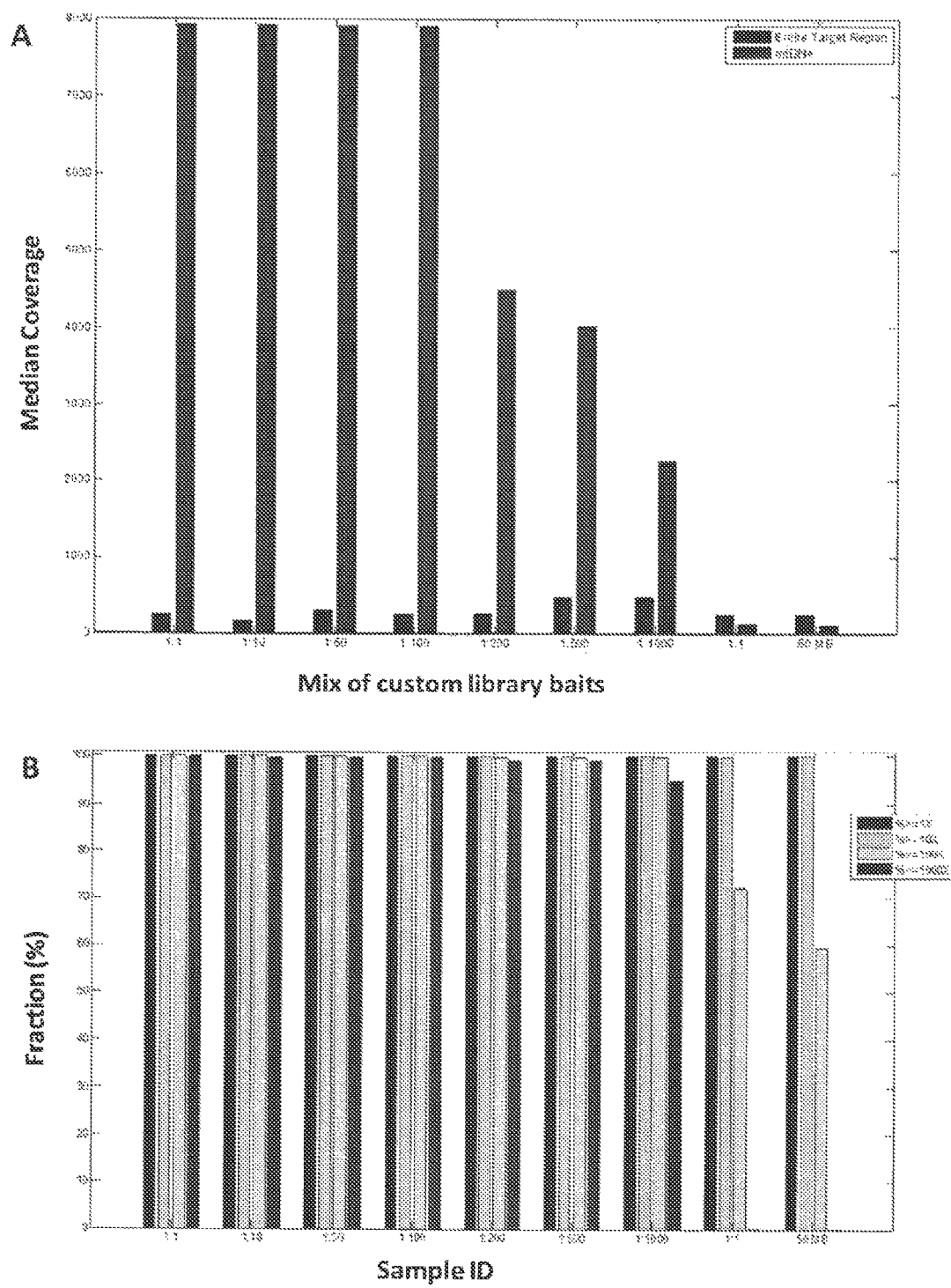

FIGS. 2A and 2B show the coverage analysis of variable mtDNA genome to nuclear capture molar ratios. FIG. 2A provides the median sequence coverage for both the nuclear exome and mtDNA genome for 9 samples captured with different mixes of custom library baits. The first seven sets of bars each represent capture ratios of targeted mtDNA genome (Design C) to nuclear baits (Designs A+B), with molar ratios as labeled. The eighth set of bars indicates a 1:1 ratio of standard 50 Mb whole exome to custom MitoCarta baits for the 12 genes not adequately targeted on the initial design (Designs A+B), but no mtDNA baits were included. The ninth set of bars indicates performance of the standard 50 Mb whole exome platform (Design A). FIG. 2B provides the fraction (percent) of the mitochondrial genome sequenced at variable depths of coverage ranging from 1× to 1000× for the same 9 samples captured with the different molar ratios of custom library baits as described above for FIG. 2A.

Figure 3:
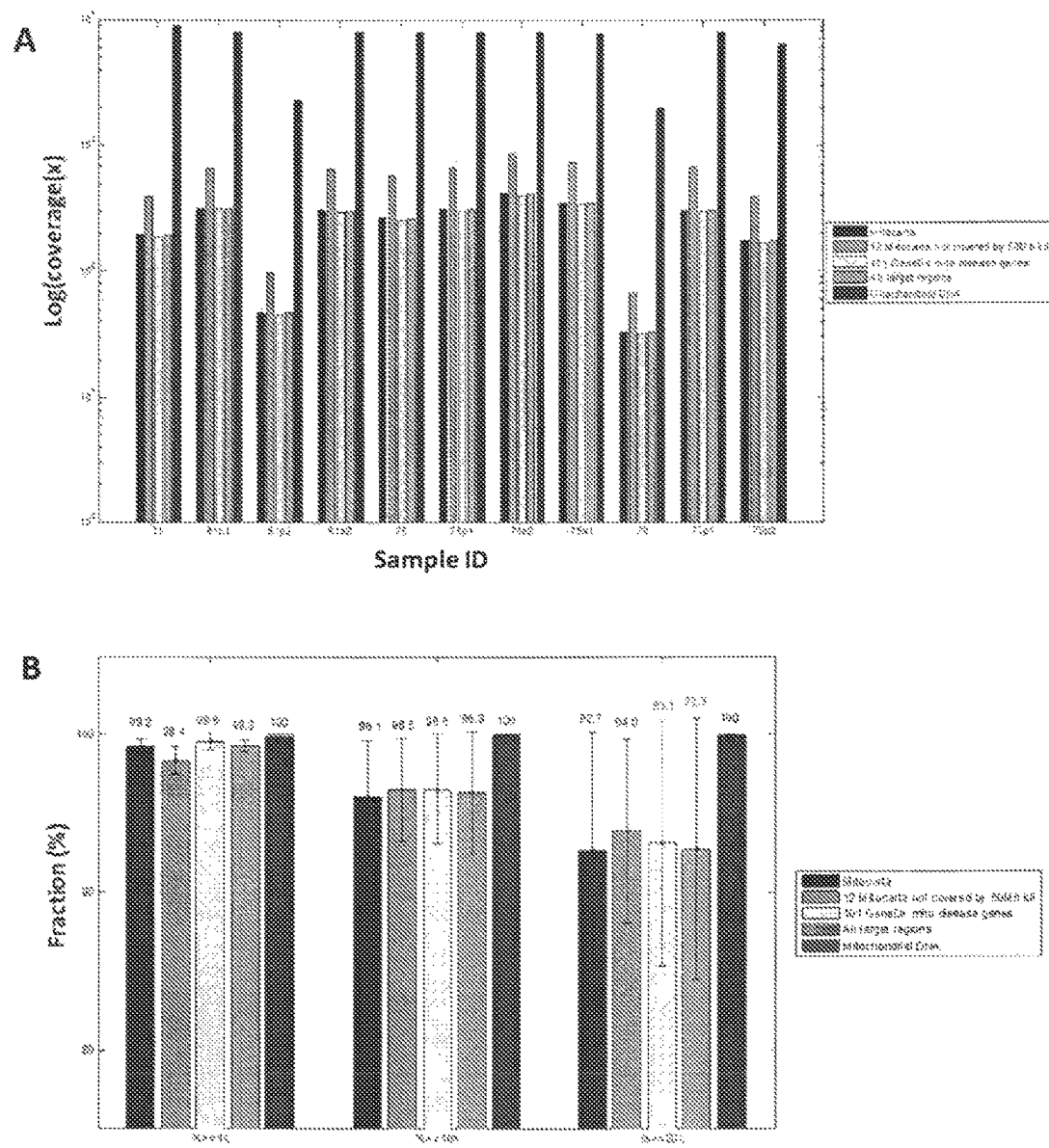

FIGS. 3A and 3B show the coverage statistics of 1:100 Mito-Plus Whole Exome capture and Illumina HiSeq NGS analysis of 11 human blood samples. FIG. 3A provides the median coverage for 5 different gene groups from left to right: all 1,034 MitoCarta genes, 12 MitoCarta genes not covered adequately by the standard 50 Mb whole exome kit, 101 nuclear genes on the commercially-available GeneDx Mitochondrial Disease panel, all target regions, and the mtDNA genome. FIG. 3B provides the fraction (percent) coverage mean and standard deviation across all 11 samples for these same 5 gene groupings at 1×, 10×, and 20× depth of coverage. Each sample was run in a single HiSeq flow-cell lane for NGS analysis.

Figure 4:
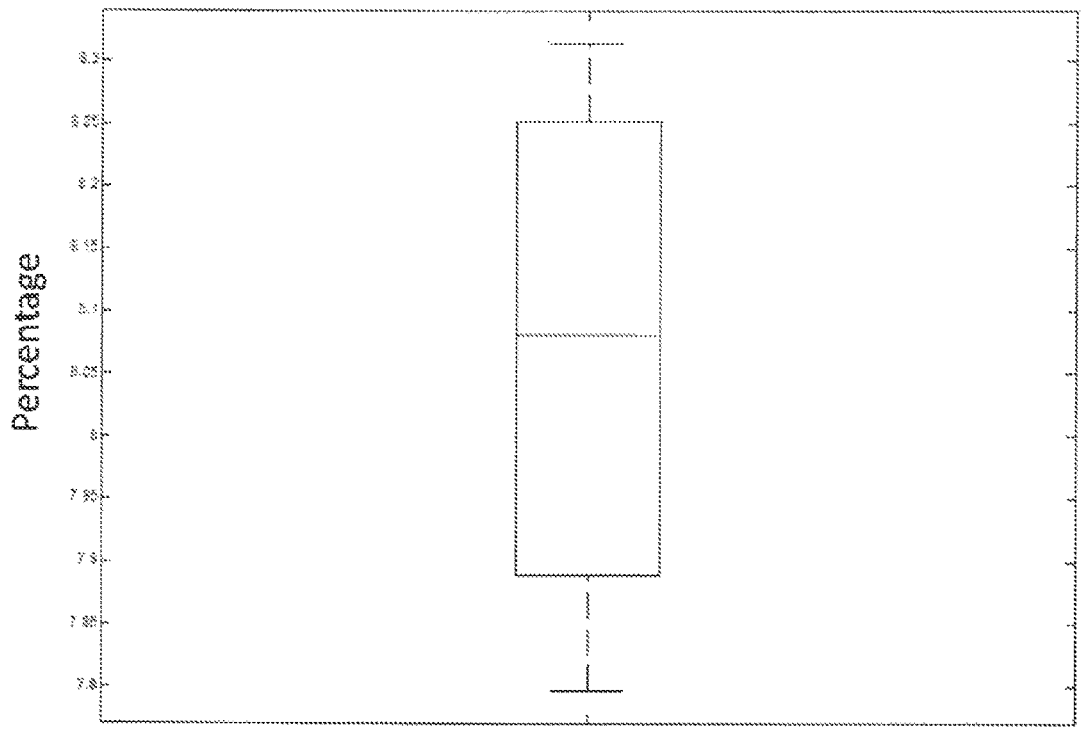

FIG. 4 provides an analysis of maximal influence of nuclear-encoded mitochondrial transcripts (Numts or pseudogenes) on reliable heteroplasmy detection sensitivity. The boxplot conveys the ratio of reads aligned to the mitochondrial DNA genome that might originate from Numt contamination across 9 samples captured with the 1:100 mtDNA:nuclear Mito-Plus Whole-Exome custom capture kit and sequenced one sample per flow-cell lane on the Illumina HiSeq 2000. The length of the box represents the 25th to 75th interquartile range, the interior horizontal line represents the median, and vertical lines issuing from the box extend to the minimum and maximum values of the analysis variable.

Figure 5:
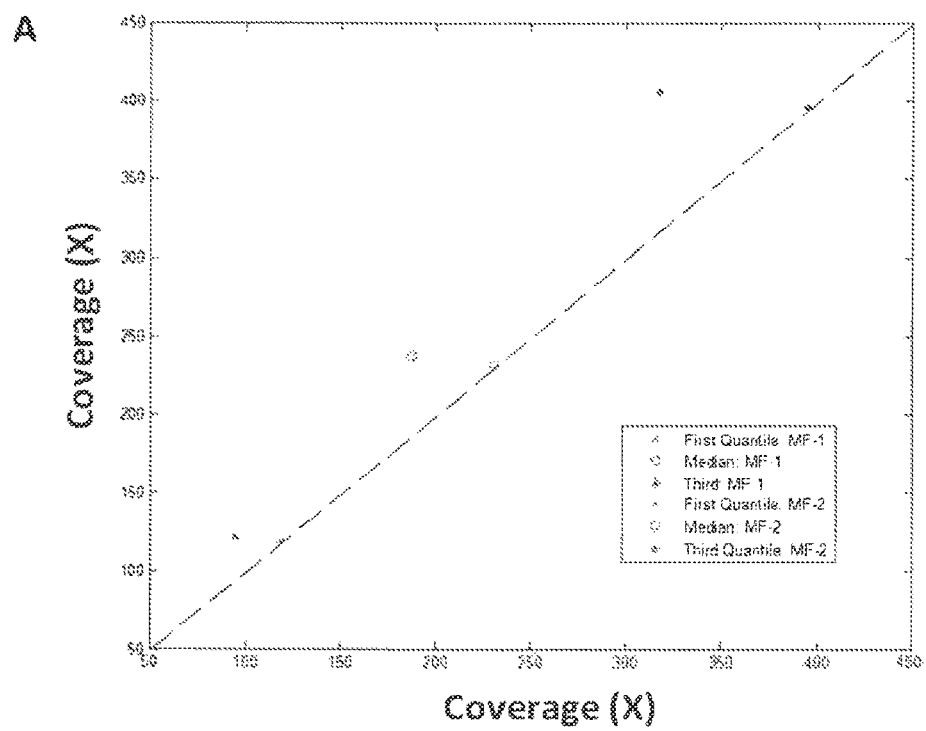
Figure 5:
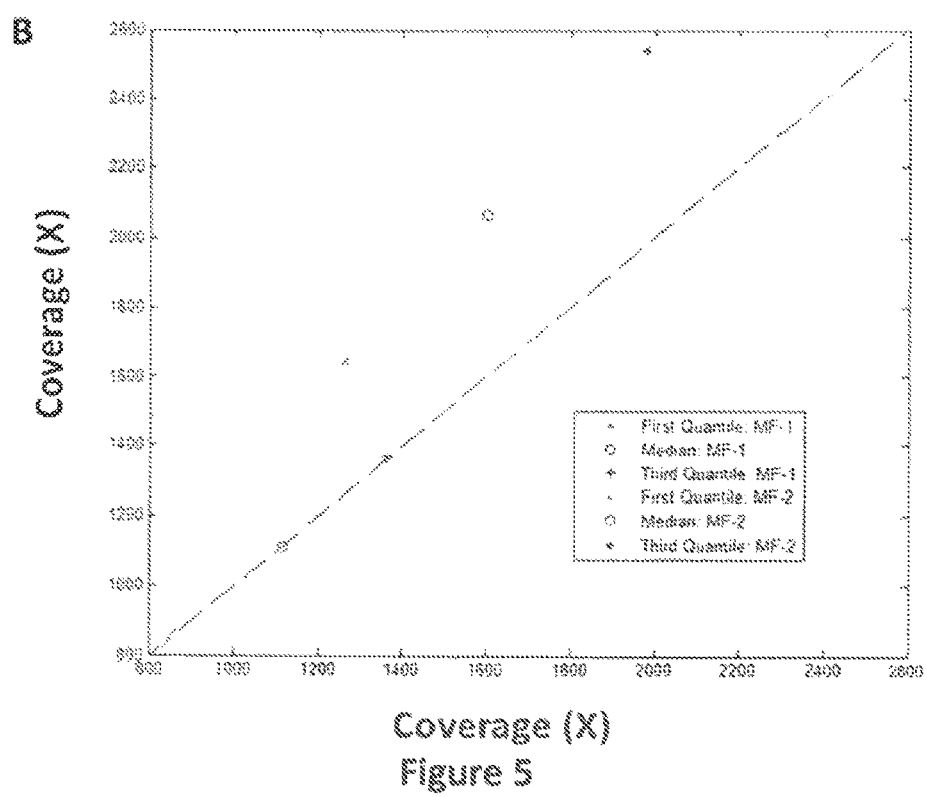

FIGS. 5A and 5B show that Mito-Plus Whole Exome capture reliably detects heteroplasmic mtDNA mutations. Coverage distribution statistics for replicate experiments for all targeted regions (FIG. 5A) and the whole mtDNA genome (FIG. 5B) are provided. MF-1 and MF-2 represent separate datasets from two flow-cell lanes run on blood DNA captured with the 1:500 and 1:1000 molar ratios of mtDNA:nDNA, respectively, from the same mitochondrial disease patient having a known mtDNA-encoded ND5 gene heteroplasmic mutation (m.13513G>A).

Figure 6A:
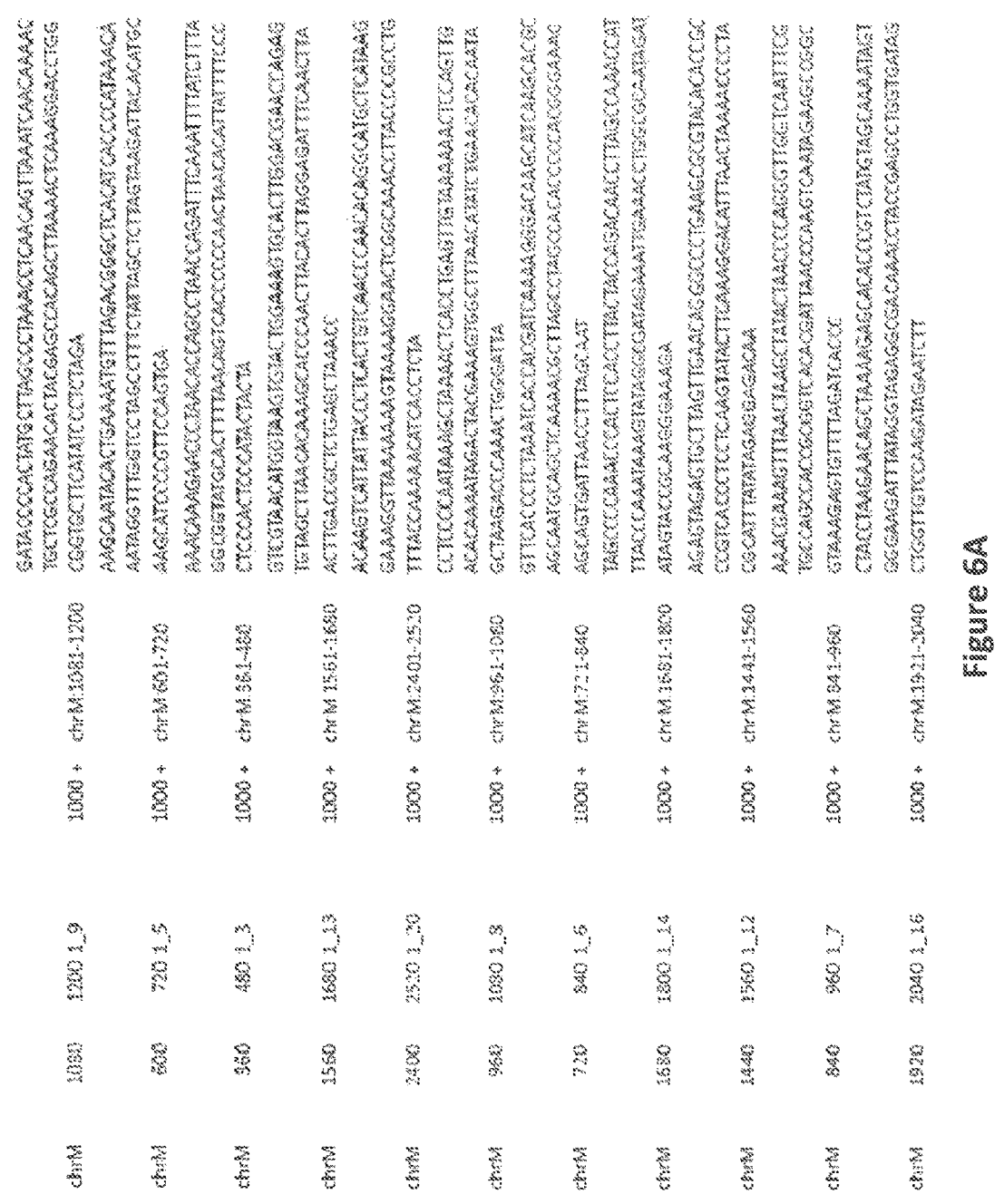
Figure 6B:
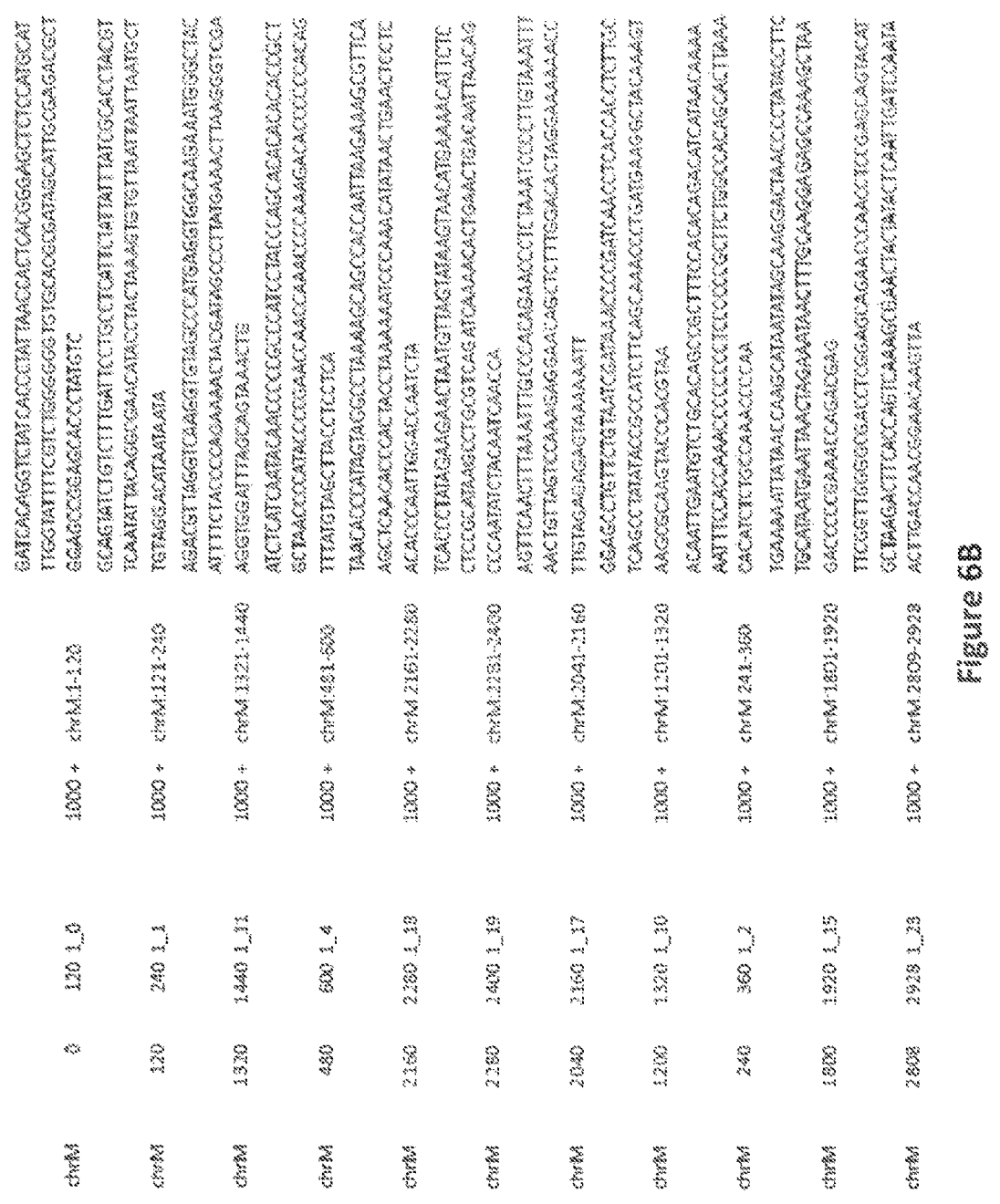
Figure 6D:
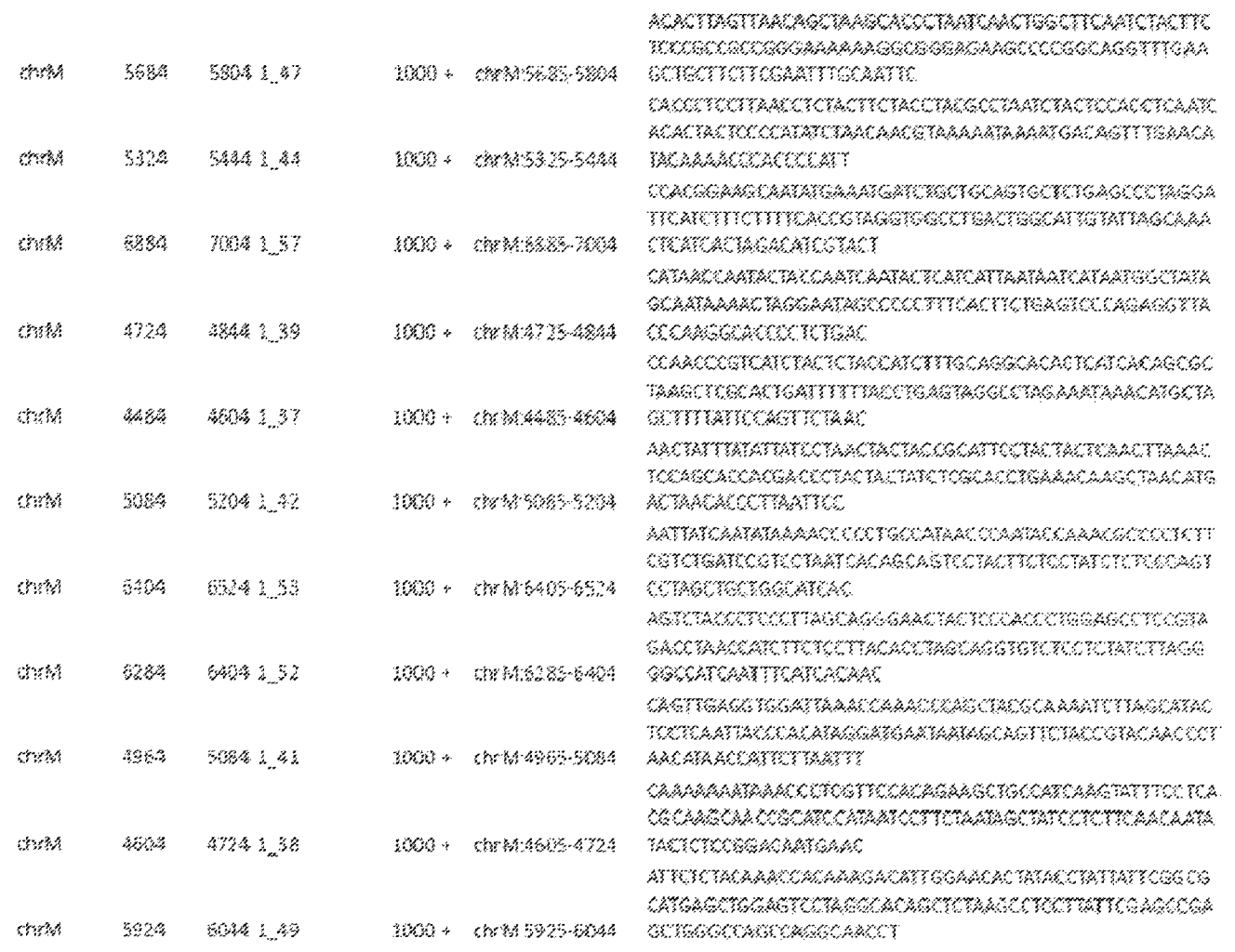
Figure 6E:
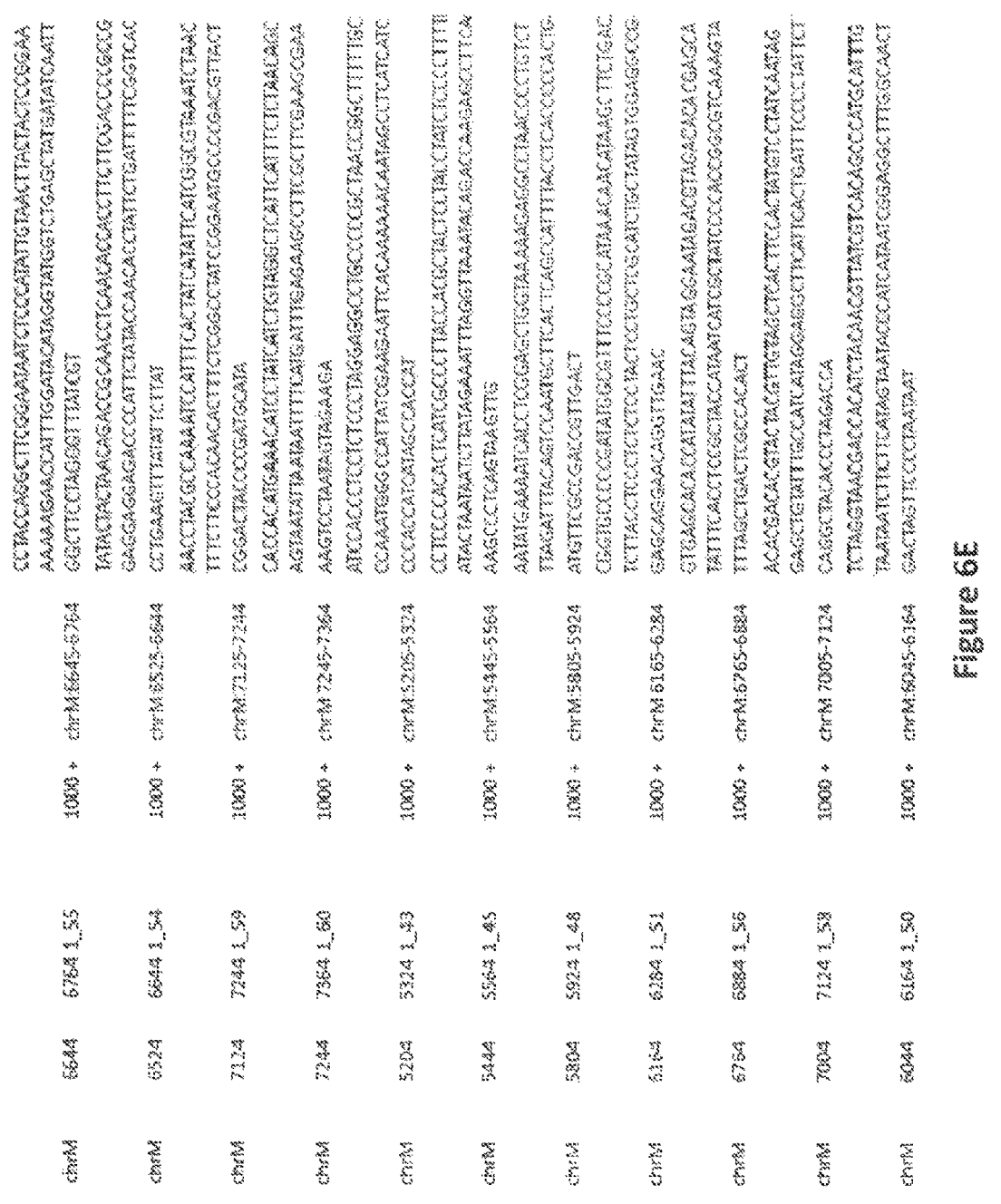
Figure 6F:
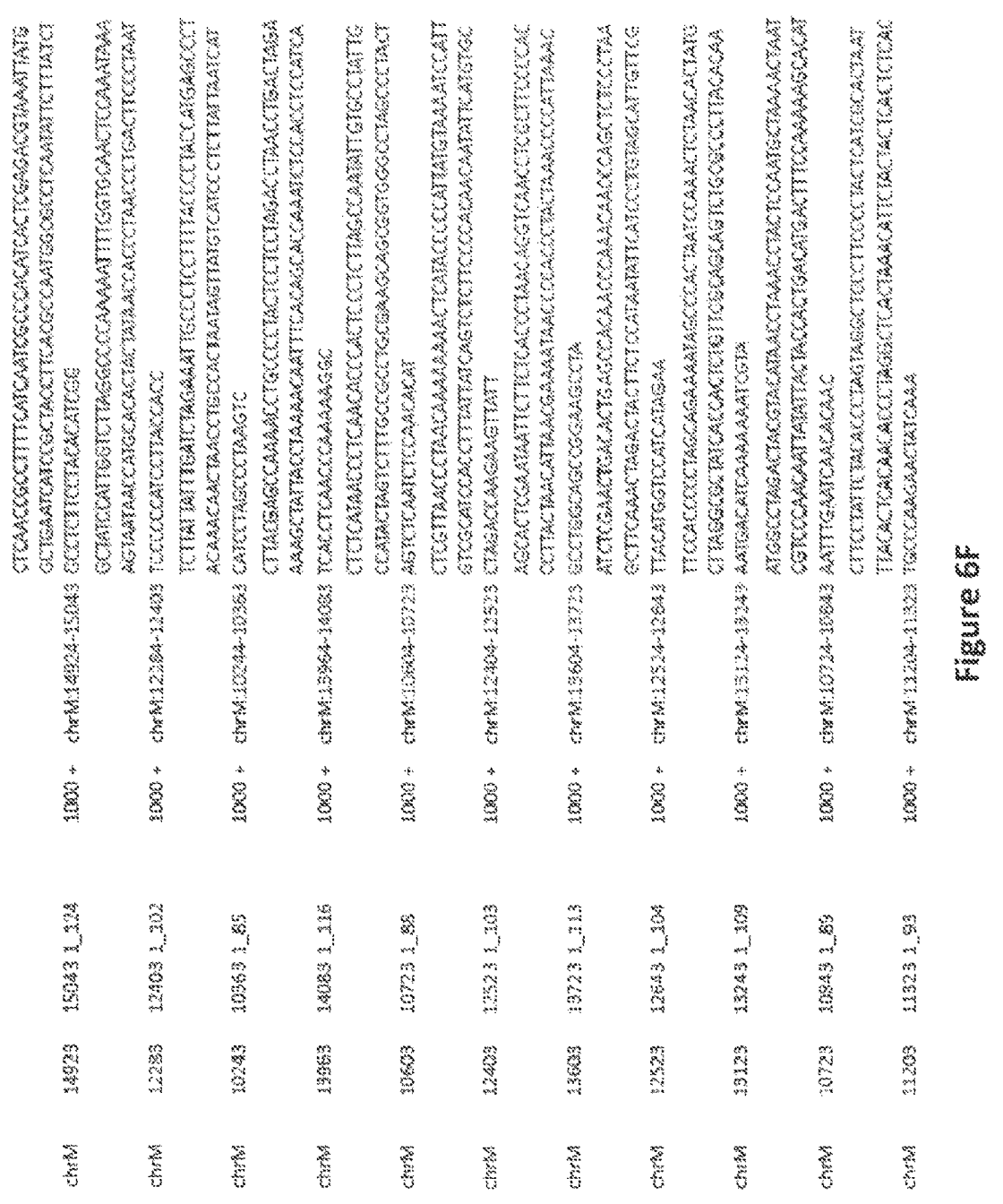
Figure 6G:
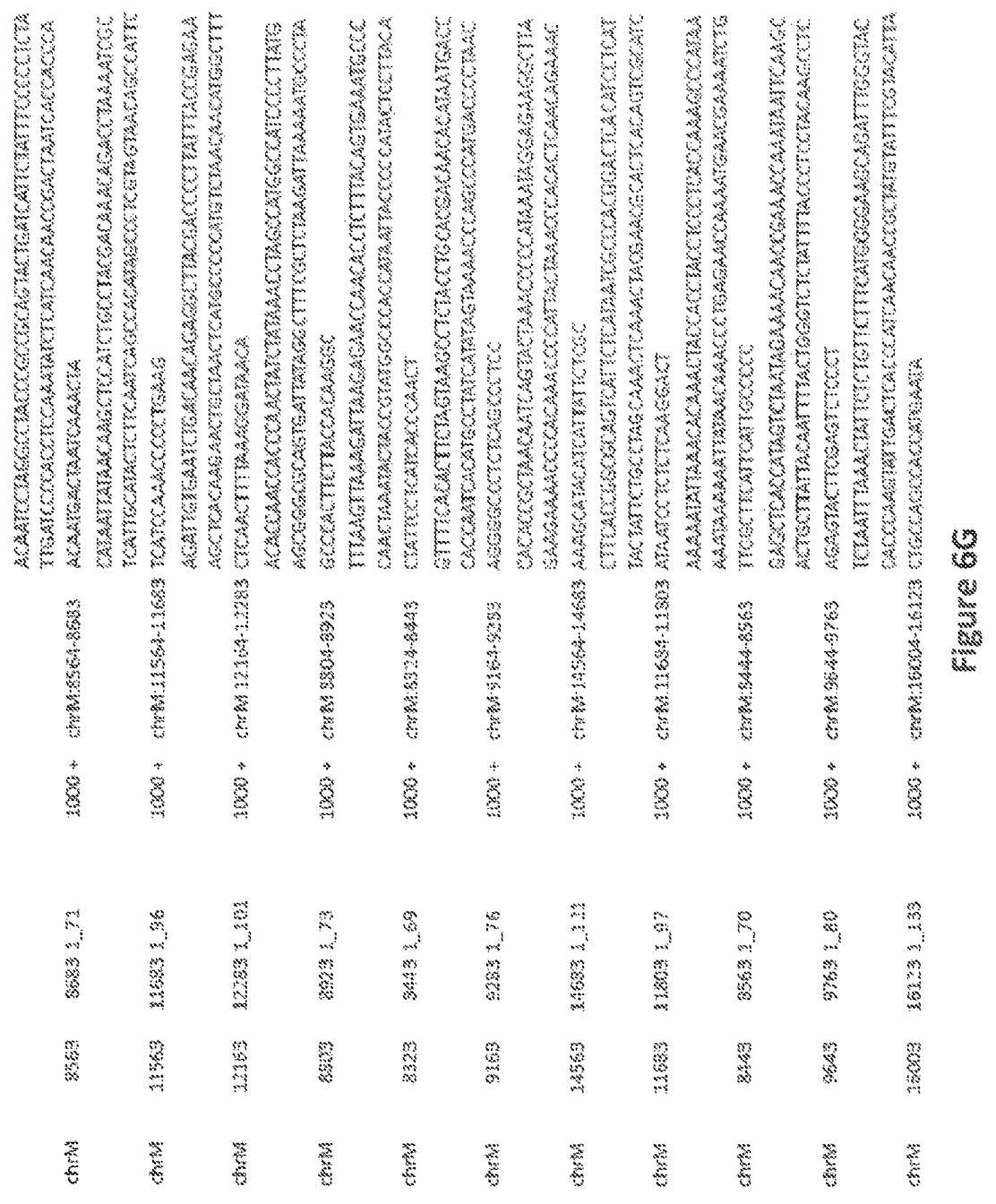
Figure 6H:
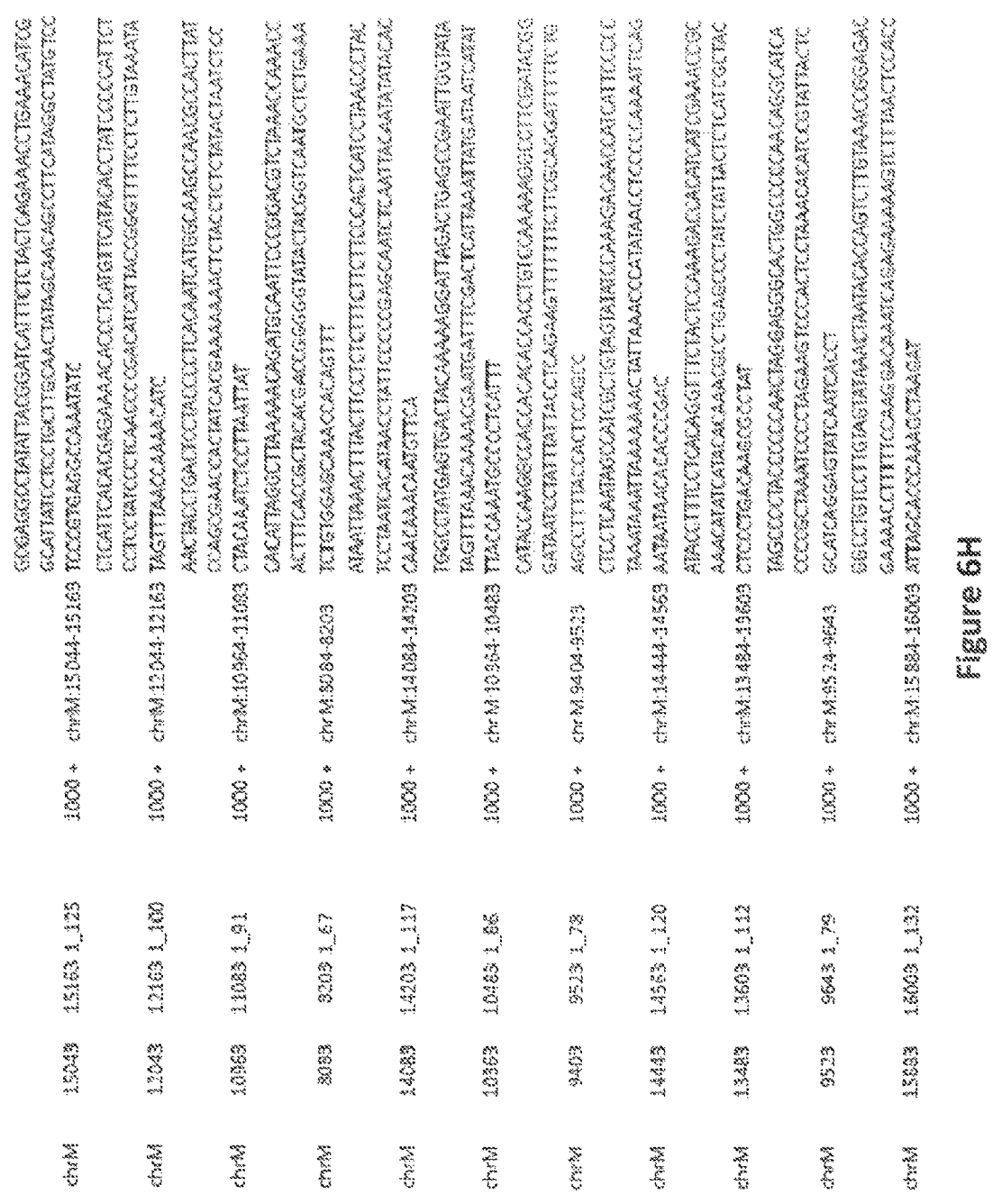
Figure 6I:
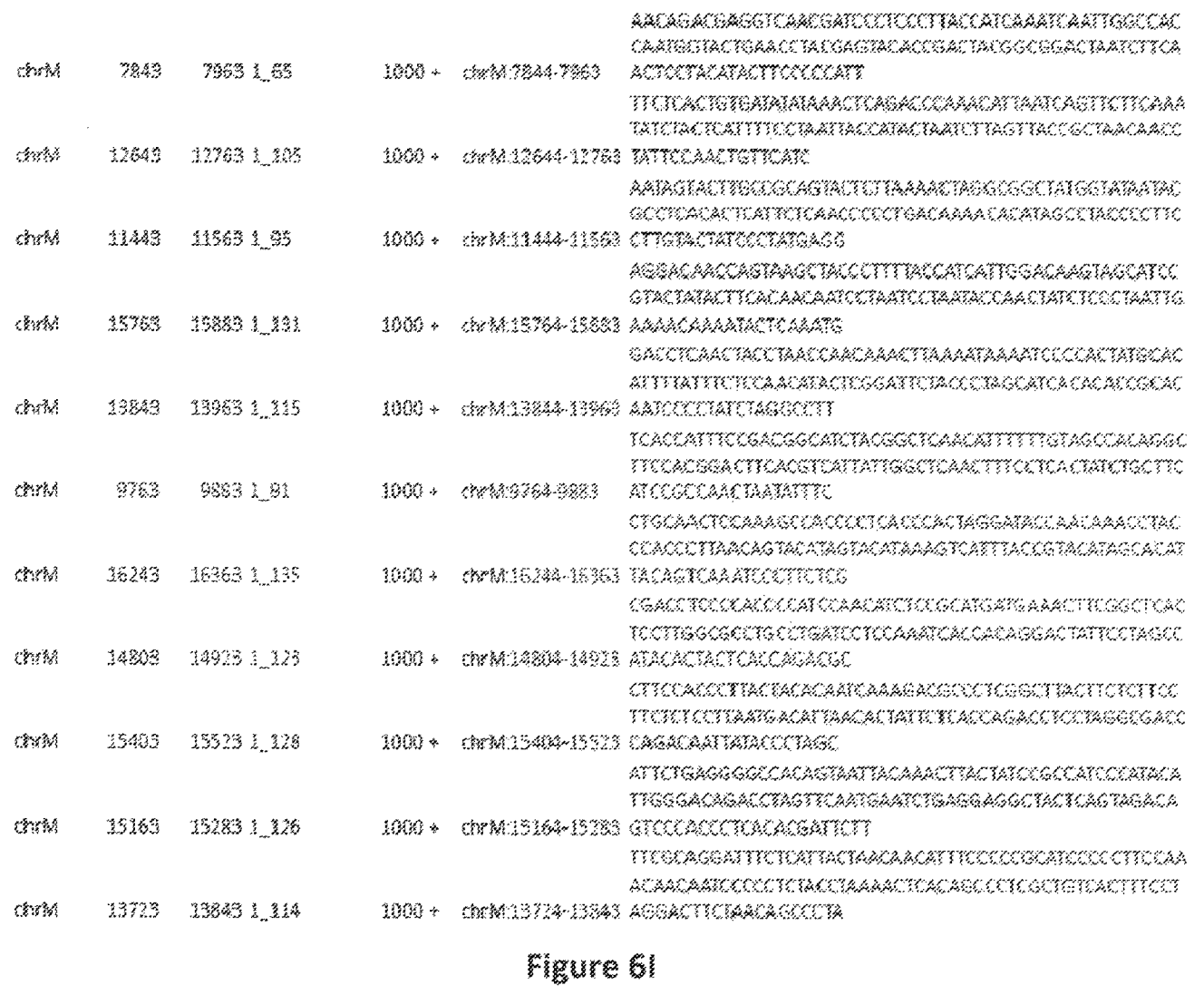
Figure 6J:
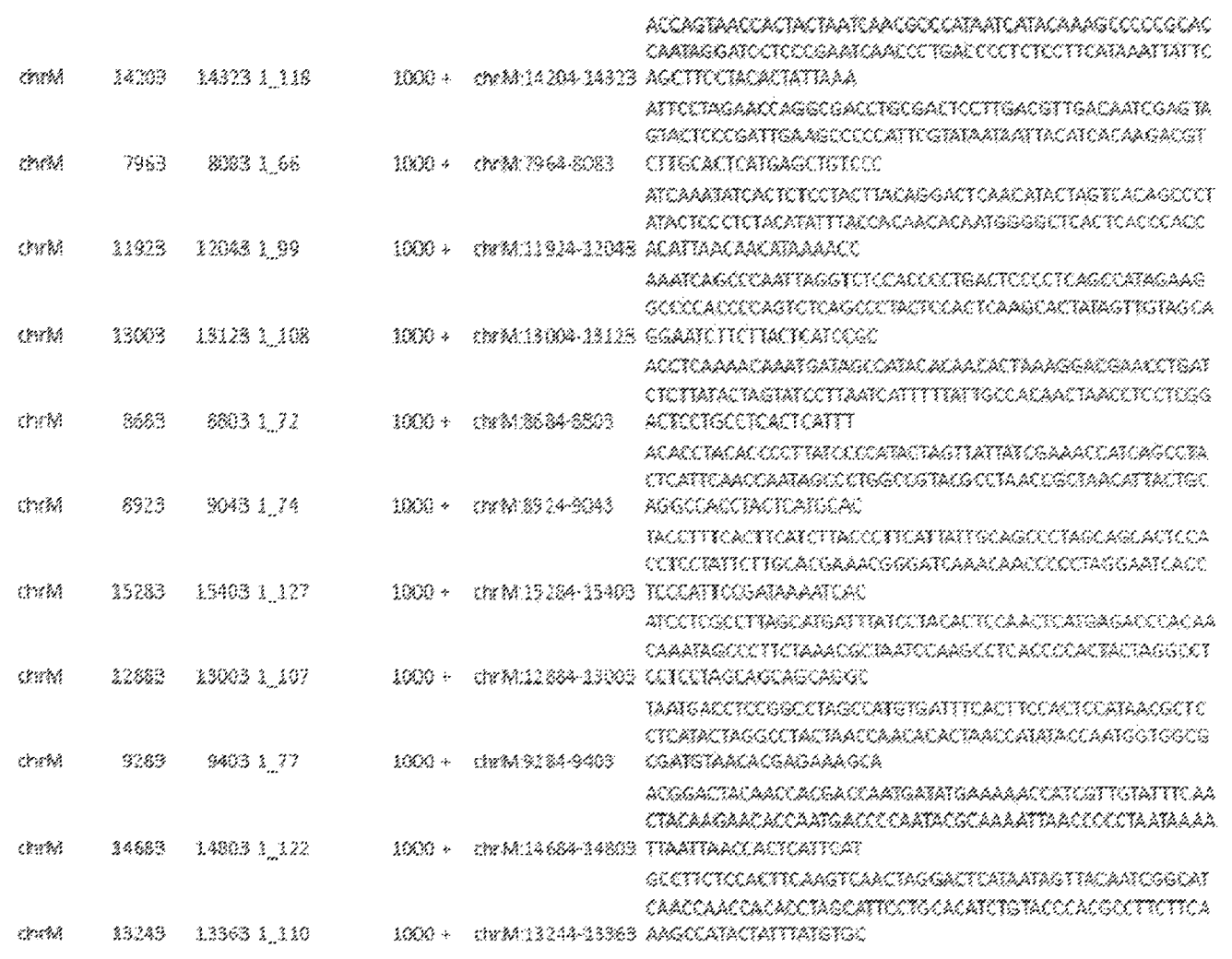
Figure 6K:
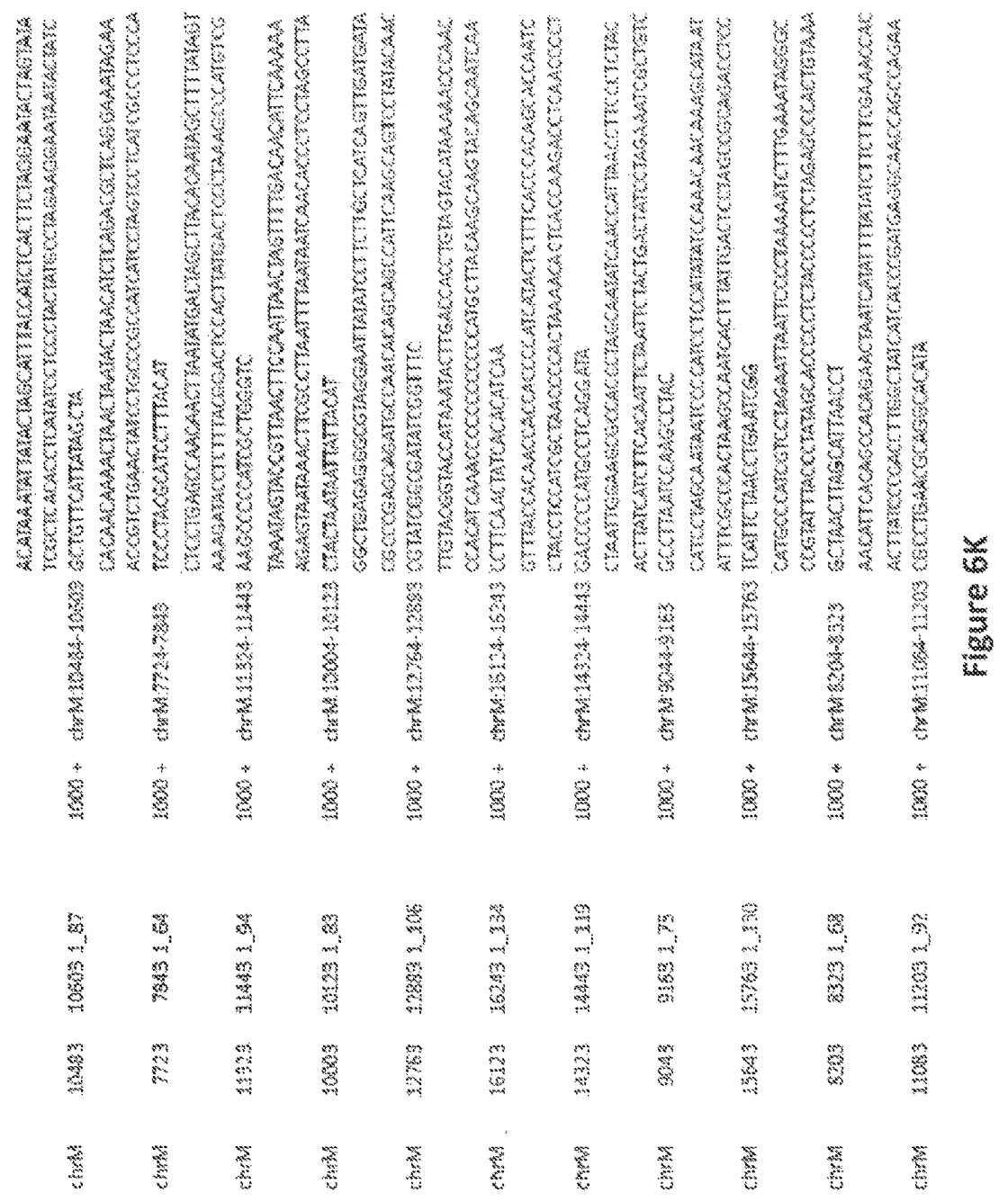
Figure 6L:
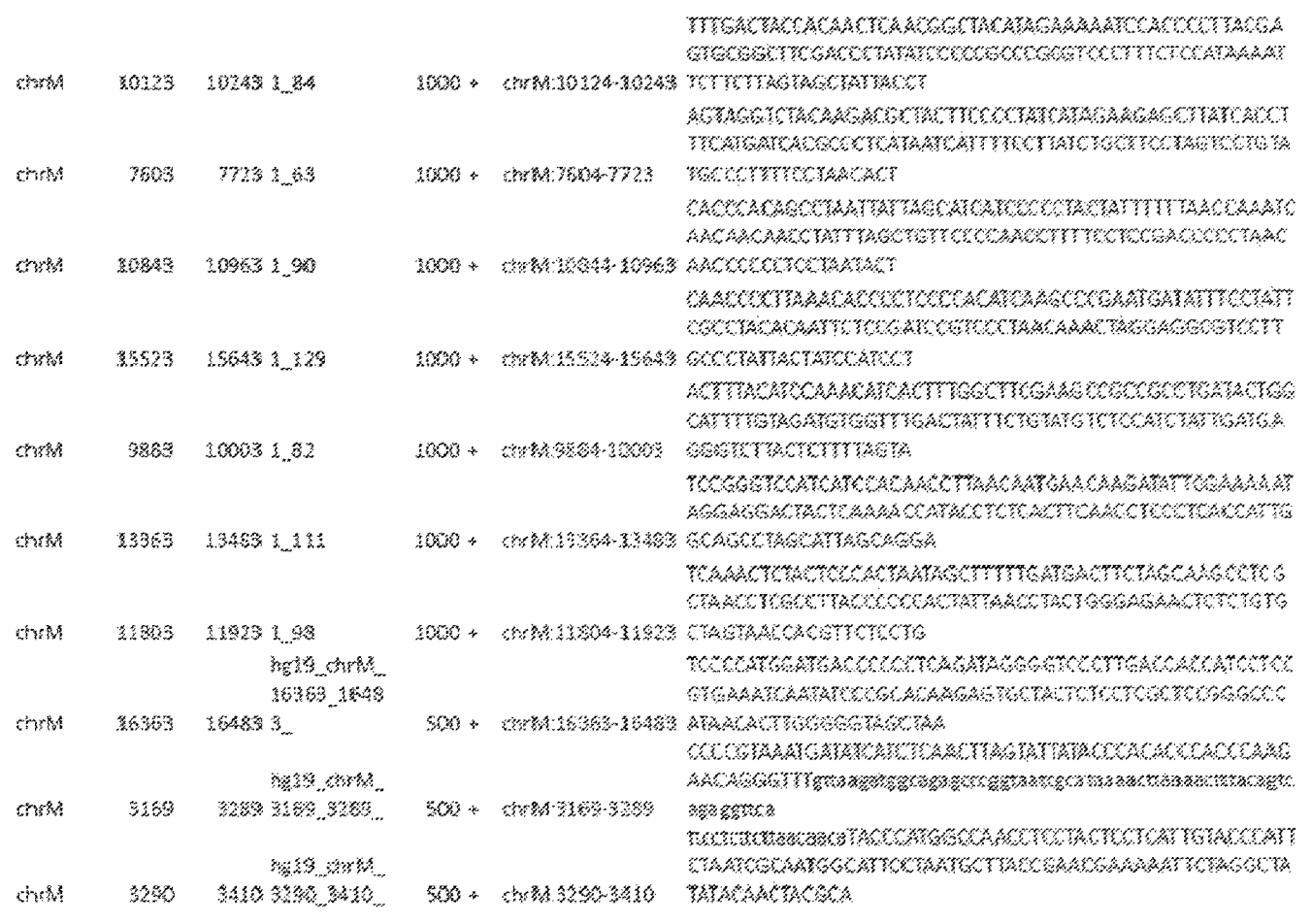

FIGS. 6A-6L provide the probe sequences targeting the entire mtDNA genome. Sequences provided are SEQ ID NOs: 1-131, from top to bottom.

FIG. 7 provides the coverage statistics for the entire whole-exome nuclear target regions for 9 samples captured with different mixes of custom library baits.

FIG. 8 shows the coverage performance for both the nuclear exome and mtDNA genome with varying molar ratios of custom baits for the mtDNA genome relative to the MitoCarta-optimized standard 50 Mb whole exome design. Nuclear exome coverage was preserved regardless of mtDNA:nDNA genome capture ratio, but the mtDNA genome median and high-depth (>1,000×) coverage began to fall off at molar ratios below 1:100. Data shown included all sequence reads. Following removal of duplicate sequencing reads, the mtDNA genome coverage fall-off was even more evident beginning at 1:200 molar ratio, where 1,000× coverage was only achieved for 93.29% of the mtDNA genome.

Figure 9:
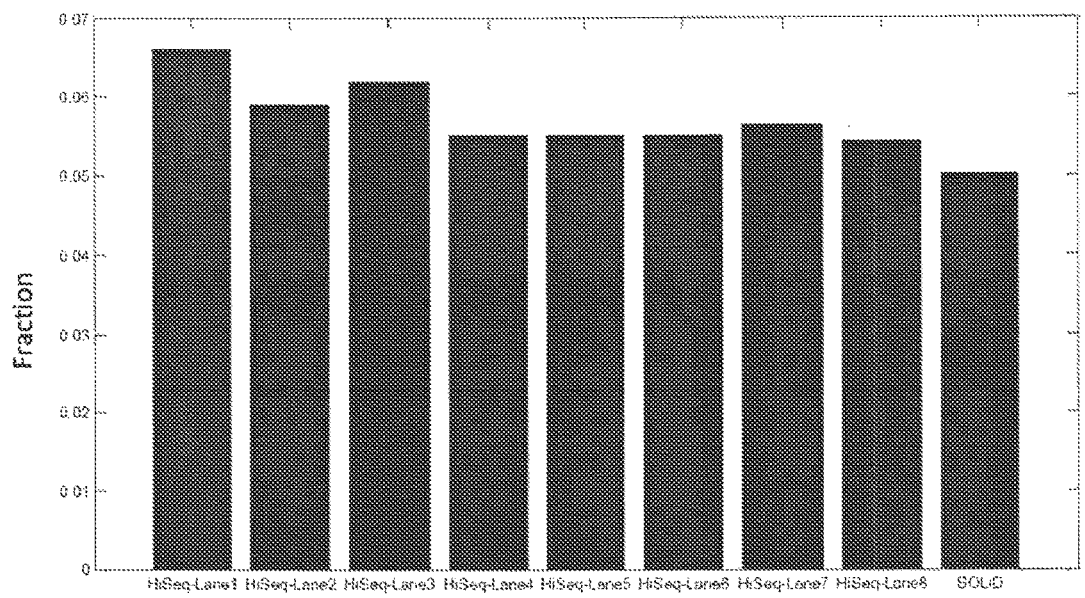

FIG. 9 provides a graph of the estimated sequencing error rate for HiSeq and SOLiD platforms based on concurrent analysis of the PhiX genome. Sequencing error rate is shown for each of the individual flow cell lanes on the Illumina HiSeq, as well as for the cumulative SOLiD dataset.

FIGS. 10A-10E provide the Mito 101 gene list and associated disorders. FIG. 10F provides the references cited in FIGS. 10A-10E.

DETAILED DESCRIPTION OF THE INVENTION

Discovering causative genetic variants in individual cases of suspected mitochondrial disease requires interrogation of both the mitochondrial (mtDNA) and nuclear genomes. Whole-exome sequencing can support simultaneous dual-genome analysis, although currently available capture kits do not target the mtDNA genome and provide insufficient capture for some nuclear-encoded mitochondrial genes. To optimize interrogation of nuclear and mtDNA genes relevant to mitochondrial biology and disease, a custom whole-exome library was formulated by blending RNA "baits" from three separate designs: (A) Agilent Technologies Sure-Select$^{XT}$ 50 Mb All Exon PLUS Targeted Enrichment Kit, (B) 16-gene nuclear panel targeting sequences for known MitoCarta proteins not included in the 50 Mb All Exon design, and (C) sequences targeting the entire mtDNA genome. The final custom formulations consisted of a 1:1 ratio of nuclear baits to which a 1 to 1,000-fold diluted ratio of mtDNA genome baits were blended. Patient sample capture libraries were paired-end sequenced on an Illumina HiSeq 2000 system using v3.0 SBS chemistry. mtDNA genome coverage varied depending on the mtDNA:nuclear blend ratio, where a 1:100 ratio provided optimal dual-genome coverage with 10× coverage for over 97.5% of all targeted nuclear regions and 1,000× coverage for 99.8% of the mtDNA genome. mtDNA mutations were reliably detected to at least an 8% heteroplasmy level, as discriminated both from sequencing errors and potential contamination from nuclear mtDNA transcripts (Numts). The "1:100 Mito-Plus Whole-Exome" Agilent capture kit offers an optimized tool for whole-exome analysis of nuclear and mtDNA genes relevant to the diagnostic evaluation of mitochondrial disease. This platform provides a one-stop whole-exome sequencing solution that can be applied to both research and clinical genetic diagnostic evaluations of individuals with suspected mitochondrial disease.

While mitochondrial diseases are relatively rare and many are poorly understood, the causes of certain mitochondrial diseases have been identified (see, e.g., FIG. 10). The cause of the mitochondrial diseases may be mutations in mitochondrial DNA or nuclear DNA. The instant invention provides an optimized tool for whole exome analysis of nuclear and mtDNA genes relevant to the diagnostic evaluation of mitochondrial disease. The library of the instant invention allows for simultaneous enrichment for subsequent next-generation sequencing based sequence analysis of MitoCarta nuclear genes and the entire mtDNA genome, as is highly relevant to the diagnostic evaluation of suspected mitochondrial disease. By being embedded in a whole-exome capture kit, this mitochondrial-optimized genomic analysis nevertheless retains the simultaneous opportunity for discovery both of phenotypically-overlapping disorders that may not directly involve the mitochondria as well as of novel disease genes. The data presented herein indicates that the custom "1:100 Mito-Plus Whole-Exome" design offers reliable mtDNA mutation heteroplasmy detection sensitivity together with the distinct advantage that no separate technical or analytic methodologies for mtDNA genome sequence analysis are required by the investigator at the time of sample processing for whole-exome analysis. This design allows for targeted enrichment of the whole-exome for sequence-based genetic diagnosis in both research and clinical diagnostic applications where the relevance of mtDNA is well-recognized, as well as in cases where the potential contributory role of mtDNA mutations may otherwise be overlooked.

In accordance with the instant invention, compositions comprising oligonucleotides which specifically hybridize with mitochondrial DNA are provided. The oligonucleotides may be RNA or DNA, particularly DNA. The oligonucleotides may be single-stranded or double-stranded. The oligonucleotides may also vary in length. For example, oligonucleotides of the instant invention may be about 10 to about 500 nucleotides in length, about 20 to about 250 nucleotides in length, or about 50 to about 200 nucleotides in length. The compositions may optionally comprise at least one carrier (e.g., a liquid buffer or aqueous solution). Alternatively, the oligonucleotides may be dried or lyophilized for re-suspension later. In a particular embodiment, the oligonucleotides of the instant invention are contained within a microarray or immobilized on a solid support.

In a particular embodiment, the composition comprises at least one oligonucleotide comprising a nucleic acid molecule in FIG. 6 (or oligonucleotides complementary to those in FIG. 6). The composition may comprise at least 10, 20, 30, 40, 50, 60, 70, 80, 90, 100, 110, 120, 130, or all of the nucleic acid molecules provided in FIG. 6. The oligonucleotides may comprise the sequences provided in FIG. 6, consist of the sequences provided in FIG. 6, or be a fragment of the sequences provided in FIG. 6 (e.g., a fragment of about 100 nucleotides in length). In a particular embodiment, the compositions of the instant invention comprise oligonucleotides with at least one variant of the sequences provided in FIG. 6. The variant may have at least 90%, 95%, 97%, or 99% homology (identity) with the sequence provided in FIG. 6.

The compositions of the instant invention may further comprise oligonucleotides that specifically hybridize with the nuclear genome. In a particular embodiment, the composition further comprises a genome library or a whole exome library (e.g., oligonucleotides that specifically hybridize with exons) such as the SureSelect 50 Mb Human All-Exon library. In a particular embodiment, the composition may further comprise oligonucleotides that specifically hybridize with MitoCarta gene sequences that are not included in the whole exome library. For example, the composition may further comprise oligonucleotides which specifically hybridize with at least 1, 2, 3, 4, 5, 6, 7, 8, 9, 10, 11, 12, 13, 14, 15, or all 16 of the following genes (inclusive of coding regions and UTRs): BCL2, GPX1, LYRM4, MSRB2, NDUFA11, NUDT8, PIGY, PRDX2, PRDX5, SLC25A26, TIMMI17B, ZBED5, C6orf136, HSD17B8, MRPS18B, and TAP1.

When the compositions of the instant invention comprise oligonucleotides that specifically hybridize with the nuclear genome or exome and oligonucleotides that specifically hybridize with mitochondrial DNA, the ratio of mitochondrial oligonucleotides to nuclear oligonucleotides can be varied. In a particular embodiment, the ratio of mitochondrial oligonucleotides to nuclear oligonucleotides ranges from about 10:1 to about 1:1000, about 1:1 to about 1:500, about 1:10 to about 1:250, about 1:50 to about 1:200, about 1:75 to about 1:150, about 1:90 to about 1:110, or about 1:100.

The oligonucleotides of the instant invention may also be contained in a kit. Within the kit, the mitochondrial oligonucleotides may be contained in a first composition and the nuclear oligonucleotides may be contained in a second composition. Alternatively, the kit may comprise a single composition comprising the mitochondrial oligonucleotides and, optionally, the nuclear oligonucleotides. The kit may further comprise instruction material, buffers, and/or containers.

The instant invention also provides methods of diagnosing and/or determining the susceptibility to/risk and/or providing a prognosis for a mitochondrial disease in a subject (e.g., mammal, human). FIG. 10 provides examples of various mitochondrial diseases/disorders and the causative genetic mutation. The methods of the invention may comprise sequencing the nucleic acid molecules in a biological sample obtained from the subject by obtaining or isolating nucleic acid molecules from the biological sample with the oligonucleotides of the instant invention, amplifying the nucleic acid molecules, and determining the presence or absence of mutation associated with a mitochondrial disease in the amplified DNA. The methods of the invention may comprise sequencing the nucleic acid molecules in a biological sample obtained from the subject by performing PCR with the oligonucleotides of the instant invention and determining the presence or absence of mutation associated with a mitochondrial disease in the amplified DNA.

In addition to the above, the instant invention also encompasses methods for identifying mutations associated with a mitochondrial disease or disorder. In a particular embodiment, the method comprises sequencing the nucleic acid molecules of a biological sample as described above, wherein a mutation in a nucleic acid molecule compared to wild-type is indicative of a mutation associated with a mitochondrial disease or disorder. In a particular embodiment, a population of biological sample from more than one subject with the mitochondrial disease or disorder is assayed in the method.

Definitions

The following definitions are provided to facilitate an understanding of the present invention:

The singular forms "a," "an," and "the" include plural referents unless the context clearly dictates otherwise.

As used herein, a "biological sample" refers to a sample of biological material obtained from a subject, preferably a human subject, including a tissue, a tissue sample, a cell sample, a tumor sample, and a biological fluid (e.g., blood, urine, or amniotic fluid). In a particular embodiment, the biological sample is blood.

As used herein, "diagnose" refers to detecting and identifying a disease or disorder in a subject. The term may also encompass assessing or evaluating the disease or disorder status (progression, regression, stabilization, response to treatment, etc.) in a patient known to have the disease or disorder.

As used herein, the term "prognosis" refers to providing information regarding the impact of the presence of a disease or disorder (e.g., as determined by the diagnostic methods of the present invention) on a subject's future health (e.g., expected morbidity or mortality, the likelihood of getting diabetes, and the risk of cardiovascular disease). In other words, the term "prognosis" refers to providing a prediction of the probable course and outcome of a disease/disorder or the likelihood of recovery from the disease/disorder.

The term "treat" as used herein refers to any type of treatment that imparts a benefit to a patient afflicted with a disease or disorder, including improvement in the condition of the patient (e.g., in one or more symptoms), delay in the progression of the condition, etc.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains about 10-500, about 10-250, about 10-100, about 10-50, about 15-30, about 15-25, about 20-50, or more nucleotides, although it may contain fewer nucleotides. The probes herein may be selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target, although they may. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically about 10-25 or more nucleotides in length, but can be significantly longer. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989, Molecular Cloning: A Laboratory Manual, Cold Spring Harbor Laboratory Press):

$$Tm=81.5° C.+16.6 \text{ Log } [Na+]+0.41(\% G+C)-0.63(\% \text{ formamide})-600/\#bp \text{ in duplex}$$

As an illustration of the above formula, using [Na+]= [0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12 20° C. below the Tm of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 μg/ml denatured salmon sperm DNA at 42° C., and washed in 0.1×SSC and 0.5% SDS at 65° C. for 15 minutes.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers.

As used herein, an "instructional material" includes a publication, a recording, a diagram, or any other medium of expression which can be used to communicate the usefulness of the composition of the invention for performing a method of the invention.

The phrase "solid support" refers to any solid surface including, without limitation, any chip (for example, silica-based, glass, or gold chip), glass slide, membrane, plate, bead, solid particle (for example, agarose, sepharose, polystyrene or magnetic bead), column (or column material), test tube, or microtiter dish.

As used herein, the term "array" refers to an ordered arrangement of hybridizable array elements (e.g., proteins, nucleic acids, antibodies, etc.). The array elements are arranged so that there are at least one or more different array elements on a solid support. In a particular embodiment, the array elements comprise oligonucleotide probes. In a particular embodiment, the arrays comprise up to about 50, up to about 100, up to about 500, up to 1000, up to about 5,000, up to 10,000, up to 50,000, up to 100,000 or more nucleic acid molecules/probes (e.g., to unique nucleic acid targets).

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, excipient, auxilliary agent or vehicle with which an active agent of the present invention is administered. Carriers can be sterile liquids, such as water and oils, including those of petroleum, animal, vegetable or synthetic origin, such as peanut oil, soybean oil, mineral oil, sesame oil and the like. Other examples of liquid carriers include aqueous saline solutions and aqueous dextrose and glycerol solutions. Suitable pharmaceutical carriers are described in "Remington's Pharmaceutical Sciences" by E. W. Martin (e.g., Remington's Pharmaceutical Sciences (Mack Publishing Co., Easton, Pa.)) and "Remington: The Science and Practice of Pharmacy" (Ed. Troy; Lippincott Williams & Wilkins, Baltimore, Md.).

The following example provides illustrative methods of practicing the instant invention, and is not intended to limit the scope of the invention in any way.

EXAMPLE

Materials and Methods mtDNA Genome Bait and Blend Design.

Sequences targeting the entire mtDNA genome were created in eArray (Agilent Technologies) by standard 1× tiling across the target hg19 mitochondrial loci. These baits for "Design C" (mtDNA genome) were factory-blended into the nuclear baits at either equimolar ratio or reduced concentration by 10, 50, 100, 200, 500, or 1000-fold less than the nuclear baits. The accession number for the Agilent mtDNA genome design bait library was ELID #320851 (earray.chem.agilent.com/earray).

Nuclear Mitochondrial Gene Set Optimization.

Bioinformatics analysis of the SureSelect$^{XT}$ 50 Mb All Exon PLUS Targeted Enrichment Kit was performed to determine the exon level coverage of 1,034 known mitochondria-localized "Human MitoCarta" genes (Pagliarini et al. (2008) Cell 134:112-123). Baits were designed for 16 of these nuclear genes shown to have less than 80% of their exons covered (ELID #329521) (earray.chem.agilent.com/earray). These baits were factory-added in equimolar ratio to the SureSelectXT 50 Mb All Exon PLUS Targeted Enrichment (Agilent part number 5190-2867).

Exome Sequencing.

Targeted enrichment was performed using Agilent Technologies SureSelect$^{XT}$ 50 Mb All Exon PLUS Targeted Enrichment Kit that included custom mitochondrial genome content in varying mitochondrial:nuclear capture bait molar ratios, namely: Blend A—1:1; Blend B—1:10; Blend C—1:50; Blend D—1:100; Blend E—1:200; Blend F—1:500; Blend G—1:1000. Patient sample capture libraries were prepared as described in the kit manual, and were 2×101 base pair paired-end sequenced on an Illumina (San Diego, Calif.) HiSeq 2000 Next-Generation Sequencing system using v3.0 SBS chemistry with average flow-cell lane cluster densities of ~700-800 K/mm$^2$. One sample was analyzed per flow-cell lane to obtain a minimum 10× read depth of ~96% for the targeted nuclear exome. The mitochondrial genome coverage varied depending on the mitochondrial:nuclear blend ratio.

Exome Data Analyses.

Burrows-Wheeler Aligner (BWA) (version 0.5.9-r16) was used to align the sequence reads to the human reference genome GRCh37 downloaded from the 1000 Genomes Project website (www.1000genomes.org/). Samtools (version 0.1.12 or r859) was used to remove potential duplicates (with rmdup command), and make initial single nucleotide polymorphism (SNP) and indel calls (with pileup command). A custom program was developed and used to further refine the SNP and indel calls. The custom program uses a false discovery rate approach to adjust raw base counts at a candidate position after Benjamini and Hochberg correction based on quality values of all bases. A coverage depth cutoff of 10× is then applied. Depth of coverage is calculated based on the alignment file using samtools.

Sequencing Error Estimation Using PhiX Phage Genome.

BWA (version 0.5.9-r16) was used to align HiSeq sequence reads to the PhiX phage genome (NC_001422.1) downloaded from NCBI. BioScope was used at default settings to align SOLiD sequence data. Samtools was applied to remove duplicates and obtain the number of high quality base reads for different strands and alternative bases at a given base position. Sequencing error rate was estimated as the sum of the number of bases different from the consensus call made by Samtools over the depth of coverage at a given base position.

Results

Agilent SureSelect 50 Mb Standard Whole-Exome Capture Kit Provides Insufficient Coverage for the mtDNA Genome and all MitoCarta Genes.

The target regions of the Agilent SureSelect 50 Mb whole-exome capture kit ("50 Mb kit") do not include the mtDNA genome, as no probes specifically capture mtDNA. Although off-target capture from this platform does provide some mtDNA genome coverage, this is of questionable specificity and is insufficient to permit reliable sequence analysis across the entirety of the mtDNA genome. An in silico comparison of 50 Mb kit target regions with the reference sequence gene set (NCBI RefSeq) revealed that among the 1,034 MitoCarta genes there were 12 nuclear genes (BCL2, GPX1, LYRM4, MSRB2, NDUFA11, NUDT8, PIGY, PRDX2, PRDX5, SLC25A26, TIMMI17B, ZBED5) that had less than 80% of their exonic regions covered by the target regions of the 50 Mb kit. Lack of coverage for these genes was empirically confirmed by analysis of 8 exomes captured with the standard 50 Mb kit that were sequenced in a single sample per flow-cell lane on the Illumina HiSeq 2000 (FIG. 1A). The average whole-exome coverage for each sample ranged from 159.7× to 351.8×, with 98.0% to 99.1% of all target regions covered at least 1×. By comparison, the 12 MitoCarta genes in question had not only a lower average depth of coverage (range: 69.8×-170.9×) but also a markedly lower percentage of exonic regions that were covered at least 1× (range: 78.4% to 84.9%) (FIG. 1B). Experimental evidence demonstrated that lack of sequence coverage for these 12 MitoCarta nuclear genes was even more pronounced at the standard 10× and 20× depth-of-coverage cutoffs that are typically used for variant calling purposes.

SureSelect Custom Probe Design to Optimize Coverage of the mtDNA Genome and all MitoCarta Genes.

A custom SureSelect "Mito-Plus Whole-Exome" library was generated by blending RNA "baits" from 3 separate designs: (A) standard SureSelect 50 Mb Human All-Exon product that targets the nuclear exome, (B) a 16-gene panel targeting MitoCarta gene sequences that were not included in the All-Exon design, and (C) sequences targeting the entire mtDNA genome (FIG. 6). Designs B and C were created in eArray by 2× tiling across target nuclear genes or 1× tiling across the target hg19 mtDNA genome loci, respectively. Baits having significant overlap with Repeat-Masker regions were excluded. For Design B, new nuclear genome baits targeted 416 additional coding regions and 186 UTRs in total for the 12 MitoCarta genes that were suboptimally targeted by the 50 Mb kit (BCL2, GPX1, LYRM4, MSRB2, NDUFA11, NUDT8, PIGY, PRDX2, PRDX5, SLC25A26, TIMMI17B, ZBED5), as well as exonic regions of 4 other MitoCarta nuclear genes present on alternative genome assemblies (C6orf136, HSD17B8, MRPS18B, TAP1) (bait details available upon request). The 3 different designs were factory blended in varying molar ratios of Designs A plus B to Design C, as detailed below, for purposes of optimizing dual genome capture of mitochondrial genes.

Experimental Evaluation of the Optimal Capture Ratio of mtDNA to Nuclear Baits.

All final custom formulations consisted of a 1:1 ratio of nuclear baits from Design A (All-Exon) to Design B (16 MitoCarta genes). Given the 1-2 log natural excess of mtDNA genomes to the nuclear genome, the optimal output of nuclear versus mtDNA genome sequences that retained the ability to detect low-level mtDNA variant heteroplasmy was sought. Therefore, a range of seven molar concentrations of all nuclear baits (Designs A plus B) to Design C (mtDNA genome) baits was experimentally evaluated. Design C (mtDNA genome) baits were blended in at either an equimolar ratio or reduced concentrations of 10, 50, 100, 200, 500, or 1000-fold less than the nuclear baits. Subsequently, 9 randomly selected human blood DNA samples were selected for capturing each by one of these 7 different molar ratios (labeled from A to G to indicate 1:1, 1:10, 1:50, 1:100, 1:200, 1:500, and 1:1000), a 1:1 ratio of Design A to Design B (with no mtDNA genome baits added), or the standard 50 Mb kit (FIG. 7). The 9 captured DNA samples were then sequenced in a single flow-cell lane for each sample on the Illumina HiSeq 2000. Optimal coverage across the entire nuclear exome target regions was achieved for each of the 9 samples regardless of the mtDNA:nDNA molar ratio (FIG. 2A and FIG. 7). Specifically, 99.0% to 99.4% of whole-exome nuclear target regions were covered at least 1×, with 96.0% to 98.1% of whole-exome nuclear target regions covered at least 10× (FIG. 8). Even at an equimolar ratio of 1:1 mtDNA:nuclear exome capture, the overall performance statistics for nuclear exome sequence coverage did not differ either in median coverage or in percentage of target regions covered at 1×, 10×, or 20× relative to either the standard 50 Mb kit alone or combined with the Design B (MitoCarta gene) nuclear probes.

Similarly, the standard 50 Mb kit that contained no mtDNA baits still provided some mtDNA genome coverage, which was 100% at 1× coverage and 99.99% at 10× coverage (FIG. 2B). This off-target mtDNA capture is explained by the greater natural abundance in terms of molar ratio of mtDNA to nuclear DNA. Nonetheless, such non-targeted coverage is obviously random, non-uniform, drops significantly upon analysis of 100× coverage performance, and has a minimum coverage depth of 0 to 2 reads at some mtDNA genome bases. Whereas 10× to 20× median coverage is generally acceptable for analysis of nuclear exome capture performance, a substantially higher-depth of coverage across the entire mtDNA genome is critical to permit reliable detection of low-level mtDNA variant heteroplasmy. Mixing mtDNA genome baits with nuclear baits at all 7 different ratios, from equimolar to 1 mtDNA to 1000 nDNA, all provided much improved coverage across the entire mtDNA genome. Specifically, the standard 50 Mb kit had a median 109× and mean of 133.5×mtDNA genome coverage. However, careful data analysis suggested that the optimal mtDNA:nuclear molar ratio was 1:100, where over 99.9% of the mtDNA genome was covered at least 100×, over 99.8% of the mtDNA genome was covered at least 1000×, the median coverage was 7,918×, and the minimum depth of coverage for any mtDNA base was 41×. Higher molar ratios (1:1, 1:10, 1:50) provided similar if not better mtDNA coverage as seen with 1:100, but these higher molar ratios carry the potential cost of reducing sequencing bandwidth in the nuclear target regions. Lower molar ratios (1:200, 1:500, 1:1000) demonstrated a progressive fall-off in mtDNA genome coverage, which for the 1:200 ratio was an mtDNA genome median coverage of 4,497× with only 99.1% of the mtDNA genome covered to a depth of 1000×. Therefore, a 1:100 mtDNA to nuclear molar ratio was selected for subsequent experiments.

A 1:100 Molar Ratio of mtDNA to Nuclear Baits Provided Optimal Coverage for Both the Nuclear Target Regions and the mtDNA Genome.

Custom libraries with 1:100 molar ratio of mtDNA to nuclear baits were used to capture 11 exomes from human blood genomic DNA and then sequenced using one HiSeq 2000 flow-cell lane per sample, with coverage statistics summarized in FIG. 3A. Although capture experiments did not work as well for two samples (61p2 and 79) as they did for the other 9 samples, 1× coverage of the nuclear exome was seen for 98.4% to 99.7% of target regions for each of the 11 samples tested. Excluding the two samples that had suboptimal performance, an average of 194× to 415× mean depth of coverage for the nuclear exome was achieved for the remaining 9 samples. Optimal mtDNA genome coverage was achieved for all 11 samples (FIG. 3B), which was 99.99% to 100% of mtDNA genome bases covered at both 1×  and 10×, 99.89% to 100% of mtDNA genome bases covered at 100× coverage, and 93.75% to 99.95% of mtDNA genome bases covered at 1000× for all samples. When excluding the two samples that had had suboptimal overall nuclear and mtDNA capture performance (61p2 and 79), 1000× coverage was seen at 99.6% to 99.95% of all mtDNA genome bases in each of the remaining 9 samples captured at the 1:100 mtDNA to nuclear molar ratio.

All MitoCarta Nuclear Genes are Well-Covered by the SureSelect Custom 1:100 "Mito-Plus Whole-Exome" Capture Kit.

Given the relevance of the MitoCarta nuclear gene list to candidate gene analysis in the diagnostic evaluation of suspected mitochondrial disease, it was examined how well the exonic regions of 1,034 MitoCarta genes were covered on the custom 1:100 "Mito-Plus Whole Exome" capture kit. In this analysis, all exonic regions of these 1,034 MitoCarta genes were looked at, rather than just the targeted exonic regions for which new baits had been designed. At least 97.9% of exonic regions for all Mitocarta genes were covered at least 1× when including the two samples (61p2 and 79) that had generally suboptimal coverage (FIG. 3B), while more than 99.1% of exonic regions for all MitoCarta genes had 1× coverage in each of the 9 samples that had good overall performance. Improved coverage was also evident for the 12 MitoCarta genes whose exons were not sufficiently covered by the 50 Mb kit design (not including the 4 genes for which baits were added for exons present on alternative assemblies), with 96.8% to 100% of all exonic regions of these genes covered at least 1× in all 11 samples (FIG. 3B). Excluding the two relatively poor-performing samples (61p2 and 79), 10× coverage was achieved for 96.8% to 98.1%, and at least 20× coverage was achieved for 95.6% to 97.5%, of the exonic regions of these 12 MitoCarta genes. Thus, these data demonstrate the improved utility of this custom capture kit for whole-exome nuclear gene sequence analysis that includes all known mitochondrial-localized proteins (MitoCarta subset) in suspected mitochondrial disease.

Since an important potential use of this custom capture platform would be in the clinical diagnostic setting to provide focused sequencing of all known mitochondrial disease genes (rather than all mitochondrial-localized proteins), the performance of the custom kit to cover 101 known mitochondrial disease genes that are currently sequenced on a clinical diagnostic basis was assessed using next generation sequencing (NGS) by a Mito 101 Mitochondrial Disease Nuclear Gene Panel (GeneDx). All 11 samples had at least 1× coverage across 98.17% to 99.93% of these 101 genes. Upon exclusion of the two problematic samples (61p2 and 79), 10× coverage was achieved for 97.44% to 98.76%, and at least 20× coverage for 94.35% to 98.02%, in each of the remaining 9 samples for these 101 known mitochondrial disease genes. Future work could focus on assessing patterns of specific nucleotide bases that might be systematically missed by current probes that are captured by design of additional probes to achieve improved capture of all possible bases in currently known, and newly recognized, mitochondrial disease genes. In addition, the same custom Design B (MitoCarta genes) and Design C (mtDNA genome) probes that were designed can be added with no alteration in expected coverage performance to the recently released v4.0 Agilent whole-exome kit, which targets the same genomic regions as the standard 50 Mb All-Exon design but is rebalanced to provide more even coverage across the 50 Mb nuclear exome (www.genomics.agilent.com).

mtDNA Genome Heteroplasmy Detection.

Sensitive detection of low-level heteroplasmic mtDNA mutations is critical to the diagnostic evaluation of suspected mitochondrial disease. While the historic "gold-standard" methodology of mtDNA genome analysis by PCR amplification and Sanger sequencing has a lower detection limit ranging between 30-50% heteroplasmy, it is widely recognized that disease may result from lower heteroplasmy levels for some pathogenic mutations that might only be detectable with alternative molecular biology methods such as ARMS (allele refractory mutation system) qPCR (Wang et al. (2011) Curr. Protoc. Hum. Genet., Chapter 19:Unit 19.16). Further, since heteroplasmy levels can vary between tissues in a given patient, it is desirable to achieve sensitive and reproducible detection of potential heteroplasmic mutations that are at low level in blood to avoid pursuit of invasive tissue biopsies to obtain skeletal muscle or liver in which the mutation level might be enriched. For these reasons, NGS has emerged as the preferred molecular method for mtDNA genome analysis in the clinical diagnostic setting. However, NGS-based mtDNA genome analysis is not currently available in a single platform together with whole-exome nuclear gene analysis, but must be separately considered as a potential etiology in a given patient.

To permit low-level heteroplasmy detection, it is necessary to achieve a very high depth of coverage for the mtDNA genome. However, it is important to recognize that the lower bound of sensitivity for heteroplasmy detection is inherently dependent on several platform-specific parameters including sequencing quality and error rate. For example, with an average base quality (Q) score of 30, heteroplasmy as low as 0.1% can be detected when the base is covered to a depth of coverage over 1000×. When the average base Q score is reduced to 20, heteroplasmy levels as low as 1% can still theoretically be detected, although the true heteroplasmy sensitivity is limited by various sequencing platform-specific errors and alignment errors. It is also compounded by the multiple testing problem facing all genomic sequencing applications, including whole exome sequencing. As an example, exome sequencing might reveal reads with variant bases aligned at hundreds of thousands genomic positions, even though the number of coding variants per individual is expected to be around 20,000. It was, therefore, sought to experimentally determine the true heteroplasmy sensitivity of the Mito-Plus whole exome capture design.

Sequencing platform-specific error rates directly influence the likelihood that a given mtDNA variant detected in only a small fraction of the NGS reads represents true heteroplasmy versus a sequencing-related error. The PhiX phage genome provides a robust means by which to estimate alignment errors due to its genome's simplicity and no concern for potential heteroplasmic sites. Analysis of the PhiX genome that were spiked into the Illumina HiSeq 2000 runs of Agilent Mito-Plus Whole Exome captured nuclear and mtDNA revealed a sequencing error rate of 5.79%+ 0.42%. This sequencing error is similar to the approximately 5% error rate previously observed when analyzing the PhiX genome that was simultaneously sequenced on the SOLiD 3.0 NGS sequencing platform of the mtDNA genome (see FIG. 1), where the mtDNA genome was amplified by the same two long-range PCR reactions as are used for Affymetrix MitoChip v2.0 analysis (Maitra et al. (2004) Genome Res., 14:812-819; Xie et al. (2011) BMC Bioinformatics 12:402). Thus, Illumina HiSeq 2000 and SOLiD 3.0 technologies have similar rates of sequencing error rates in the 5-6% range, which represents the estimated lower bound of being able to confidently discern truly heteroplasmic mtDNA mutations from machine-generated sequencing error. Thus, low-levels of heteroplasmic mtDNA mutations can be reliably detected following different capture and sequencing technologies, but only to the limit determined by the platform-specific sequencing error rate.

mtDNA heteroplasmy detection sensitivity by NGS is further complicated by the existence of pseudogenes in the nuclear genome that are non-functional but share strong sequence similarity with mtDNA genes (Li et al. (2012) Nucleic Acids Res., 40:e137; Li et al. (2012) Genome Biol., 13:R34). These mtDNA pseudogenes are evolutionary remnants that result from transfer of cytoplasmic mitochondrial DNA sequences into the separate nuclear genome of a eukaryotic organism and are collectively referred to as "nuclear mitochondrial DNA transcripts" (Numt) (Mishmar et al. (2004) Hum. Mutat., 23:125-133). The analytic challenge is that an apparently heteroplasmic mtDNA mutation might instead represent off-target Numt capture that was subsequently aligned to the mtDNA genome because of the strong sequence similarities between mtDNA genes and Numts. To understand the potential influence of Numt on heteroplasmy detection sensitivity, the maximum likelihood that a seemingly heteroplasmic mutation was contaminated by a Numt was estimated. All reads from each sample were first aligned to a reference that includes all known Numts (details available upon request), as well as the mtDNA genome. The number of reads that aligned to the mtDNA genome were counted. All reads were next aligned only to the Numts. The percentage of reads that aligned to the mtDNA genome when the Numts reference was included that can also be aligned to Numts when the mtDNA genome reference is absent provides the upper-bound estimate of the percentage of sequencing reads that align to mtDNA genome but could potentially have originated from Numt contamination. This analysis was performed for 9 randomly selected samples captured by the custom 1:100 mtDNA to nuclear whole-exome capture kit and each sequenced on one HiSeq 2000 flow-cell lane. In all 9 samples, the upper bound of Numt contribution to heteroplasmy sensitivity detection ranged from 7.80% to 8.31% (8.10+0.18%) (FIG. 4). Based on this observation, it can be concluded with greater than 99.9% confidence that an observed heteroplasmic mutation is not from Numt contaminations if it is present in at least 8.64% of sequence reads. However, this is a very conservative estimate since it does not take into account the fact that mtDNA outnumbers nuclear DNA by 1-2 log orders of magnitude (Li et al. (2012) Nucleic Acids Res., 40:e137; Li et al. (2012) Genome Biol., 13:R34). Thus, the true lower bound for mtDNA heteroplasmy detection sensitivity is likely much lower than 8%. Still, even 8% heteroplasmy detection sensitivity already represents great improvement over the 30% to 50% lower bound for mtDNA heteroplasmy detection that is achieved by the "gold-standard" of Sanger sequencing. More importantly, 8% falls below the level of heteroplasmy for a pathogenic mtDNA mutation that is generally likely to cause clinical manifestations of classic mitochondrial disease. While alternative mtDNA capture approaches such as long-range PCR may provide even greater heteroplasmy sensitivity, and even permit large deletion detection by NGS analysis (Zhang et al. (2012) Clin. Chem., 58:1322-1331), these data demonstrate that the Agilent custom "1:100 Mito-Plus Whole-Exome" kit offers good heteroplasmy detection sensitivity together with the distinct advantage that no separate technical or analytic methodologies for mtDNA genome sequence analysis are required at the time of sample processing for whole-exome analysis.

Technical Reproducibility.

The technical reproducibility of the custom "Mito-Plus whole-exome" kit to capture both nuclear exome targets and the mtDNA genome was examined. Two capture libraries were separately prepared using the 1:500 (sample "MF1") and 1:1000 (sample "MF2") blend of mtDNA genome to whole-exome design using blood genomic DNA from the same mitochondrial disease patient. Each library was further split into two, differentially bar-coded, and then sequenced in separate HiSeq 2000 flow-cell lanes. Therefore, this data set provides technical replicates both at the library preparation and sequencing levels. Highly reproducible coverage statistics was obtained. Overall short reads alignment characterizations/traits were strongly correlated among technical replicates for all target regions (FIG. 5A) and specifically for the mtDNA genome (FIG. 5B), as correlation coefficients for both analyses were approximately 1.

In addition, this sample was used to assess the technical reproducibility of heteroplasmic mtDNA mutation detection by this platform since the sample was shown by Sanger-based sequencing to harbor a 30% heteroplasmic G to A transition mutation at position 13513 of the mt-ND5 gene. The mt-ND5 heteroplasmic mutation was present at a level of 65.0% (723 A/1112 total reads) in the MF1-1 data set, at a level of 64.9% (803 A/1238 total reads) in the MF1-2 data set, at a level of 63.4% (393 A/620 total reads) in the MF2-1 data set, and at a level of 64.8% (411 A/634 total reads) in the MF2-2 data set. Thus, heteroplasmy level determination from the mtDNA sequence data generated is highly reproducible, and likely more accurate than traditional Sanger sequencing, as is consistent with the growing recognition that NGS is becoming the new "gold-standard" for mtDNA heteroplasmy detection over Sanger sequencing (Zhang et al., 2012).

Biological Discovery.

The 11 exomes from human blood genomic DNA that were sequenced following capture with the custom "1:100 Mito-Plus Whole-Exome" design were from probands and family members in 4 unrelated mitochondrial disease families (FIG. 3A). Ideal coverage was achieved for most of these samples across both nuclear exome and mitochondrial genomes (FIG. 3A). This allows exclusion of mtDNA mutations as the disease cause for each family, while focusing on the identification of mutations in nuclear genes as strong novel disease gene candidates in these mitochondrial disease families.

A custom "1:100 Mito-Plus Whole-Exome" Agilent capture kit has been developed that allows simultaneous enrichment for subsequent NGS-based sequence analysis of all currently known nuclear MitoCarta genes and the entire mtDNA genome, as is highly relevant to the diagnostic evaluation of suspected mitochondrial disease. By being embedded in a whole-exome capture kit, this mitochondrial-optimized analysis nevertheless retains the simultaneous opportunity for discovery both of phenotypically-overlapping disorders that may not directly involve the mitochondria as well as of novel disease genes. Further, the data supports that the custom "1:100 Mito-Plus Whole-Exome" design offers reliable mtDNA mutation heteroplasmy detection sensitivity together with the distinct advantage that no separate technical or analytic methodologies for mtDNA genome sequence analysis are required by the investigator at the time of sample processing for whole-exome analysis. Thus, this design holds value for providing targeted enrichment of the whole-exome for sequence-based genetic diagnosis in both research and clinical diagnostic applications where the relevance of mtDNA is well-recognized, as well as in cases where the potential contributory role of mtDNA mutations may otherwise be overlooked. Future utilization of this capture approach in larger sample sizes will allow the ultimate efficiency of making novel discoveries of pathogenic mutations in both mtDNA and the nuclear exome to be determined over time.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A microarray comprising oligonucleotides immobilized on a solid support, wherein said oligonucleotides specifically hybridize with the nuclear genome and at least one oligonucleotide that specifically hybridizes with mitochondrial DNA, wherein said oligonucleotide that specifically hybridizes with mitochondrial DNA comprises a nucleic acid molecule in FIG. 6,
wherein said oligonucleotides are covalently attached to said solid support.

2. The microarray of claim 1, wherein said oligonucleotides that specifically hybridize with the nuclear genome comprise a whole exome library.

3. The microarray of claim 1, comprising at least 100 of the nucleic acid molecules provided in FIG. 6.

4. The microarray of claim 1, comprising all of the nucleic acid molecules provided in FIG. 6.

5. The microarray of claim 1, comprising oligonucleotides that specifically hybridize with MitoCarta gene sequences.

6. The microarray of claim 5, wherein said microarray comprises oligonucleotides that specifically hybridize with at least one gene selected from the group consisting of BCL2, GPX1, LYRM4, MSRB2, NDUFA11, NUDT8, PIGY, PRDX2, PRDX5, SLC25A26, TIMMI17B, ZBED5, C6orf136, HSD17B8, MRPS18B, and TAP1.

7. The microarray of claim 1, wherein ratio of oligonucleotides which specifically hybridize with mitochondrial DNA to oligonucleotides which specifically hybridize with the nuclear genome is about 1:75 to about 1:150.

8. The microarray of claim 7, wherein said oligonucleotides are about 20 to about 250 nucleotides in length.

9. The microarray of claim 7, wherein said ratio is about 1:100.

10. The microarray of claim 9, wherein said oligonucleotides are about 20 to about 250 nucleotides in length.

11. The microarray of claim 1, wherein said oligonucleotides are about 20 to about 250 nucleotides in length.

12. The microarray of claim 1, wherein said microarray comprises an oligonucleotide comprising SEQ ID NO: 1.

13. The microarray of claim 12, wherein said oligonucleotides are about 20 to about 250 nucleotides in length.

14. A microarray comprising at least one oligonucleotide that specifically hybridizes with mitochondrial DNA, wherein said oligonucleotide comprises a nucleic acid molecule in FIG. 6,
wherein said oligonucleotides are covalently attached to a solid support,
wherein said oligonucleotides are less than 200 nucleotides in length.

15. The microarray of claim 14, comprising at least 100 of the nucleic acid molecules provided in FIG. 6.

16. The microarray of claim 14, comprising all of the nucleic acid molecules provided in FIG. 6.

17. The microarray of claim 14, comprising oligonucleotides that specifically hybridize with MitoCarta gene sequences.

18. The microarray of claim 17, wherein said microarray comprises oligonucleotides that specifically hybridize with at least one gene selected from the group consisting of BCL2, GPX1, LYRM4, MSRB2, NDUFA11, NUDT8, PIGY, PRDX2, PRDX5, SLC25A26, TIMMI17B, ZBED5, C6orf136, HSD17B8, MRPS18B, and TAP1.

19. The microarray of claim 14, wherein said microarray comprises an oligonucleotide comprising SEQ ID NO: 1.

* * * * *

SEQUENCE LISTING

```
<160> NUMBER OF SEQ ID NOS: 131

<210> SEQ ID NO 1
<211> LENGTH: 120
<212> TYPE: DNA
<213> ORGANISM: Artificial Sequence
<220> FEATURE:
<223> OTHER INFORMATION: Probe

<400> SEQUENCE: 1 gatacccac tatgcttagc cctaaacctc aacagttaaa tcaacaaaac tgctcgccag      60
aacactacga gccacagctt aaaactcaaa ggacctggcg gtgcttcata tccctctaga    120

<210> SEQ ID NO 2
<211> LENGTH: 120
<212> TYPE: DNA
<213> ORGANISM: Artificial Sequence
<220> FEATURE:
<223> OTHER INFORMATION: Probe

<400> SEQUENCE: 2
aagcaataca ctgaaaatgt ttagacgggc tcacatcacc ccataaacaa ataggtttgg     60
tcctagcctt tctattagct cttagtaaga ttacacatgc aagcatcccc gttccagtga    120

<210> SEQ ID NO 3
<211> LENGTH: 120
<212> TYPE: DNA
<213> ORGANISM: Artificial Sequence
<220> FEATURE:
<223> OTHER INFORMATION: Probe

<400> SEQUENCE: 3
aaacaaagaa ccctaacacc agcctaacca gatttcaaat tttatcttta ggcggtatgc     60
acttttaaca gtcacccccc aactaacaca ttatttcccc ctcccactcc catactacta   120

<210> SEQ ID NO 4
<211> LENGTH: 120
<212> TYPE: DNA
<213> ORGANISM: Artificial Sequence
<220> FEATURE:
<223> OTHER INFORMATION: Probe

<400> SEQUENCE: 4
gtcgtaacat ggtaagtgta ctggaaagtg cacttggacg aaccagagtg tagcttaaca     60
caaagcaccc aacttacact taggagattt caacttaact tgaccgctct gagctaaacc   120

<210> SEQ ID NO 5
<211> LENGTH: 120
<212> TYPE: DNA
<213> ORGANISM: Artificial Sequence
<220> FEATURE:
<223> OTHER INFORMATION: Probe

<400> SEQUENCE: 5
acaagtcatt attaccctca ctgtcaaccc aacacaggca tgctcataag gaaaggttaa     60
aaaaagtaaa aggaactcgg caaaccttac cccgcctgtt taccaaaaac atcacctcta   120
```

<210> SEQ ID NO 6
<211> LENGTH: 120
<212> TYPE: DNA
<213> ORGANISM: Artificial Sequence
<220> FEATURE:
<223> OTHER INFORMATION: Probe

<400> SEQUENCE: 6 cctcccaat aaagctaaaa ctcacctgag ttgtaaaaaa ctccagttga cacaaaatag        60
actacgaaag tggctttaac atatctgaac acacaatagc taagacccaa actgggatta      120

<210> SEQ ID NO 7
<211> LENGTH: 120
<212> TYPE: DNA
<213> ORGANISM: Artificial Sequence
<220> FEATURE:
<223> OTHER INFORMATION: Probe

<400> SEQUENCE: 7
gttcaccctc taaatcacca cgatcaaaag ggacaagcat caagcacgca gcaatgcagc        60
tcaaaacgct tagcctagcc acccccac gggaaacagc agtgattaac ctttagcaat        120

<210> SEQ ID NO 8
<211> LENGTH: 120
<212> TYPE: DNA
<213> ORGANISM: Artificial Sequence
<220> FEATURE:
<223> OTHER INFORMATION: Probe

<400> SEQUENCE: 8
tagccccaaa cccactccac cttactacca gacaacctta gccaaaccat ttacccaaat       60
aaagtatagg cgatagaaat tgaaacctgg cgcaatagat atagtaccgc aagggaaaga     120

<210> SEQ ID NO 9
<211> LENGTH: 120
<212> TYPE: DNA
<213> ORGANISM: Artificial Sequence
<220> FEATURE:
<223> OTHER INFORMATION: Probe

<400> SEQUENCE: 9
agagtagagt gcttagttga acagggccct gaagcgcgta cacaccgccc gtcaccctcc      60
tcaagtatac ttcaaaggac atttaactaa aaccccctacg catttatata gaggagacaa    120

<210> SEQ ID NO 10
<211> LENGTH: 120
<212> TYPE: DNA
<213> ORGANISM: Artificial Sequence
<220> FEATURE:
<223> OTHER INFORMATION: Probe

<400> SEQUENCE: 10
aaacgaaagt ttaactaagc tatactaacc ccagggttgg tcaatttcgt gccagccacc       60
gcggtcacac gattaaccca agtcaataga agccggcgta aagagtgttt tagatcaccc     120

<210> SEQ ID NO 11
<211> LENGTH: 120
<212> TYPE: DNA
<213> ORGANISM: Artificial Sequence
<220> FEATURE:
<223> OTHER INFORMATION: Probe

```
<400> SEQUENCE: 11
ctacctaaga acagctaaaa gagcacaccc gtctatgtag caaaatagtg ggaagattta      60
taggtagagg cgacaaacct accgagcctg gtgatagctg gttgtccaag atagaatctt    120

<210> SEQ ID NO 12
<211> LENGTH: 120
<212> TYPE: DNA
<213> ORGANISM: Artificial Sequence
<220> FEATURE:
<223> OTHER INFORMATION: Probe

<400> SEQUENCE: 12
gatcacaggt ctatcaccct attaaccact cacgggagct ctccatgcat ttggtatttt      60
cgtctggggg gtgtgcacgc gatagcattg cgagacgctg gagccggagc accctatgtc    120

<210> SEQ ID NO 13
<211> LENGTH: 120
<212> TYPE: DNA
<213> ORGANISM: Artificial Sequence
<220> FEATURE:
<223> OTHER INFORMATION: Probe

<400> SEQUENCE: 13
gcagtatctg tctttgattc ctgcctcatt ctattattta tcgcacctac gttcaatatt      60
acaggcgaac atacctacta aagtgtgtta attaattaat gcttgtagga cataataata    120

<210> SEQ ID NO 14
<211> LENGTH: 120
<212> TYPE: DNA
<213> ORGANISM: Artificial Sequence
<220> FEATURE:
<223> OTHER INFORMATION: Probe

<400> SEQUENCE: 14
agacgttagg tcaaggtgta gcccatgagg tggcaagaaa tgggctacat tttctacccc      60
agaaaactac gatagccctt atgaaactta agggtcgaag gtggatttag cagtaaactg    120

<210> SEQ ID NO 15
<211> LENGTH: 120
<212> TYPE: DNA
<213> ORGANISM: Artificial Sequence
<220> FEATURE:
<223> OTHER INFORMATION: Probe

<400> SEQUENCE: 15
atctcatcaa tacaaccccc gcccatccta cccagcacac acaccgct gctaacccca      60 taccccgaac caaccaaacc ccaaagacac cccccacagt ttatgtagct tacctcctca    120

<210> SEQ ID NO 16
<211> LENGTH: 120
<212> TYPE: DNA
<213> ORGANISM: Artificial Sequence
<220> FEATURE:
<223> OTHER INFORMATION: Probe

<400> SEQUENCE: 16
taacacccat agtaggccta aaagcagcca ccaattaaga aagcgttcaa gctcaacacc      60
cactacctaa aaaatcccaa acatataact gaactcctca cacccaattg gaccaatcta    120

<210> SEQ ID NO 17
<211> LENGTH: 120
```

```
<212> TYPE: DNA
<213> ORGANISM: Artificial Sequence
<220> FEATURE:
<223> OTHER INFORMATION: Probe

<400> SEQUENCE: 17
tcaccctata gaagaactaa tgttagtata agtaacatga aaacattctc ctccgcataa      60
gcctgcgtca gatcaaaaca ctgaactgac aattaacagc ccaatatcta caatcaacca     120

<210> SEQ ID NO 18
<211> LENGTH: 120
<212> TYPE: DNA
<213> ORGANISM: Artificial Sequence
<220> FEATURE:
<223> OTHER INFORMATION: Probe

<400> SEQUENCE: 18
agttcaactt taaatttgcc cacagaaccc tctaaatccc cttgtaaatt taactgttag      60
tccaaagagg aacagctctt tggacactag gaaaaaacct tgtagagaga gtaaaaaatt     120

<210> SEQ ID NO 19
<211> LENGTH: 120
<212> TYPE: DNA
<213> ORGANISM: Artificial Sequence
<220> FEATURE:
<223> OTHER INFORMATION: Probe

<400> SEQUENCE: 19
ggagcctgtt ctgtaatcga taaacccega tcaacctcac cacctcttgc tcagcctata      60
taccgccatc ttcagcaaac cctgatgaag gctacaaagt aagcgcaagt acccacgtaa     120

<210> SEQ ID NO 20
<211> LENGTH: 120
<212> TYPE: DNA
<213> ORGANISM: Artificial Sequence
<220> FEATURE:
<223> OTHER INFORMATION: Probe

<400> SEQUENCE: 20
acaattgaat gtctgcacag ccgctttcca cacagacatc ataacaaaaa atttccacca      60 aaccccccc tcccccgct tctggccaca gcacttaaac acatctctgc caaaccccaa     120

<210> SEQ ID NO 21
<211> LENGTH: 120
<212> TYPE: DNA
<213> ORGANISM: Artificial Sequence
<220> FEATURE:
<223> OTHER INFORMATION: Probe

<400> SEQUENCE: 21
tgaaaaatta taaccaagca taatatagca aggactaacc cctataccett ctgcataatg      60 aattaactag aaataacttt gcaaggagag ccaaagctaa gaccccgaa accagacgag     120

<210> SEQ ID NO 22
<211> LENGTH: 120
<212> TYPE: DNA
<213> ORGANISM: Artificial Sequence
<220> FEATURE:
<223> OTHER INFORMATION: Probe

<400> SEQUENCE: 22
ttcggttggg gcgacctcgg agcagaaccc aacctccgag cagtacatgc taagacttca      60
```
ccagtcaaag cgaactacta tactcaattg atccaataac ttgaccaacg gaacaagtta    120

<210> SEQ ID NO 23
<211> LENGTH: 120
<212> TYPE: DNA
<213> ORGANISM: Artificial Sequence
<220> FEATURE:
<223> OTHER INFORMATION: Probe

<400> SEQUENCE: 23
ccctagggat aacagcgcaa tcctattcta gagtccatat caacaatagg gtttacgacc    60
tcgatgttgg atcaggacat cccgatggtg cagccgctat taaaggttcg tttgttcaac    120

<210> SEQ ID NO 24
<211> LENGTH: 120
<212> TYPE: DNA
<213> ORGANISM: Artificial Sequence
<220> FEATURE:
<223> OTHER INFORMATION: Probe

<400> SEQUENCE: 24
gattaaagtc ctacgtgatc tgagttcaga ccggagtaat ccaggtcggt ttctatctac    60
ttcaaattcc tccctgtacg aaaggacaag agaaataagg cctacttcac aaagcgcctt    120

<210> SEQ ID NO 25
<211> LENGTH: 120
<212> TYPE: DNA
<213> ORGANISM: Artificial Sequence
<220> FEATURE:
<223> OTHER INFORMATION: Probe

<400> SEQUENCE: 25
tatgaattcg aacagcatac ccccgattcc gctacgacca actcatacac ctcctatgaa    60
aaaacttcct accactcacc ctagcattac ttatatgata tgtctccata cccattacaa    120

<210> SEQ ID NO 26
<211> LENGTH: 120
<212> TYPE: DNA
<213> ORGANISM: Artificial Sequence
<220> FEATURE:
<223> OTHER INFORMATION: Probe

<400> SEQUENCE: 26
tagccgttta ctcaatcctc tgatcagggt gagcatcaaa ctcaaactac gccctgatcg    60
gcgcactgcg agcagtagcc caaacaatct catatgaagt caccctagcc atcattctac    120

<210> SEQ ID NO 27
<211> LENGTH: 120
<212> TYPE: DNA
<213> ORGANISM: Artificial Sequence
<220> FEATURE:
<223> OTHER INFORMATION: Probe

<400> SEQUENCE: 27
tatcaacatt actaataagt ggctccttta acctctccac ccttatcaca acacaagaac    60
acctctgatt actcctgcca tcatgaccct tggccataat atgatttatc tccacactag    120

<210> SEQ ID NO 28
<211> LENGTH: 120
<212> TYPE: DNA
<213> ORGANISM: Artificial Sequence
<220> FEATURE:
<223> OTHER INFORMATION: Probe

<400> SEQUENCE: 28
cagagaccaa ccgaaccccc ttcgaccttg ccgaagggga gtccgaacta gtctcaggct      60
tcaacatcga atacgccgca ggccccttcg ccctattctt catagccgaa tacacaaaca     120

<210> SEQ ID NO 29
<211> LENGTH: 120
<212> TYPE: DNA
<213> ORGANISM: Artificial Sequence
<220> FEATURE:
<223> OTHER INFORMATION: Probe

<400> SEQUENCE: 29
acatcaccgc cccgacctta gctctcacca tcgctcttct actatgaacc cccctcccca      60
tacccaaccc cctggtcaac ctcaacctag gcctccatt tattctagcc acctctagcc     120

<210> SEQ ID NO 30
<211> LENGTH: 120
<212> TYPE: DNA
<213> ORGANISM: Artificial Sequence
<220> FEATURE:
<223> OTHER INFORMATION: Probe

<400> SEQUENCE: 30
tacaactacg caaaggcccc aacgttgtag gcccctacgg gctactacaa cccttcgctg      60
acgccataaa actcttcacc aaagagcccc taaaaccgc cacatctacc atcaccctct      120

<210> SEQ ID NO 31
<211> LENGTH: 120
<212> TYPE: DNA
<213> ORGANISM: Artificial Sequence
<220> FEATURE:
<223> OTHER INFORMATION: Probe

<400> SEQUENCE: 31
ttattataat aaacaccctc accactacaa tcttcctagg aacaacatat gacgcactct      60
cccctgaact ctacacaaca tattttgtca ccaagaccct acttctaacc tccctgttct     120

<210> SEQ ID NO 32
<211> LENGTH: 120
<212> TYPE: DNA
<213> ORGANISM: Artificial Sequence
<220> FEATURE:
<223> OTHER INFORMATION: Probe

<400> SEQUENCE: 32
atccggcctg cttcttctca catgacaaaa actagccccc atctcaatca tataccaaat      60
ctctccctca ctaaacgtaa gccttctcct cactctctca atcttatcca tcatagcagg     120

<210> SEQ ID NO 33
<211> LENGTH: 120
<212> TYPE: DNA
<213> ORGANISM: Artificial Sequence
<220> FEATURE:
<223> OTHER INFORMATION: Probe

<400> SEQUENCE: 33
caatacttaa tttctgcaac agctaaggac tgcaaaaccc cactctgcat caactgaacg      60
caaatcagcc actttaatta agctaagccc ttactagacc aatgggactt aaacccacaa     120

<210> SEQ ID NO 34

```
<211> LENGTH: 120
<212> TYPE: DNA
<213> ORGANISM: Artificial Sequence
<220> FEATURE:
<223> OTHER INFORMATION: Probe

<400> SEQUENCE: 34
acacttagtt aacagctaag caccctaatc aactggcttc aatctacttc tcccgccgcc      60
gggaaaaaag gcgggagaag ccccggcagg tttgaagctg cttcttcgaa tttgcaattc     120

<210> SEQ ID NO 35
<211> LENGTH: 120
<212> TYPE: DNA
<213> ORGANISM: Artificial Sequence
<220> FEATURE:
<223> OTHER INFORMATION: Probe

<400> SEQUENCE: 35
caccctcctt aacctctact tctacctacg cctaatctac tccacctcaa tcacactact      60
ccccatatct aacaacgtaa aaataaaatg acagtttgaa catacaaaac ccaccccatt     120

<210> SEQ ID NO 36
<211> LENGTH: 120
<212> TYPE: DNA
<213> ORGANISM: Artificial Sequence
<220> FEATURE:
<223> OTHER INFORMATION: Probe

<400> SEQUENCE: 36
ccacggaagc aatatgaaat gatctgctgc agtgctctga gccctaggat tcatctttct      60
tttcaccgta ggtggcctga ctggcattgt attagcaaac tcatcactag acatcgtact     120

<210> SEQ ID NO 37
<211> LENGTH: 120
<212> TYPE: DNA
<213> ORGANISM: Artificial Sequence
<220> FEATURE:
<223> OTHER INFORMATION: Probe

<400> SEQUENCE: 37
cataaccaat actaccaatc aatactcatc attaataatc ataatggcta tagcaataaa      60
actaggaata gccccctttc acttctgagt cccagaggtt acccaaggca cccctctgac     120

<210> SEQ ID NO 38
<211> LENGTH: 120
<212> TYPE: DNA
<213> ORGANISM: Artificial Sequence
<220> FEATURE:
<223> OTHER INFORMATION: Probe

<400> SEQUENCE: 38
ccaacccgtc atctactcta ccatctttgc aggcacactc atcacagcgc taagctcgca      60 ctgattttt acctgagtag gcctagaaat aaacatgcta gcttttattc cagttctaac     120

<210> SEQ ID NO 39
<211> LENGTH: 120
<212> TYPE: DNA
<213> ORGANISM: Artificial Sequence
<220> FEATURE:
<223> OTHER INFORMATION: Probe

<400> SEQUENCE: 39
aactatttat attatcctaa ctactaccgc attcctacta ctcaacttaa actccagcac      60
```
cacgacccta ctactatctc gcacctgaaa caagctaaca tgactaacac ccttaattcc    120

<210> SEQ ID NO 40
<211> LENGTH: 120
<212> TYPE: DNA
<213> ORGANISM: Artificial Sequence
<220> FEATURE:
<223> OTHER INFORMATION: Probe

<400> SEQUENCE: 40
aattatcaat ataaaacccc ctgccataac ccaataccaa acgcccctct tcgtctgatc    60
cgtcctaatc acagcagtcc tacttctcct atctctccca gtcctagctg ctggcatcac    120

<210> SEQ ID NO 41
<211> LENGTH: 120
<212> TYPE: DNA
<213> ORGANISM: Artificial Sequence
<220> FEATURE:
<223> OTHER INFORMATION: Probe

<400> SEQUENCE: 41
agtctaccct cccttagcag ggaactactc ccaccctgga gcctccgtag acctaaccat    60
cttctcctta cacctagcag gtgtctcctc tatcttaggg gccatcaatt tcatcacaac    120

<210> SEQ ID NO 42
<211> LENGTH: 120
<212> TYPE: DNA
<213> ORGANISM: Artificial Sequence
<220> FEATURE:
<223> OTHER INFORMATION: Probe

<400> SEQUENCE: 42
cagttgaggt ggattaaacc aaacccagct acgcaaaatc ttagcatact cctcaattac    60
ccacatagga tgaataatag cagttctacc gtacaaccct aacataacca ttcttaattt    120

<210> SEQ ID NO 43
<211> LENGTH: 120
<212> TYPE: DNA
<213> ORGANISM: Artificial Sequence
<220> FEATURE:
<223> OTHER INFORMATION: Probe

<400> SEQUENCE: 43
caaaaaaata aaccctcgtt ccacagaagc tgccatcaag tatttcctca cgcaagcaac    60
cgcatccata atccttctaa tagctatcct cttcaacaat atactctccg acaatgaac    120

<210> SEQ ID NO 44
<211> LENGTH: 120
<212> TYPE: DNA
<213> ORGANISM: Artificial Sequence
<220> FEATURE:
<223> OTHER INFORMATION: Probe

<400> SEQUENCE: 44
attctctaca aaccacaaag acattggaac actataccta ttattcggcg catgagctgg    60
agtcctaggc acagctctaa gcctccttat tcgagccgag ctgggccagc caggcaacct    120

<210> SEQ ID NO 45
<211> LENGTH: 120
<212> TYPE: DNA
<213> ORGANISM: Artificial Sequence
<220> FEATURE:

<223> OTHER INFORMATION: Probe

<400> SEQUENCE: 45
cctaccaggc ttcggaataa tctcccatat tgtaacttac tactccggaa aaaaagaacc    60
atttggatac ataggtatgg tctgagctat gatatcaatt ggcttcctag ggtttatcgt   120

<210> SEQ ID NO 46
<211> LENGTH: 120
<212> TYPE: DNA
<213> ORGANISM: Artificial Sequence
<220> FEATURE:
<223> OTHER INFORMATION: Probe

<400> SEQUENCE: 46
tatactacta acagaccgca acctcaacac caccttcttc gaccccgccg gaggaggaga    60
ccccattcta taccaacacc tattctgatt tttcggtcac cctgaagttt atattcttat   120

<210> SEQ ID NO 47
<211> LENGTH: 120
<212> TYPE: DNA
<213> ORGANISM: Artificial Sequence
<220> FEATURE:
<223> OTHER INFORMATION: Probe

<400> SEQUENCE: 47
aacctacgcc aaaatccatt tcactatcat attcatcggc gtaaatctaa ctttcttccc    60
acaacacttt ctcggcctat ccggaatgcc ccgacgttac tcggactacc ccgatgcata   120

<210> SEQ ID NO 48
<211> LENGTH: 120
<212> TYPE: DNA
<213> ORGANISM: Artificial Sequence
<220> FEATURE:
<223> OTHER INFORMATION: Probe

<400> SEQUENCE: 48
caccacatga acatcctat catctgtagg ctcattcatt tctctaacag cagtaatatt    60
aataattttc atgatttgag aagccttcgc ttcgaagcga aaagtcctaa tagtagaaga   120

<210> SEQ ID NO 49
<211> LENGTH: 120
<212> TYPE: DNA
<213> ORGANISM: Artificial Sequence
<220> FEATURE:
<223> OTHER INFORMATION: Probe

<400> SEQUENCE: 49
atccaccctc ctctccctag gaggcctgcc ccgctaacc ggcttttttgc ccaaatgggc    60 cattatcgaa gaattcacaa aaaacaatag cctcatcatc cccaccatca tagccaccat   120

<210> SEQ ID NO 50
<211> LENGTH: 120
<212> TYPE: DNA
<213> ORGANISM: Artificial Sequence
<220> FEATURE:
<223> OTHER INFORMATION: Probe

<400> SEQUENCE: 50 cctcccccaca ctcatcgccc ttaccacgct actcctacct atctccccctt ttatactaat    60 aatcttatag aaatttaggt taaatacaga ccaagagcct tcaaagccct cagtaagttg   120

```
<210> SEQ ID NO 51
<211> LENGTH: 120
<212> TYPE: DNA
<213> ORGANISM: Artificial Sequence
<220> FEATURE:
<223> OTHER INFORMATION: Probe

<400> SEQUENCE: 51
aatatgaaaa tcacctcgga gctggtaaaa agaggcctaa cccctgtctt tagatttaca      60
gtccaatgct tcactcagcc attttacctc accccactg atgttcgccg accgttgact      120

<210> SEQ ID NO 52
<211> LENGTH: 120
<212> TYPE: DNA
<213> ORGANISM: Artificial Sequence
<220> FEATURE:
<223> OTHER INFORMATION: Probe

<400> SEQUENCE: 52
cggtgccccc gatatggcgt ttccccgcat aaacaacata agcttctgac tcttacctcc      60
ctctctccta ctcctgctcg catctgctat agtggaggcc ggagcaggaa caggttgaac      120

<210> SEQ ID NO 53
<211> LENGTH: 120
<212> TYPE: DNA
<213> ORGANISM: Artificial Sequence
<220> FEATURE:
<223> OTHER INFORMATION: Probe

<400> SEQUENCE: 53
gtgagcacac catatattta cagtaggaat agacgtagac acacgagcat atttcacctc      60
cgctaccata atcatcgcta tccccaccgg cgtcaaagta tttagctgac tcgccacact      120

<210> SEQ ID NO 54
<211> LENGTH: 120
<212> TYPE: DNA
<213> ORGANISM: Artificial Sequence
<220> FEATURE:
<223> OTHER INFORMATION: Probe

<400> SEQUENCE: 54
acacgacacg tactacgttg tagctcactt ccactatgtc ctatcaatag gagctgtatt      60
tgccatcata ggaggcttca ttcactgatt tcccctattc tcaggctaca ccctagacca      120

<210> SEQ ID NO 55
<211> LENGTH: 120
<212> TYPE: DNA
<213> ORGANISM: Artificial Sequence
<220> FEATURE:
<223> OTHER INFORMATION: Probe

<400> SEQUENCE: 55
tctaggtaac gaccacatct acaacgttat cgtcacagcc catgcatttg taataatctt      60
cttcatagta atacccatca taatcggagg ctttggcaac tgactagttc ccctaataat      120

<210> SEQ ID NO 56
<211> LENGTH: 120
<212> TYPE: DNA
<213> ORGANISM: Artificial Sequence
<220> FEATURE:
<223> OTHER INFORMATION: Probe

<400> SEQUENCE: 56
```

```
ctcaaccgcc ttttcatcaa tcgcccacat cactcgagac gtaaattatg gctgaatcat    60
ccgctacctt cacgccaatg gcgcctcaat attctttatc tgcctcttcc tacacatcgg   120
```

<210> SEQ ID NO 57
<211> LENGTH: 120
<212> TYPE: DNA
<213> ORGANISM: Artificial Sequence
<220> FEATURE:
<223> OTHER INFORMATION: Probe

<400> SEQUENCE: 57

```
gctatccatt ggtcttaggc cccaaaaatt ttggtgcaac tccaaataaa agtaataacc    60
atgcacacta ctataaccac cctaaccctg acttccctaa ttcccccat ccttaccacc   120
```

<210> SEQ ID NO 58
<211> LENGTH: 120
<212> TYPE: DNA
<213> ORGANISM: Artificial Sequence
<220> FEATURE:
<223> OTHER INFORMATION: Probe

<400> SEQUENCE: 58

```
tcttattatt tgatctagaa attgccctcc ttttacccct accatgagcc ctacaaacaa    60
ctaacctgcc actaatagtt atgtcatccc tcttattaat catcatccta gccctaagtc   120
```

<210> SEQ ID NO 59
<211> LENGTH: 120
<212> TYPE: DNA
<213> ORGANISM: Artificial Sequence
<220> FEATURE:
<223> OTHER INFORMATION: Probe

<400> SEQUENCE: 59

```
cttacgagcc aaaacctgcc cctactcctc ctagacctaa cctgactaga aaagctatta    60
cctaaaacaa tttcacagca ccaaatctcc acctccatca tcacctcaac ccaaaaaggc   120
```

<210> SEQ ID NO 60
<211> LENGTH: 120
<212> TYPE: DNA
<213> ORGANISM: Artificial Sequence
<220> FEATURE:
<223> OTHER INFORMATION: Probe

<400> SEQUENCE: 60

```
ctctcataac cctcaacacc cactccctct tagccaatat tgtgcctatt gccatactag    60
tctttgccgc ctgcgaagca gcggtgggcc tagccctact agtctcaatc tccaacacat   120
```

<210> SEQ ID NO 61
<211> LENGTH: 120
<212> TYPE: DNA
<213> ORGANISM: Artificial Sequence
<220> FEATURE:
<223> OTHER INFORMATION: Probe

<400> SEQUENCE: 61

```
ctcgttaacc ctaacaaaaa aaactcatac ccccattatg taaatccat tgtcgcatcc     60 acctttatta tcagtctctt ccccacaaca atattcatgt gcctagacca agaagttatt   120
```

<210> SEQ ID NO 62
<211> LENGTH: 120
<212> TYPE: DNA
<213> ORGANISM: Artificial Sequence

```
<220> FEATURE:
<223> OTHER INFORMATION: Probe

<400> SEQUENCE: 62
agcactcgaa taattcttct caccctaaca ggtcaacctc gcttccccac ccttactaac    60
attaacgaaa ataaccccac cctactaaac cccattaaac gcctggcagc cggaagccta   120

<210> SEQ ID NO 63
<211> LENGTH: 120
<212> TYPE: DNA
<213> ORGANISM: Artificial Sequence
<220> FEATURE:
<223> OTHER INFORMATION: Probe

<400> SEQUENCE: 63
atctcgaact gacactgagc cacaacccaa acaacccagc tctccctaag cttcaaacta    60
gactacttct ccataatatt catccctgta gcattgttcg ttacatggtc catcatagaa   120

<210> SEQ ID NO 64
<211> LENGTH: 120
<212> TYPE: DNA
<213> ORGANISM: Artificial Sequence
<220> FEATURE:
<223> OTHER INFORMATION: Probe

<400> SEQUENCE: 64
ttccaccccc tagcagaaaa tagcccacta atccaaactc taacactatg cttaggcgct    60
atcaccactc tgttcgcagc agtctgcgcc cttacacaaa atgacatcaa aaaaatcgta   120

<210> SEQ ID NO 65
<211> LENGTH: 120
<212> TYPE: DNA
<213> ORGANISM: Artificial Sequence
<220> FEATURE:
<223> OTHER INFORMATION: Probe

<400> SEQUENCE: 65
atggcctaga ctacgtacat aacctaaacc tactccaatg ctaaaactaa tcgtcccaac    60
aattatatta ctaccactga catgactttc caaaaagcac ataatttgaa tcaacacaac   120

<210> SEQ ID NO 66
<211> LENGTH: 120
<212> TYPE: DNA
<213> ORGANISM: Artificial Sequence
<220> FEATURE:
<223> OTHER INFORMATION: Probe

<400> SEQUENCE: 66
cttcctattc tacaccctag taggctccct tcccctactc atcgcactaa tttacactca    60
caacacccta ggctcactaa acattctact actcactctc actgcccaag aactatcaaa   120

<210> SEQ ID NO 67
<211> LENGTH: 120
<212> TYPE: DNA
<213> ORGANISM: Artificial Sequence
<220> FEATURE:
<223> OTHER INFORMATION: Probe

<400> SEQUENCE: 67
acaatcctag gcctacccgc cgcagtactg atcattctat ttccccctct attgatcccc    60
acctccaaat atctcatcaa caaccgacta atcaccaccc aacaatgact aatcaaacta   120
```

```
<210> SEQ ID NO 68
<211> LENGTH: 120
<212> TYPE: DNA
<213> ORGANISM: Artificial Sequence
<220> FEATURE:
<223> OTHER INFORMATION: Probe

<400> SEQUENCE: 68
cataattata acaagctcca tctgcctacg acaaacagac ctaaaatcgc tcattgcata      60
ctcttcaatc agccacatag ccctcgtagt aacagccatt ctcatccaaa ccccctgaag     120

<210> SEQ ID NO 69
<211> LENGTH: 120
<212> TYPE: DNA
<213> ORGANISM: Artificial Sequence
<220> FEATURE:
<223> OTHER INFORMATION: Probe

<400> SEQUENCE: 69
agattgtgaa tctgacaaca gaggcttacg acccttatt taccgagaaa gctcacaaga      60
actgctaact catgccccca tgtctaacaa catggctttc tcaacttta aaggataaca     120

<210> SEQ ID NO 70
<211> LENGTH: 120
<212> TYPE: DNA
<213> ORGANISM: Artificial Sequence
<220> FEATURE:
<223> OTHER INFORMATION: Probe

<400> SEQUENCE: 70
acaccaacca cccaactatc tataaaccta gccatggcca tcccttatg agcgggcgca      60 gtgattatag gctttcgctc taagattaaa atgccctag cccacttctt accacaaggc     120

<210> SEQ ID NO 71
<211> LENGTH: 120
<212> TYPE: DNA
<213> ORGANISM: Artificial Sequence
<220> FEATURE:
<223> OTHER INFORMATION: Probe

<400> SEQUENCE: 71
tttaagttaa agattaagag aaccaacacc tctttacagt gaaatgcccc aactaaatac      60
taccgtatgg cccaccataa ttaccccat actccttaca ctattcctca tcacccaact     120

<210> SEQ ID NO 72
<211> LENGTH: 120
<212> TYPE: DNA
<213> ORGANISM: Artificial Sequence
<220> FEATURE:
<223> OTHER INFORMATION: Probe

<400> SEQUENCE: 72
gttttcacac ttctagtaag cctctacctg cacgacaaca cataatgacc caccaatcac      60
atgcctatca tatagtaaaa cccagcccat gaccctaac aggggccctc tcagccctcc     120

<210> SEQ ID NO 73
<211> LENGTH: 120
<212> TYPE: DNA
<213> ORGANISM: Artificial Sequence
<220> FEATURE:
<223> OTHER INFORMATION: Probe

<400> SEQUENCE: 73
```
cacaccgcta acaatcagta ctaaacccca ataaatagga gaaggcttag aagaaaaccc        60
cacaaacccc attactaaac ccacactcaa cagaaacaaa gcatacatca ttattctcgc       120

<210> SEQ ID NO 74
<211> LENGTH: 120
<212> TYPE: DNA
<213> ORGANISM: Artificial Sequence
<220> FEATURE:
<223> OTHER INFORMATION: Probe

<400> SEQUENCE: 74
cttcaccggc gcagtcattc tcataatcgc ccacggactc acatcctcat tactattctg        60
cctagcaaac tcaaactacg aacgcactca cagtcgcatc ataatcctct ctcaaggact       120

<210> SEQ ID NO 75
<211> LENGTH: 120
<212> TYPE: DNA
<213> ORGANISM: Artificial Sequence
<220> FEATURE:
<223> OTHER INFORMATION: Probe

<400> SEQUENCE: 75
aaaaatatta aacacaaact accacctacc tccctcacca aagcccataa aaataaaaaa        60
ttataacaaa ccctgagaac caaaatgaac gaaaatctgt tcgcttcatt cattgccccc       120

<210> SEQ ID NO 76
<211> LENGTH: 120
<212> TYPE: DNA
<213> ORGANISM: Artificial Sequence
<220> FEATURE:
<223> OTHER INFORMATION: Probe

<400> SEQUENCE: 76
gagctcacca tagtctaata gaaaacaacc gaaaccaaat aattcaagca ctgcttatta        60
caattttact gggtctctat tttaccctcc tacaagcctc agagtacttc gagtctccct       120

<210> SEQ ID NO 77
<211> LENGTH: 120
<212> TYPE: DNA
<213> ORGANISM: Artificial Sequence
<220> FEATURE:
<223> OTHER INFORMATION: Probe

<400> SEQUENCE: 77
tctaatttaa actattctct gttctttcat ggggaagcag atttgggtac cacccaagta        60
ttgactcacc catcaacaac cgctatgtat ttcgtacatt actgccagcc accatgaata       120

<210> SEQ ID NO 78
<211> LENGTH: 120
<212> TYPE: DNA
<213> ORGANISM: Artificial Sequence
<220> FEATURE:
<223> OTHER INFORMATION: Probe

<400> SEQUENCE: 78
gcgaggccta tattacggat catttctcta ctcagaaacc tgaaacatcg gcattatcct        60
cctgcttgca actatagcaa cagccttcat aggctatgtc ctcccgtgag gccaaatatc       120

<210> SEQ ID NO 79
<211> LENGTH: 120
<212> TYPE: DNA

```
<213> ORGANISM: Artificial Sequence
<220> FEATURE:
<223> OTHER INFORMATION: Probe

<400> SEQUENCE: 79
ctcattcaca cgagaaaaca ccctcatgtt catacaccta tcccccattc tcctcctatc    60
cctcaacccc gacatcatta ccgggttttc tcttgtaaa tatagtttaa ccaaaacatc   120

<210> SEQ ID NO 80
<211> LENGTH: 120
<212> TYPE: DNA
<213> ORGANISM: Artificial Sequence
<220> FEATURE:
<223> OTHER INFORMATION: Probe

<400> SEQUENCE: 80
aactacctga ctcctacccc tcacaatcat ggcaagccaa cgccacttat ccagcgaacc    60
actatcacga aaaaaactct acctctctat actaatctcc ctacaaatct ccttaattat   120

<210> SEQ ID NO 81
<211> LENGTH: 120
<212> TYPE: DNA
<213> ORGANISM: Artificial Sequence
<220> FEATURE:
<223> OTHER INFORMATION: Probe

<400> SEQUENCE: 81
cacattaggc ttaaaaacag atgcaattcc cggacgtcta aaccaaacca ctttcaccgc    60
tacacgaccg ggggtatact acggtcaatg ctctgaaatc tgtggagcaa accacagttt   120

<210> SEQ ID NO 82
<211> LENGTH: 120
<212> TYPE: DNA
<213> ORGANISM: Artificial Sequence
<220> FEATURE:
<223> OTHER INFORMATION: Probe

<400> SEQUENCE: 82
ataattaaac tttacttcct ctctttcttc tcccactca tcctaaccct actcctaatc    60
acataaccta ttcccccgag caatctcaat tacaatatat acaccaacaa acaatgttca   120

<210> SEQ ID NO 83
<211> LENGTH: 120
<212> TYPE: DNA
<213> ORGANISM: Artificial Sequence
<220> FEATURE:
<223> OTHER INFORMATION: Probe

<400> SEQUENCE: 83
tggcctatga gtgactacaa aaaggattag actgagccga attggtatat agtttaaaca    60
aaacgaatga tttcgactca ttaaattatg ataatcatat ttaccaaatg cccctcattt   120

<210> SEQ ID NO 84
<211> LENGTH: 120
<212> TYPE: DNA
<213> ORGANISM: Artificial Sequence
<220> FEATURE:
<223> OTHER INFORMATION: Probe

<400> SEQUENCE: 84
cataccaagg ccaccacaca ccacctgtcc aaaaaggcct tcgatacggg ataatcctat    60
ttattacctc agaagttttt ttcttcgcag gatttttctg agccttttac cactccagcc   120
```

<210> SEQ ID NO 85
<211> LENGTH: 120
<212> TYPE: DNA
<213> ORGANISM: Artificial Sequence
<220> FEATURE:
<223> OTHER INFORMATION: Probe

<400> SEQUENCE: 85
ctcctcaata gccatcgctg tagtatatcc aaagacaacc atcattcccc ctaaataaat    60
taaaaaaact attaaaccca tataacctcc cccaaaattc agaataataa cacacccgac   120

<210> SEQ ID NO 86
<211> LENGTH: 120
<212> TYPE: DNA
<213> ORGANISM: Artificial Sequence
<220> FEATURE:
<223> OTHER INFORMATION: Probe

<400> SEQUENCE: 86 ataccttcc tcacaggttt ctactccaaa gaccacatca tcgaaaccgc aaacatatca    60
tacacaaacg cctgagccct atctattact ctcatcgcta cctccctgac aagcgcctat   120

<210> SEQ ID NO 87
<211> LENGTH: 120
<212> TYPE: DNA
<213> ORGANISM: Artificial Sequence
<220> FEATURE:
<223> OTHER INFORMATION: Probe

<400> SEQUENCE: 87
tagcccctac cccccaacta ggagggcact ggcccccaac aggcatcacc ccgctaaatc    60
ccctagaagt cccactccta aacacatccg tattactcgc atcaggagta tcaatcacct   120

<210> SEQ ID NO 88
<211> LENGTH: 120
<212> TYPE: DNA
<213> ORGANISM: Artificial Sequence
<220> FEATURE:
<223> OTHER INFORMATION: Probe

<400> SEQUENCE: 88
ggcctgtcct tgtagtataa actaatacac cagtcttgta aaccggagac gaaaacctt    60 ttccaaggac aaatcagaga aaagtctt aactccacca ttagcaccca aagctaagat   120

<210> SEQ ID NO 89
<211> LENGTH: 120
<212> TYPE: DNA
<213> ORGANISM: Artificial Sequence
<220> FEATURE:
<223> OTHER INFORMATION: Probe

<400> SEQUENCE: 89
aacagacgag gtcaacgatc cctcccttac catcaaatca attggccacc aatggtactg    60
aacctacgag tacaccgact acggcggact aatcttcaac tcctacatac ttccccatt   120

<210> SEQ ID NO 90
<211> LENGTH: 120
<212> TYPE: DNA
<213> ORGANISM: Artificial Sequence
<220> FEATURE:
<223> OTHER INFORMATION: Probe

<400> SEQUENCE: 90
ttctcactgt gatatataaa ctcagaccca aacattaatc agttcttcaa atatctactc        60
attttcctaa ttaccatact aatcttagtt accgctaaca acctattcca actgttcatc       120

<210> SEQ ID NO 91
<211> LENGTH: 120
<212> TYPE: DNA
<213> ORGANISM: Artificial Sequence
<220> FEATURE:
<223> OTHER INFORMATION: Probe

<400> SEQUENCE: 91
aatagtactt gccgcagtac tcttaaaact aggcggctat ggtataatac gcctcacact        60
cattctcaac cccctgacaa aacacatagc ctacccctt cttgtactat ccctatgagg       120

<210> SEQ ID NO 92
<211> LENGTH: 120
<212> TYPE: DNA
<213> ORGANISM: Artificial Sequence
<220> FEATURE:
<223> OTHER INFORMATION: Probe

<400> SEQUENCE: 92
aggacaacca gtaagctacc cttttaccat cattggacaa gtagcatccg tactatactt        60
cacaacaatc ctaatcctaa taccaactat ctccctaatt gaaaacaaaa tactcaaatg       120

<210> SEQ ID NO 93
<211> LENGTH: 120
<212> TYPE: DNA
<213> ORGANISM: Artificial Sequence
<220> FEATURE:
<223> OTHER INFORMATION: Probe

<400> SEQUENCE: 93
gacctcaact acctaaccaa caaacttaaa ataaaatccc cactatgcac attttatttc        60
tccaacatac tcggattcta ccctagcatc acacaccgca caatccccta tctaggcctt       120

<210> SEQ ID NO 94
<211> LENGTH: 120
<212> TYPE: DNA
<213> ORGANISM: Artificial Sequence
<220> FEATURE:
<223> OTHER INFORMATION: Probe

<400> SEQUENCE: 94
tcaccatttc cgacggcatc tacggctcaa cattttttgt agccacaggc ttccacggac        60
ttcacgtcat tattggctca actttcctca ctatctgctt catccgccaa ctaatatttc       120

<210> SEQ ID NO 95
<211> LENGTH: 120
<212> TYPE: DNA
<213> ORGANISM: Artificial Sequence
<220> FEATURE:
<223> OTHER INFORMATION: Probe

<400> SEQUENCE: 95
ctgcaactcc aaagccaccc ctcacccact aggataccaa caaacctacc caccctaac         60 agtacatagt acataaagtc atttaccgta catagcacat tacagtcaaa tcccttctcg       120

<210> SEQ ID NO 96
<211> LENGTH: 120

```
<212> TYPE: DNA
<213> ORGANISM: Artificial Sequence
<220> FEATURE:
<223> OTHER INFORMATION: Probe

<400> SEQUENCE: 96
cgacctcccc accccatcca acatctccgc atgatgaaac ttcggctcac tccttggcgc    60
ctgcctgatc ctccaaatca ccacaggact attcctagcc atacactact caccagacgc   120

<210> SEQ ID NO 97
<211> LENGTH: 120
<212> TYPE: DNA
<213> ORGANISM: Artificial Sequence
<220> FEATURE:
<223> OTHER INFORMATION: Probe

<400> SEQUENCE: 97
cttccaccct tactacacaa tcaaagacgc cctcggctta cttctcttcc ttctctcctt    60
aatgacatta acactattct caccagacct cctaggcgac ccagacaatt atacccctagc  120

<210> SEQ ID NO 98
<211> LENGTH: 120
<212> TYPE: DNA
<213> ORGANISM: Artificial Sequence
<220> FEATURE:
<223> OTHER INFORMATION: Probe

<400> SEQUENCE: 98
attctgaggg gccacagtaa ttacaaactt actatccgcc atcccataca ttgggacaga    60
cctagttcaa tgaatctgag gaggctactc agtagacagt cccaccctca cacgattctt   120

<210> SEQ ID NO 99
<211> LENGTH: 120
<212> TYPE: DNA
<213> ORGANISM: Artificial Sequence
<220> FEATURE:
<223> OTHER INFORMATION: Probe

<400> SEQUENCE: 99
ttcgcaggat ttctcattac taacaacatt tcccccgcat cccccttcca acaacaatc    60 ccctctacc taaaactcac agccctcgct gtcactttcc taggacttct aacagcccta   120

<210> SEQ ID NO 100
<211> LENGTH: 120
<212> TYPE: DNA
<213> ORGANISM: Artificial Sequence
<220> FEATURE:
<223> OTHER INFORMATION: Probe

<400> SEQUENCE: 100
accagtaacc actactaatc aacgcccata atcatacaaa gcccccgcac caataggatc    60
ctcccgaatc aaccctgacc cctctccttc ataaattatt cagcttccta cactattaaa   120

<210> SEQ ID NO 101
<211> LENGTH: 120
<212> TYPE: DNA
<213> ORGANISM: Artificial Sequence
<220> FEATURE:
<223> OTHER INFORMATION: Probe

<400> SEQUENCE: 101
attcctagaa ccaggcgacc tgcgactcct tgacgttgac aatcgagtag tactcccgat    60
```
tgaagccccc attcgtataa taattacatc acaagacgtc ttgcactcat gagctgtccc    120

<210> SEQ ID NO 102
<211> LENGTH: 120
<212> TYPE: DNA
<213> ORGANISM: Artificial Sequence
<220> FEATURE:
<223> OTHER INFORMATION: Probe

<400> SEQUENCE: 102
atcaaatatc actctcctac ttacaggact caacatacta gtcacagccc tatactccct    60
ctacatattt accacaacac aatggggctc actcacccac cacattaaca acataaaacc   120

<210> SEQ ID NO 103
<211> LENGTH: 120
<212> TYPE: DNA
<213> ORGANISM: Artificial Sequence
<220> FEATURE:
<223> OTHER INFORMATION: Probe

<400> SEQUENCE: 103
aaatcagccc aattaggtct ccacccctga ctccctcag ccatagaagg ccccacccca     60
gtctcagccc tactccactc aagcactata gttgtagcag gaatcttctt actcatccgc   120

<210> SEQ ID NO 104
<211> LENGTH: 120
<212> TYPE: DNA
<213> ORGANISM: Artificial Sequence
<220> FEATURE:
<223> OTHER INFORMATION: Probe

<400> SEQUENCE: 104
acctcaaaac aaatgatagc catacacaac actaaaggac gaacctgatc tcttatacta    60
gtatccttaa tcattttat tgccacaact aacctcctcg gactcctgcc tcactcattt   120

<210> SEQ ID NO 105
<211> LENGTH: 120
<212> TYPE: DNA
<213> ORGANISM: Artificial Sequence
<220> FEATURE:
<223> OTHER INFORMATION: Probe

<400> SEQUENCE: 105
acacctacac cccttatccc catactagtt attatcgaaa ccatcagcct actcattcaa    60
ccaatagccc tggccgtacg cctaaccgct aacattactg caggccacct actcatgcac   120

<210> SEQ ID NO 106
<211> LENGTH: 120
<212> TYPE: DNA
<213> ORGANISM: Artificial Sequence
<220> FEATURE:
<223> OTHER INFORMATION: Probe

<400> SEQUENCE: 106
tacctttcac ttcatcttac ccttcattat tgcagcccta gcagcactcc acctcctatt    60
cttgcacgaa acgggatcaa acaaccccct aggaatcacc tcccattccg ataaaatcac   120

<210> SEQ ID NO 107
<211> LENGTH: 120
<212> TYPE: DNA
<213> ORGANISM: Artificial Sequence
<220> FEATURE:
<223> OTHER INFORMATION: Probe

<400> SEQUENCE: 107
atcctcgcct tagcatgatt tatcctacac tccaactcat gagacccaca acaaatagcc    60
cttctaaacg ctaatccaag cctcacccca ctactaggcc tcctcctagc agcagcaggc   120

<210> SEQ ID NO 108
<211> LENGTH: 120
<212> TYPE: DNA
<213> ORGANISM: Artificial Sequence
<220> FEATURE:
<223> OTHER INFORMATION: Probe

<400> SEQUENCE: 108
taatgacctc cggcctagcc atgtgatttc acttccactc cataacgctc ctcatactag    60
gcctactaac caacacacta accatatacc aatggtggcg cgatgtaaca cgagaaagca   120

<210> SEQ ID NO 109
<211> LENGTH: 120
<212> TYPE: DNA
<213> ORGANISM: Artificial Sequence
<220> FEATURE:
<223> OTHER INFORMATION: Probe

<400> SEQUENCE: 109
acggactaca accacgacca atgatatgaa aaaccatcgt tgtatttcaa ctacaagaac    60
accaatgacc ccaatacgca aaattaaccc cctaataaaa ttaattaacc actcattcat   120

<210> SEQ ID NO 110
<211> LENGTH: 120
<212> TYPE: DNA
<213> ORGANISM: Artificial Sequence
<220> FEATURE:
<223> OTHER INFORMATION: Probe

<400> SEQUENCE: 110
gccttctcca cttcaagtca actaggactc ataatagtta caatcggcat caaccaacca    60
cacctagcat tcctgcacat ctgtacccac gccttcttca aagccatact atttatgtgc   120

<210> SEQ ID NO 111
<211> LENGTH: 120
<212> TYPE: DNA
<213> ORGANISM: Artificial Sequence
<220> FEATURE:
<223> OTHER INFORMATION: Probe

<400> SEQUENCE: 111
acataaatat tatactagca tttaccatct cacttctagg aatactagta tatcgctcac    60
acctcatatc ctccctacta tgcctagaag gaataatact atcgctgttc attatagcta   120

<210> SEQ ID NO 112
<211> LENGTH: 120
<212> TYPE: DNA
<213> ORGANISM: Artificial Sequence
<220> FEATURE:
<223> OTHER INFORMATION: Probe

<400> SEQUENCE: 112
cacaacaaaa ctaactaata ctaacatctc agacgctcag gaaatagaaa ccgtctgaac    60
tatcctgccc gccatcatcc tagtcctcat cgccctccca tccctacgca tcctttacat   120

<210> SEQ ID NO 113

```
<211> LENGTH: 120
<212> TYPE: DNA
<213> ORGANISM: Artificial Sequence
<220> FEATURE:
<223> OTHER INFORMATION: Probe

<400> SEQUENCE: 113
ctcctgagcc aacaacttaa tatgactagc ttacacaata gcttttatag taaagatacc      60
tctttacgga ctccacttat gactccctaa agcccatgtc gaagccccca tcgctgggtc     120

<210> SEQ ID NO 114
<211> LENGTH: 120
<212> TYPE: DNA
<213> ORGANISM: Artificial Sequence
<220> FEATURE:
<223> OTHER INFORMATION: Probe

<400> SEQUENCE: 114
taaatagtac cgttaacttc caattaacta gttttgacaa cattcaaaaa agagtaataa      60
acttcgcctt aattttaata atcaacaccc tcctagcctt actactaata attattacat    120

<210> SEQ ID NO 115
<211> LENGTH: 120
<212> TYPE: DNA
<213> ORGANISM: Artificial Sequence
<220> FEATURE:
<223> OTHER INFORMATION: Probe

<400> SEQUENCE: 115
ggctgagagg gcgtaggaat tatatccttc ttgctcatca gttgatgata cgcccgagca      60
gatgccaaca cagcagccat tcaagcagtc ctatacaacc gtatcggcga tatcggtttc    120

<210> SEQ ID NO 116
<211> LENGTH: 120
<212> TYPE: DNA
<213> ORGANISM: Artificial Sequence
<220> FEATURE:
<223> OTHER INFORMATION: Probe

<400> SEQUENCE: 116
ttgtacggta ccataaatac ttgaccacct gtagtacata aaacccaac ccacatcaaa      60 ccccccccc ccatgcttac aagcaagtac agcaatcaac cttcaactat cacacatcaa    120

<210> SEQ ID NO 117
<211> LENGTH: 120
<212> TYPE: DNA
<213> ORGANISM: Artificial Sequence
<220> FEATURE:
<223> OTHER INFORMATION: Probe

<400> SEQUENCE: 117
gtttaccaca accaccaccc catcatactc tttcacccac agcaccaatc ctacctccat      60 cgctaaccccc actaaaacac tcaccaagac ctcaacccct gaccccatg cctcaggata    120

<210> SEQ ID NO 118
<211> LENGTH: 120
<212> TYPE: DNA
<213> ORGANISM: Artificial Sequence
<220> FEATURE:
<223> OTHER INFORMATION: Probe

<400> SEQUENCE: 118
ctaattggaa gcgccaccct agcaatatca accattaacc ttccctctac acttatcatc      60
```

```
ttcacaattc taattctact gactatccta gaaatcgctg tcgccttaat ccaagcctac    120
```

<210> SEQ ID NO 119
<211> LENGTH: 120
<212> TYPE: DNA
<213> ORGANISM: Artificial Sequence
<220> FEATURE:
<223> OTHER INFORMATION: Probe

<400> SEQUENCE: 119

```
catcctagca ataatcccca tcctccatat atccaaacaa caaagcataa tatttcgccc     60
actaagccaa tcactttatt gactcctagc cgcagacctc ctcattctaa cctgaatcgg    120
```

<210> SEQ ID NO 120
<211> LENGTH: 120
<212> TYPE: DNA
<213> ORGANISM: Artificial Sequence
<220> FEATURE:
<223> OTHER INFORMATION: Probe

<400> SEQUENCE: 120

```
catgcccatc gtcctagaat taattcccct aaaaatcttt gaaatagggc ccgtatttac     60
cctatagcac cccctctacc ccctctagag cccactgtaa agctaactta gcattaacct    120
```

<210> SEQ ID NO 121
<211> LENGTH: 120
<212> TYPE: DNA
<213> ORGANISM: Artificial Sequence
<220> FEATURE:
<223> OTHER INFORMATION: Probe

<400> SEQUENCE: 121

```
aacattcaca gccacagaac taatcatatt ttatatcttc ttcgaaacca cacttatccc     60
caccttggct atcatcaccc gatgaggcaa ccagccagaa cgcctgaacg caggcacata    120
```

<210> SEQ ID NO 122
<211> LENGTH: 120
<212> TYPE: DNA
<213> ORGANISM: Artificial Sequence
<220> FEATURE:
<223> OTHER INFORMATION: Probe

<400> SEQUENCE: 122

```
tttgactacc acaactcaac ggctacatag aaaaatccac cccttacgag tgcggcttcg     60
accctatatc ccccgcccgc gtccctttct ccataaaatt cttcttagta gctattacct    120
```

<210> SEQ ID NO 123
<211> LENGTH: 120
<212> TYPE: DNA
<213> ORGANISM: Artificial Sequence
<220> FEATURE:
<223> OTHER INFORMATION: Probe

<400> SEQUENCE: 123

```
agtaggtcta caagacgcta cttcccctat catagaagag cttatcacct ttcatgatca     60 cgcccctcata atcattttcc ttatctgctt cctagtcctg tatgcccttt tcctaacact    120
```

<210> SEQ ID NO 124
<211> LENGTH: 120
<212> TYPE: DNA
<213> ORGANISM: Artificial Sequence
<220> FEATURE:

<223> OTHER INFORMATION: Probe

<400> SEQUENCE: 124
cacccacagc taattatta gcatcatccc cctactattt tttaaccaaa tcaacaacaa    60
cctatttagc tgttccccaa ccttttcctc cgaccccta acaaccccc tcctaatact    120

<210> SEQ ID NO 125
<211> LENGTH: 120
<212> TYPE: DNA
<213> ORGANISM: Artificial Sequence
<220> FEATURE:
<223> OTHER INFORMATION: Probe

<400> SEQUENCE: 125
caacccctta acacccctc cccacatcaa gcccgaatga tatttcctat tcgcctacac    60
aattctccga tccgtcccta acaaactagg aggcgtcctt gccctattac tatccatcct   120

<210> SEQ ID NO 126
<211> LENGTH: 120
<212> TYPE: DNA
<213> ORGANISM: Artificial Sequence
<220> FEATURE:
<223> OTHER INFORMATION: Probe

<400> SEQUENCE: 126
actttacatc caaacatcac tttggcttcg aagccgccgc ctgatactgg cattttgtag    60
atgtggtttg actatttctg tatgtctcca tctattgatg agggtcttac tcttttagta   120

<210> SEQ ID NO 127
<211> LENGTH: 120
<212> TYPE: DNA
<213> ORGANISM: Artificial Sequence
<220> FEATURE:
<223> OTHER INFORMATION: Probe

<400> SEQUENCE: 127
tccgggtcca tcatccacaa ccttaacaat gaacaagata ttcgaaaaat aggaggacta    60
ctcaaaacca tacctctcac ttcaacctcc ctcaccattg gcagcctagc attagcagga   120

<210> SEQ ID NO 128
<211> LENGTH: 120
<212> TYPE: DNA
<213> ORGANISM: Artificial Sequence
<220> FEATURE:
<223> OTHER INFORMATION: Probe

<400> SEQUENCE: 128
tcaaactcta ctcccactaa tagcttttg atgacttcta gcaagcctcg ctaacctcgc    60 cttaccccc actattaacc tactgggaga actctctgtg ctagtaacca cgttctcctg    120

<210> SEQ ID NO 129
<211> LENGTH: 120
<212> TYPE: DNA
<213> ORGANISM: Artificial Sequence
<220> FEATURE:
<223> OTHER INFORMATION: Probe

<400> SEQUENCE: 129
tccccatgga tgacccccct cagatagggg tccttgacc accatcctcc gtgaaatcaa    60
tatcccgcac aagagtgcta ctctcctcgc tccgggccca taacacttgg gggtagctaa   120

```
<210> SEQ ID NO 130
<211> LENGTH: 120
<212> TYPE: DNA
<213> ORGANISM: Artificial Sequence
<220> FEATURE:
<223> OTHER INFORMATION: Probe

<400> SEQUENCE: 130
ccccgtaaat gatatcatct caacttagta ttatacccac acccacccaa gaacagggtt      60
tgttaagatg gcagagcccg gtaatcgcat aaaacttaaa actttacagt cagaggttca     120

<210> SEQ ID NO 131
<211> LENGTH: 120
<212> TYPE: DNA
<213> ORGANISM: Artificial Sequence
<220> FEATURE:
<223> OTHER INFORMATION: Probe

<400> SEQUENCE: 131
ttcctcttct taacaacata cccatggcca acctcctact cctcattgta cccattctaa      60
tcgcaatggc attcctaatg cttaccgaac gaaaaattct aggctatata caactacgca    120
```